(12) United States Patent
Condon et al.

(10) Patent No.: US 7,456,209 B2
(45) Date of Patent: Nov. 25, 2008

(54) IAP BINDING COMPOUNDS

(75) Inventors: Stephen M. Condon, Glenmoore, PA (US); Matthew G. LaPorte, Honeybrook, PA (US); Yijun Deng, Dresher, PA (US); Susan R. Rippin, Wilmington, DE (US)

(73) Assignee: Tetralogic Pharmaceuticals Corporation, Malvern, PA (US)

( * ) Notice: Subject to any disclaimer, the term of this patent is extended or adjusted under 35 U.S.C. 154(b) by 343 days.

(21) Appl. No.: 11/184,503

(22) Filed: Jul. 15, 2005

(65) Prior Publication Data

US 2006/0025347 A1 Feb. 2, 2006

Related U.S. Application Data

(60) Provisional application No. 60/588,050, filed on Jul. 15, 2004.

(51) Int. Cl.
*A61K 31/405* (2006.01)
*C07D 209/12* (2006.01)

(52) U.S. Cl. .................. 514/415; 514/419; 514/422; 514/428; 548/494; 548/517; 548/566

(58) Field of Classification Search .......... 548/494, 548/517, 566; 514/415, 419, 422, 428
See application file for complete search history.

(56) References Cited

U.S. PATENT DOCUMENTS

| | | | |
|---|---|---|---|
| 3,832,253 A | 8/1974 | DiPalma et al. | |
| 3,854,480 A | 12/1974 | Zaffaroni | |
| 4,278,793 A | 7/1981 | Durckheimer et al. | |
| 4,452,775 A | 6/1984 | Kent | |
| 4,667,014 A | 5/1987 | Nestor, Jr. et al. | |
| 4,748,034 A | 5/1988 | De Rham | |
| 5,075,109 A | 12/1991 | Tice et al. | |
| 5,239,660 A | 8/1993 | Ooi | |
| 5,660,811 A | 8/1997 | Mills | |
| 5,766,572 A | 6/1998 | Hasegawa et al. | |
| 6,110,691 A | 8/2000 | Wang et al. | |
| 6,133,437 A | 10/2000 | Korneluk et al. | |
| 6,187,557 B1 | 2/2001 | Rothe et al. | |
| 6,338,835 B1 | 1/2002 | Shochat et al. | |
| 6,608,026 B1 | 8/2003 | Wang | |
| 6,911,426 B2 | 6/2005 | Reed et al. | |
| 6,992,063 B2 | 1/2006 | Shi | |
| 7,244,851 B2 | 7/2007 | Cohen et al. | |
| 2002/0132786 A1 | 9/2002 | Alnemri et al. | |
| 2002/0160975 A1 | 10/2002 | Alnemri | |
| 2002/0177557 A1 | 11/2002 | Shi | |
| 2004/0054148 A1 | 3/2004 | Alnemri | |
| 2005/0197403 A1 | 9/2005 | Harran et al. | |
| 2005/0234042 A1 | 10/2005 | Palermo et al. | |
| 2005/0261203 A1 | 11/2005 | Cohen et al. | |
| 2006/0014700 A1 | 1/2006 | Cohen et al. | |
| 2006/0025347 A1 | 2/2006 | Condon et al. | |
| 2006/0052311 A1 | 3/2006 | Sharma et al. | |
| 2006/0128632 A1 | 6/2006 | Sharma et al. | |
| 2006/0167066 A1 | 7/2006 | Cohen et al. | |
| 2006/0194741 A1 | 8/2006 | Condon et al. | |
| 2006/0258581 A1 | 11/2006 | Reed et al. | |
| 2006/0264379 A1 | 11/2006 | Jarvis et al. | |
| 2007/0003535 A1 | 1/2007 | Reed et al. | |
| 2007/0042428 A1 | 2/2007 | Springs et al. | |
| 2007/0093428 A1 | 4/2007 | Laurent | |
| 2007/0093429 A1 | 4/2007 | Laurent et al. | |

FOREIGN PATENT DOCUMENTS

| | | |
|---|---|---|
| WO | WO 99/15657 A2 | 4/1999 |
| WO | WO 02/16418 A1 | 2/2002 |
| WO | WO 02/26775 A2 | 4/2002 |
| WO | WO 02/30959 A2 | 4/2002 |
| WO | WO 02/096930 A2 | 12/2002 |
| WO | WO 03/018014 A2 | 3/2003 |
| WO | WO 2004/005248 | 1/2004 |
| WO | WO 2004/007529 A2 | 1/2004 |
| WO | WO2004005248 * | 1/2004 |
| WO | WO 2004/072105 A2 | 8/2004 |
| WO | WO 2005/069888 | 8/2005 |
| WO | WO 2005/069894 | 8/2005 |
| WO | WO 2005/078989 A2 | 8/2005 |
| WO | WO 2005/084317 A2 | 9/2005 |
| WO | WO 2005/094818 A1 | 10/2005 |
| WO | WO 2005/097791 A1 | 10/2005 |
| WO | WO 2006/010118 A2 | 1/2006 |
| WO | WO 2006/014361 | 2/2006 |

(Continued)

OTHER PUBLICATIONS

Macor et al., The Synthesis of a Conformationally Restricted Analog of the Anti-Migraine Drug Sumatriptan, 1992, Tetrahedron Lett. 33(52):8011-8014.

(Continued)

*Primary Examiner*—Rei-tsang Shiao
(74) *Attorney, Agent, or Firm*—Banner & Witcoff, Ltd.

(57) ABSTRACT

IAP binding molecules and compositions including these are disclosed. The IAP binding molecules interact with IAPs (inhibitor of apoptosis proteins) in cells and may be used to modify apoptosis in cells treated with such molecules. Embodiments of these compounds have a $K_d$ of less that 0.1 micromolar. Methods of using these IAP binding molecules for therapeutic, diagnostic, and assay purposes are also disclosed.

16 Claims, No Drawings

FOREIGN PATENT DOCUMENTS

| WO | WO 2006/017295 A2 | 2/2006 |
|---|---|---|
| WO | WO 2006/020060 A2 | 2/2006 |
| WO | WO 2006/069063 | 6/2006 |
| WO | WO 2006/091972 | 8/2006 |
| WO | WO 2006/122408 | 11/2006 |
| WO | WO 2006/128455 | 12/2006 |
| WO | WO 2006/133147 | 12/2006 |
| WO | WO 2007/101347 | 9/2007 |
| WO | WO 2007/106192 | 9/2007 |
| WO | WO 2007/130626 | 11/2007 |

OTHER PUBLICATIONS

Chawla-Sarkar, Preferential Induction of Apoptosis by Interferon (IFN)-β Compared with IFN-α2: Correlation with TRAIL/Apo2L Induction in Melanoma Cell Lines, 2001, Clin. Can. Res. 7:1821-1831.
Sun et al., Structure-based Design of Potent, Conformationally Constrained Smac Mimetics, 2004, J. Am. Chem. Soc. 126:16686-16687.
Park et al., Non-peptide small molecule inhibitors of XIAP, 2004, Bioorganic & Med. Chem. Lett. 15:771-775.
Lang's Handbook of Chemistry, Dean ed., Table 7-2, 1985.
Fulda et al., Smac agonists sensitized for Apo2L/TRAIL-or anticancer drug-induced apoptosis and induce regression of Malignant glioma in vivo, 2002, Nat. Med. 8(8):808-815.
Wu et al., Structural Analysis of a Functional DIAP1 Fragment Bound to Grim and Hid Peptides, 2001, Mol. Cell 8:95-104.
Oost et al., Discovery of Potent Antagonists of the Antiapoptotic Protein XIAP for the Treatment of Cancer, 2004, J. Med. Chem. 47:4417-4426.
Chai et al., Structural and biochemical basis of apoptotic activation by Smac/DIABLO, 2000, Nature 406:855-862.
Ambrosini et al., Induction of Apoptosis and Inhibition of Cell Proliferation by survivin Gene Targeting, 1998, J. Biol. Chem. 273(18):11177-11182.
Ripka et al., Peptidomimetic design, 1998, Curr. Op. Chem. Biol. 2:441-452.
Hruby et al., Synthesis of oligopeptide and peptidomimetic libraries, 1997, Curr. Op. Chem. Biol. 1:114-119.
Hruby et al., Conformational and Topographical Considerations in Designing Agonist Peptidomimetics from Peptide Leads, 2000, Curr. Med. Chem. 9:945-970.
Wyllie et al., Cell Death: the significance of apoptosis, 1980, Int. Rev. Cytol. 68:251-306.
Wyllie, Glucocorticoid-induced thymocyte apoptosis is associated with endogenous endonuclease activation, 1981, Nature 284:555-556.
Gennaro, Remington's Pharmaceutical Sciences, Mack Publ. Co., Easton, PA (TOC).
Craig et al., Modern Pharmacology with Clinical Applications, 6th ed., Kerins ed., Ch. 56:639-656.
Hay, Understanding IAP function and regulation: a view from *Drosophila*, 2000, Cell Death and Diff. 7:1045-1056.
Chan et al., Fmoc Solid Phase Peptide Synthesis: A Practical Approach, 2000, Oxford University Press (TOC).
Boxrud et al., Streptokinase Binds to Human Plasmin with High Affinity, Perturbs the Plasmin Active Site, and Induces Expression of a Substrate Recognition Exosite for Plasminogen, 2000, J. Biol. Chem. 275(19):14579-14589.
Owenius et al., Properties of Spin and Fluorescent Labels at a Receptor-Ligand Interface, 1999, Biophys. J. 77:2237-2250.
Hiratsuka, ATP-induces Opposite Changes in the Local Environments around $Cys^{697}$ (SH2) and $Cys^{707}$ (SH1) of the Myosin Motor Domain Revealed by the Prodan Fluorescence, 1999, J. Biol. Chem. 274(41):29156-29163.
Wu et al., Structural basis of IAP recognition by Smac/DIALBO, 2000, Nature 408:1008-1012.
Brunger, X-PLOR, a System for Crystallography and NMR, Yale University Press, New Haven, CT, 1991.
Chen et al., Grim, a novel cell death gene in *Drospohila*, 1996, Genes & Devel. 10:1773-1782.

Goyal et al., Induction of apoptosis by *Drosophila* reaper, hid and grim through inhibition of IAP function, 2000, Embo J. 19(4):589-597.
Jones et al., Improved methods for building protein models in electron density maps and the location of errors in these models, 1991, Acta Crystallogr. A47:110-119.
Kraulis, Molscript: a program to produce both detailed and schematic plots of protein structures, 1991, J. Appl. Crystallogr. 24:946-950.
Lisi et al., Diverse Domains of THREAD/DIAPI are Required to Inhibit Apoptosis Induced by REAPER and HID in *Drosophila*, 1999, Genetics Soc. Am. 154:669-678.
Liu, Structural basis for binding of Smac/DIABLO to the XIAP BIR3 domain, Dec. 2000, Nature, pp. 1004-1008.
McCarthy et al., Apoptosis induced by *Drosophila* reaper and grim in a human system, 1999, J. Biol. Chem. 273(37):24009-24015.
Morgan et al., Approaches to the Discovery of Non-Peptide Ligands for Peptide Receptors and Peptidases. 1989, Ann. Rep. Med. Chem. 243-252.
Navaza, AmoRe: an Automated Package for Molecular Replacement, 1994, Acta Cryst. A50:157-163.
Nicholls et al., Protein folding and association: insights from the interfacial and thermodynamic properties of hydrocarbons, 1991, Proteins: Struct. Funct. & Genet. 11:281-296.
Srinivasa et al., A conserved XIAP-interaction motif in caspase-9 and Smac/DIABLO regulates caspase activity and apoptosis, 2001, Nature 410:112-116.
Sun et al., NMR Structure and Mutagenesis of the Third Bir Domain of the Inhibitor Apoptosis Protein XIAP, 2000, J. Biol. Chem. 275(43):33777-33781.
Terwilliger et al., The CCP4 suite: Programs for protein crystallography, 1994, Acta Crystallogr. D50:760-763.
Terwilliger et al., Correlated Phasing of Multiple Isomorphous Replacement Data, 1996, Acta Crystallogr. D52:749-757.
Vucic et al., Inhibition of Reaper-induced apoptosis by interaction with inhibitor of apoptosis proteins (IAPS), 1997, Proc. Natl. Acad. Sci. USA 94:10183-10188.
Stellar, Mechanisms and Genes of Cellular Suicide, 1995, Science 267:1445-1449.
Jacobson et al., Programmed Cell Death in Animal Development, 1997, Cell 88:347-354.
Hengartner, Programmed cell death in invertebrates, 1996, Curr. Opin. Genet. Dev. 6:34-38.
Horvitz, Genetic Control of Programmed Cell Death in the Nematode *Caenorhabditis elegans*, 1999, Can. Res. 59:1701s-1706s.
Miller, An exegesis of IAPs: salvation and surprises from BIR motifs, 1999, Cell Biol. 9:323-328.
Deveraux et al., Cleavage of human inhibitor of apoptosis protein XIAP results in fragments with distinct specificities for caspases, 1999, Embo J. 18(19):5242-5251.
Takahashi et al., A Single BIR Domain XIAP Sufficient for Inhibiting Caspases, 1998, J. Biol. Chem. 273(14):7787-7790.
Sun et al., NMR structure and mutagenesis of the inhibitor-of-apoptosis protein XIAP, 1999, Nature 40:818-822.
SHI, Survivin structure: crystal unclear, 2000, Nat. Str. Biol. 7(8):620-623.
Verdecia et al., Structure of the human anti-apoptotic protein surviving reveals a dimeric arrangement, 2000, Nat. Stur. Biol. 7(7):602-608.
Chantalat et al., Crystal Structure of Human Survivin Reveals a Bow Tie-Shaped Dimer with Two Unusual α- Helical Extensions, 2000, Mol. Cell. 6:183-189.
Wang et al., The *Drosphila* Caspase Inhibitor DIAP1 is Essential for Cell Survival and Is Negatively Regulated by HID, 1999, Cell 98:453-463.
Hirel et al., Extent of N-terminal methionine excision from *Escherichia coli* proteins is governed by the side-chain length of the penultimate amino acid, 1989, Proc. Natl. Acad. Sci. USA 86:8247-8251.
Freidinger et al., Synthesis of 9pflourenylmethyloxycarbobyl-protected n-alkyl amino acids by reductin of oxazolidinones, 1983, J. Org. Chem. 48:77-81.

Srinivasa et al., Molecular Determinants of the Caspase-promoting activity of Smac/DIABLO and its role in the death receptor pathway, 2000, J. Biol. Chem. 275(46):36152-36157.

Zuckerman et al., Efficient Method for the Preparation of Peptoids [Oligo(N-substituted glycines)] by Submonomer Solid-Phase Synthesis, 1992, J. Am. Chem. Soc. 114:10646-10647.

Weinstein ed., Chemistry and Biochemistry of Amino Acids, Peptides, and Proteins, 1983, Marcel Dekker, Inc., New York, New York (TOC).

Deveraux et al., IAP family proteins-suppressors of apoptosis, 1999, Genes & Devel. 13:239-252.

Kasof et al., Livin, a Novel Inhibitor of Apoptosis Protein Family Member, 2001, J. Biol. Chem. 276(5):3238-3246.

Vucic et al., ML-IAP, a novel inhibitor of apoptosis that is preferentially expressed in human melanomas, 2000, Curr. Biol. 10:1359-1366.

Ashhab et al., two splicing variants of a new inhibitor of apoptosis gene with different biological properties and tissue distribution pattern, 2001, FEBS Lett. 495:56-60.

Du et al., Smac, a mitochondrial Protein that Promotes Cytochrome c-Dependent Caspase Activation by Eliminating IAP Inhibition, 2000, Cell 102:33-42.

Verhagen et al., Identification of DIABLO, a Mammalian Protein that Promotes Apoptosis by Binding to and Antagonizing IAP Proteins, 2000, Cell 102:43-53.

Vucic et al., Engineering ML-IAP to produce an extraordinarily potent caspase 9 inhibitor: implications for Smac-dependent anti-apoptotic activity of ML-IAP, 2005, Biochem. J. 385(1):11-20.

Nikolovska-Coleska et al., Development and Optimization of a Binding Assay for the XIAP BIR3 Domain Using Fluorescence Polarization, 2004 Analytical Biochem. 332:261-273.

Hasen et al., Re-examination and further development of a precise and rapid dye method for measuring cell growth/cell kill, 1989, J. Immunol. Methods 119:203-210.

\* cited by examiner

IAP BINDING COMPOUNDS

CROSS REFERENCE TO RELATED APPLICATIONS

This application claims the benefit of U.S. Provisional Application No. 60/588,050, filed Jul. 15, 2004, which is incorporated herein in its entirety by reference thereto.

BACKGROUND

Apoptosis, programmed cell death, plays a central role in the development and homeostasis of all multi-cellular organisms. Alterations in apoptotic pathways have been implicated in many types of human pathologies, including developmental disorders, cancer, autoimmune diseases, as well as neurodegenerative disorders.

Programmed cell death pathways have become targets for the development of therapeutic agents. In some cases because it is easier to destroy diseased cells rather than to sustain them, anti-cancer therapies using pro-apoptotic agents such as conventional radiation and chemo-therapy have been used to trigger activation of the mitochondria-mediated apoptotic pathways. However, these therapies lack molecular specificity, and more specific molecular targets are needed.

Apoptosis is executed primarily by activated caspases, a family of cysteine proteases with aspartate specificity in their substrates. Caspases are produced in cells as catalytically inactive zymogens and must be proteolytically processed to become active proteases during apoptosis. In normal surviving cells that have not received an apoptotic stimulus, most caspases remain inactive. Even if some caspases are aberrantly activated, their proteolytic activity can be fully inhibited by a family of evolutionarily conserved proteins called IAPs (inhibitors of apoptosis proteins) (Deveraux & Reed, Genes Dev. 13: 239-252, 1999). Each of the IAPs contains 1-3 copies of the so-called BIR (baculoviral IAP repeat) domain and directly interacts with and inhibits the enzymatic activity of mature caspases. Several distinct mammalian IAPs including XIAP, survivin, and LIVIN/ML-IAP, (Kasof and Gomes, J. Biol. Chem. 276: 3238-3246, 2001; Vucic et al. Curr. Biol. 10: 1359-1366, 2000; Ashhab et al. FEBS Lett. 495: 56-60, 2001), have been identified and they exhibit anti-apoptotic activity in cell culture (Deveraux & Reed, 1999, supra). As IAPs are expressed in most cancer cells, they may directly contribute to tumor progression and subsequent resistance to drug treatment.

In normal cells signaled to undergo apoptosis, however, the IAP-mediated inhibitory effect must be removed, a process at least in part performed by a mitochondrial protein named Smac, second mitochondria-derived activator of caspases; (Du et al. Cell 102: 33-42, 2000) or DIABLO (direct IAP binding protein with low pI; Verhagen et al. Cell 102: 43-53, 2000). Smac/DIABLO, synthesized in the cytoplasm, is targeted to the inter-membrane space of mitochondria. Upon apoptotic stimuli, Smac is released from mitochondria back into the cytosol, together with cytochrome c. Whereas cytochrome c induces multimerization of Apaf-1 to activate pro-caspase-9 and procaspase-3, Smac eliminates the inhibitory effect of multiple IAPs. Smac interacts with all IAPs that have been examined to date, including XIAP, c-IAP1, c-IAP2, ML-IAP, and survivin. Smac appears to be a regulator of apoptosis in mammals. In addition to the inhibition of caspases, overexpressed IAPs can function to bind Smac and prevent it from binding to XIAP and releasing caspases (Vucic et. al., Biochem. J. 385(Pt 1):11-20, 2005).

Smac is synthesized as a precursor molecule of 239 amino acids; the N-terminal 55 residues serve as the mitochondria targeting sequence that is removed after import. The mature form of Smac contains 184 amino acids and behaves as an oligomer in solution. Smac and various fragments of it have been proposed for use as targets for identification of therapeutic agents. The biological activity of Smac is believed to be related to binding of its N-terminal four residues to a featured surface groove in a portion of XIAP referred to as the BIR3 domain. This binding prevents XLIP from exerting its apoptosis-suppressing function in the cell. The N-terminal tetrapeptides from IAP binding proteins of the *Drosophila* pro-apoptotic proteins Hid, Grim and Reaper are believed to function in the same manner.

Commonly-owned co-pending International Application No. PCT/US02/17342, filed May 31, 2002 and incorporated herein by reference in its entirety, discloses assays for use in high throughput screening of agents that bind to a BIR domain of an IAP, thereby relieving IAP-mediated suppression of apoptosis. The assays utilize a labeled IAP-binding peptide or peptidomimetic that binds to a BIR domain of an IAP, wherein at least one measurable feature of the label changes as a function of the IAP binding compound being bound to the IAP or free in solution. The BIR domain of an IAP is contacted with the labeled IAP peptide or peptidomimetic to form a complex, and the complex is exposed to a compound to be tested for BIR binding. Displacement of the labeled IAP peptide or peptidomimetic from the complex, if any, by the test compound, is measured.

Disadvantages in the use of peptides for in vivo administration as diagnostic or therapeutic agents may include their short half-life due to proteolytic degradation of the peptide in the body, low absorption through intestinal walls, potential immunogenic reactions, as well as expense involved in peptide synthesis. It would be beneficial to prepare non-peptidic IAP binding compounds that have comparable biological activity of bioactive peptides, but possess improved pharmacological properties and are easier or less expensive to synthesize.

In connection with the Smac tetrapeptides it would be a significant advance in the art to develop IAP-binding compounds which may be used to promote apoptosis, while also having the improved properties associated with non-peptide compounds. Such compounds can be used as diagnostic and therapeutic agents in the treatment of apoptosis related conditions.

SUMMARY OF THE INVENTION

An embodiment of the present invention is a compound, or composition comprising a compound, of the general formula (2):

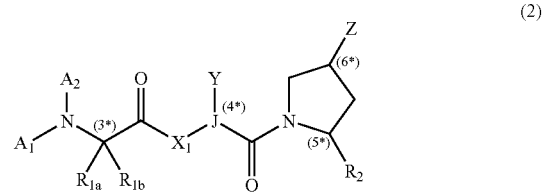

(2)

wherein: $A_1$ and $A_2$ are independently hydrogen, alkyl, aryl, or alkylaryl group, $R_{1a}$ is H or a methyl group; $R_{1b}$ is an alkyl or aryl group; $X_1$ is —O—, —S—, —CH$_2$—, or —NH— group, and J is —CH—, or —N— group, provided that when J is —N—, $X_1$ is —CH$_2$—, or —NH— group; Y is H, or an alkyl group; Z is —OH, aryloxy, alkoxy, benzyloxy, benzyloxy, amino, arylamino, alkylamino, benzylamino group; $R_2$ is a detectable label or is

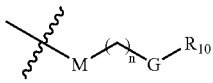

M is alkylene, alkenylene, alkynlene, heteroalkylene, heteroalkenylene, or heteroalkynlene group, G is selected from a bond, —O—; —N($R_{2d}$)— where $R_{2d}$ is H, alkyl, cycloalkyl, or aryl; or —S(O)$_m$— where m is 0, 1, or 2; and $R_{10}$ is cycloalkyl, aryl, heterocycloalkyl, heterocycloalkenyl, or heteroaryl; n is independently the integer 0, 1, 2, 3, 4, or 5.

Another embodiment of the present invention is a compound, or composition including a compound, of the general formula (3):

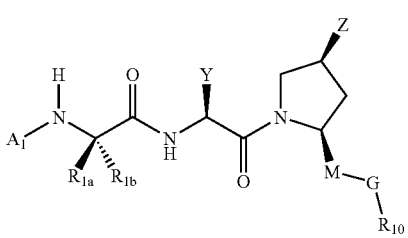

(3)

where $A_1$ is H, lower alkyl, or optionally-substituted lower alkyl group; $R_{1a}$ and $R_{1b}$ are separately H, lower alkyl, optionally-substituted lower alkyl, lower alkylene, optionally substituted lower alkylene group; or $A_1$ together with either $R_{1a}$ or $R_{1b}$ form an optionally substituted heterocycloalkyl group of 3 to 6 atoms; Y is H, an alkyl group, an alkynyl group, a cycloalkyl group of 3 to 7 carbon atoms, aryl, heteroaryl, arylalkyl, optionally-substituted versions of these groups, hydroxy substituted versions of these groups, or Y together with Z, M, G, or $R_{10}$ forms a carbocyclic ring, or a heterocyclic ring containing 1 to 5 heteroatoms, where Y is linked to Z, M, G, or $R_{10}$; Z is H, alkyl, hydroxy, amino, alkylamino, diakylamino, alkoxy, cycloalkyl, cycloalkyloxy, aryl, heteroaryl, aryloxy, or heteroaryloxy group; or Z together with Y, M, G, or $R_{10}$ form a carbocyclic ring, or a heterocyclic ring containing 1 to 5 heteroatoms, where Z is linked to Y, M, G, or $R_{10}$; M is an optionally-substituted alkyl, alkenyl, or alkynyl group; an optionally-substituted alkyl, alkenyl, or alkynyl group of 1 to 5 carbon atoms; an optionally-substituted alkylene, alkenylene, or alkynylene group; or an optionally-substituted alkylene, alkenylene, or alkynylene group of 1 to 5 carbon atoms; G is a bond, a heteroatom, —(C=O)—; —S(O)$_t$— where t=0, 1, or 2; —NR$_{18}$—; —NCOR$_{18}$—; or —NS(O)$_x$R$_{18}$— where x=0, 1, or 2, and $R_{18}$ is lower alkyl, optionally-substituted lower alkyl, or cycloalkyl or $R_{18}$ is contained within a carbocyclic, or heterocyclic ring containing 1 to 5 heteroatoms, where $R_{18}$ is linked to Z, M, or $R_{10}$; $R_{10}$ is an aryl, a heteroaryl group, a fused aryl, a fused heteroaryl group; or $R_{10}$ is any one of structures (4a), (4b), (4c) or (4d):

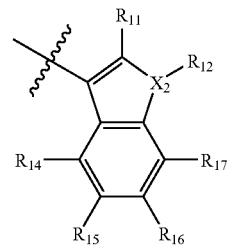

(4a)

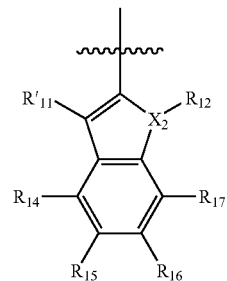

(4b)

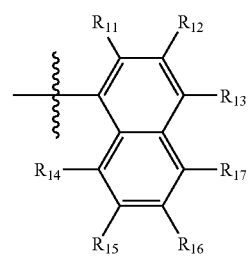

(4c)

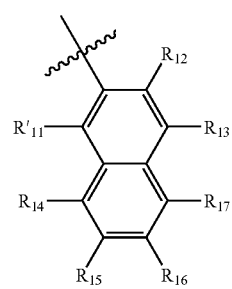

(4d)

where $X_2$ is a heteroatom and independently groups $R_{11}$, $R'_{11}$, $R_{12}$, any of $R_{13-17}$, or any of $R_{14-17}$ is H, halogen, alkyl, alkenyl, alkynyl, aryl, heteroaryl, hydroxyl, alkoxy, polyalkylether, amino, alkylamino, dialkylamino, alkyloxyalkyl, sulfonate, aryloxy or heteroaryloxy; independently $R_{11}$, $R'_{11}$, $R_{12}$, any of $R_{13-17}$, or any of $R_{14-17}$ is H, optionally-substituted alkyl, alkenyl, alkynyl, aryl, heteroaryl, hydroxyl, alkoxy, polyalkylether, amino, alkylamino, dialkylamino, alkyloxyalkyl, aryloxy, or heteroaryloxy; or independently $R_{11}$, $R'_{11}$, $R_{12}$, any of $R_{13-17}$, or any of $R_{14-17}$ is acyl or acetyl groups, carboxylate, sulfonate, sulfone, imine, or oxime groups; or groups $R_{11}$, $R'_{11}$, $R_{12}$, any of $R_{13-17}$, or any of $R_{14-17}$ is contained within a carbocyclic ring, or a heterocyclic ring containing 1 to 5 heteroatoms, and linked to groups at position Y, Z, M, G, $R_{11}$, $R'_{11}$, $R_{12}$, any of $R_{13-17}$, or any of $R_{14-17}$.

Another embodiment is compound, or a composition comprising a compound, of the general formula (5)

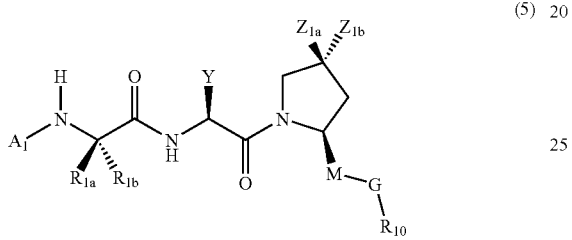

(5)

where $A_1$ is H, or lower alkyl; $R_{1a}$ is H; $R_{1b}$ is lower alkyl group; Y is an alkyl group, a cycloalkyl group of 3 to 7 carbon atoms, optionally substituted versions of these groups, hydroxy substituted versions of these groups; $Z_{1a}$ and $Z_{1b}$ are independently an H, hydroxy, alkoxy, aryloxy, or heteroaryloxy group; M is an optionally-substituted alkyl or an optionally-substituted alkylene group of 1 to 5 carbon atoms; G is a bond, a heteroatom, or —$NCOR_{18}$— and $R_{18}$ is lower alkyl, optionally-substituted lower alkyl group; $R_{10}$ is anyone of structures (4a), (4b), (4c) or (4d):

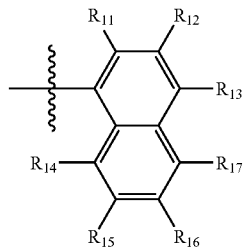

(4a)

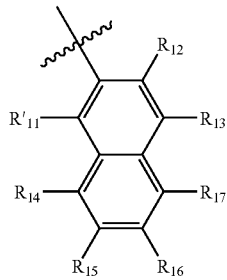

(4b)

-continued

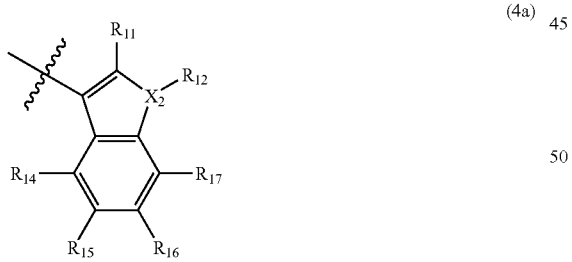

(4c)

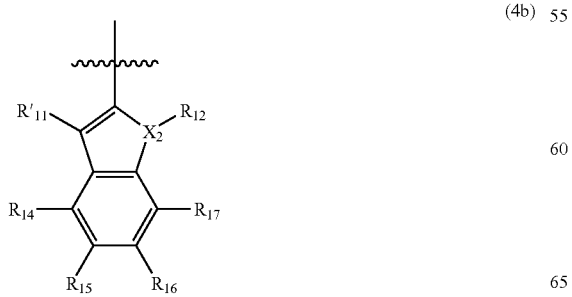

(4d)

where $X_2$ is a heteroatom and independently groups $R_{11}$, $R'_{11}$, $R_{12}$, any of $R_{13-17}$, or any of $R_{14-17}$ are H, halogen, alkyl, alkenyl, alkynyl, aryl, heteroaryl, hydroxyl, alkoxy, polyalkylether, amino, alkylamino, dialkylamino, alkyloxyalkyl, sulfonate, aryloxy or heteroaryloxy; independently $R_{11}$, $R'_{11}$, $R_{12}$, any of $R_{13-17}$, or any of $R_{14-17}$ are H, optionally-substituted alkyl, aryl, alkenyl, alkynyl, heteroaryl, hydroxyl, alkoxy, polyalkylether, amino, alkylamino, dialkylamino, alkyloxyalkyl, aryloxy, or heteroaryloxy; independently $R_{11}$, $R'_{11}$, $R_{12}$, any of $R_{13-17}$, or any of $R_{14-17}$ are acyl or acetyl groups, carboxylate, sulfonate, sulfone, imine, or oxime groups; or groups $R_{11}$, $R'_{11}$, $R_{12}$, any of $R_{13-17}$, or any of $R_{14-17}$ are contained within a carbocyclic ring, or a heterocyclic ring containing 1 to 5 heteroatoms, and linked to groups at position Y, $Z_{1a}$, $Z_{1b}$, M, G, $R_{11}$, $R'_{11}$, $R_{12}$, any of $R_{13-17}$, or any of $R_{14-17}$.

In a preferred embodiment the present invention is compound, or a composition comprising a compound, of the general formula (5)

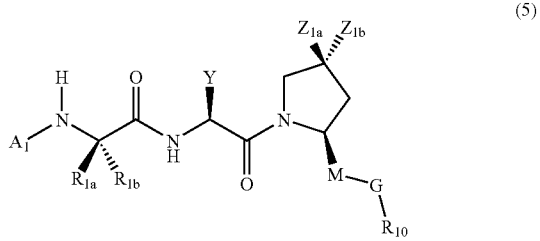

(5)

where $A_1$ is H, or lower alkyl; $R_{1a}$ is H; $R_{1b}$ is lower alkyl group; Y is an alkyl group, a cycloalkyl group of 3 to 7 carbon atoms, optionally substituted versions of these groups, hydroxy substituted versions of these groups; $Z_{1a}$ and $Z_{1b}$ are independently an H, hydroxy, alkoxy, aryloxy, or heteroaryloxy group; M is an optionally-substituted alkyl or an optionally-substituted alkylene group of 1 to 5 carbon atoms; G is a bond, a heteroatom, or —NCOR$_{18}$— and R$_{18}$ is lower alkyl, optionally-substituted lower alkyl group; R$_{10}$ is anyone of structures (4a), (4b), (4c) or (4d):

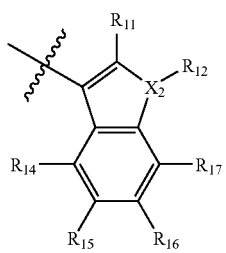

where X$_2$ is a heteroatom and independently groups R$_{11}$, R'$_{11}$, R$_{12}$, any of R$_{13-17}$, or any of R$_{14-17}$ are H, halogen, alkyl, alkenyl, alkynyl, aryl, heteroaryl, hydroxyl, alkoxy, polyalkylether, amino, alkylamino, dialkylamino, alkyloxyalkyl, sulfonate, aryloxy or heteroaryloxy; independently R$_{11}$, R'$_{11}$, R$_{12}$, any of R$_{13-17}$, or any of R$_{14-17}$ are H, optionally-substituted alkyl, aryl, alkenyl, alkynyl, heteroaryl, hydroxyl, alkoxy, polyalkylether, amino, alkylamino, dialkylamino, alkyloxyalkyl, aryloxy, or heteroaryloxy; independently R$_{11}$, R'$_{11}$, R$_{12}$, any of R$_{13-17}$, or any of R$_{14-17}$ are acyl or acetyl groups, carboxylate, sulfonate, sulfone, imine, or oxime groups; or groups R$_{11}$, R'$_{11}$, R$_{12}$, any of R$_{13-17}$, or any of R$_{14-17}$ are contained within a carbocyclic ring, or a heterocyclic ring containing 1 to 5 heteroatoms, and linked to groups at position Y, Z$_{1a}$, Z$_{1b}$, M, G, R$_{11}$, R'$_{11}$, R$_{12}$, any of R$_{13-17}$, or any of R$_{14-17}$. Even more preferably, X$_2$ is nitrogen.

Further embodiments of the present invention include molecules and compositions that may be useful to modify or regulate apoptosis in cells. These IAP binding molecules can bind to a variety of IAP's (Inhibitor of Apoptosis Proteins). These molecules may be monomers or dimers and may also include a detectable label or therapeutic moiety and can be formulated as pharmaceutical or diagnostic compositions containing these molecules. Methods for using these compounds as therapeutic and diagnostic agents are also described.

The IAP binding molecules of the present invention, which can also be referred to as IAP binding cargo molecules, can permeate, be transfected, or otherwise be actively or passively transported into cells and can be used to displace IAPs from other proteins like caspases or Smac in cells. At least a portion of the IAP binding-cargo molecule binds to a BIR domain of an IAP. The IAP binding cargo molecule may provide a therapeutic effect for a cell proliferation disorder and can include additional therapeutic, diagnostic, or other substituents in the molecule. Embodiments of the IAP binding molecules include derivatives of pyrrolidine that bind to a BIR domain of an IAP.

Embodiments of the present invention include IAP binding cargo molecules and pharmaceutically acceptable salts thereof having the general structure of formula (2):

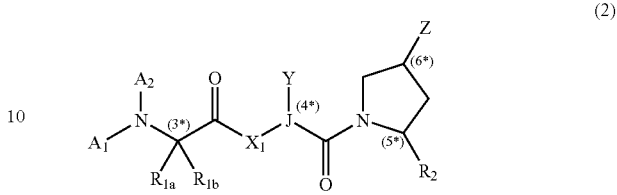

wherein: A$_1$ and A$_2$ can independently be hydrogen, alkyl, aryl, or alkylaryl group, R$_{1a}$ can be H or a methyl group; R$_{1b}$ may be an alkyl or aryl group, in some embodiments R$_{1b}$ is methyl, ethyl, n-propyl, isopropyl, or ethenyl group; X$_1$ can be —O—, —S—, —CH$_2$—, or —NH— group, and J can be —CH—, or —N— group, provided that when J is —N—, X$_1$ is —CH$_2$—, or an —NH— group; Y can be H, or an alkyl group; Z can be H, —OH, aryloxy, alkoxy, benzyloxy, amino, arylamino, alkylamino, benzylamino group, in some embodiments Z is —OH, aryloxy, alkoxy, benzyloxy, benzyloxy, amino, arylamino, alkylamino, benzylamino group; R$_2$ can include a detectable label or can be:

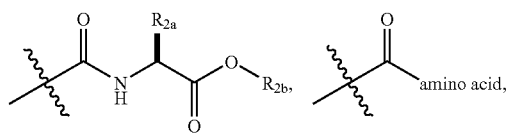

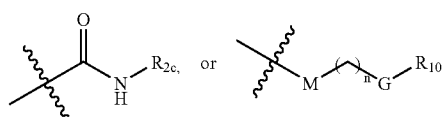

where R$_{2a}$ can be an aryl, cycloalkyl, optionally substituted aralkyl, or cycloalkylalkyl group; R$_{2b}$ can be H or alkyl group, R$_{2c}$ can be aryl, cycloalkyl, optionally substituted aralkyl, or cycloalkylalkyl, heterocycloalkyl, heterocycloalkenyl, heteroaryl, or cycloalkylaryl group. In some embodiments R$_{2c}$ is tetrahydronaphthyl or substituted tetrahydronapthyl group, most preferably R$_{2c}$ is

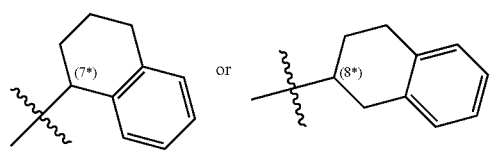

Chiral carbons (i*) for (i*=3 to 8) may independently have an (R) or (S) configuration; M can be alkylene, alkenylene, alkynlene, heteroalkylene, heteroalkenylene, heteroalkynlene group, in some embodiments M is:

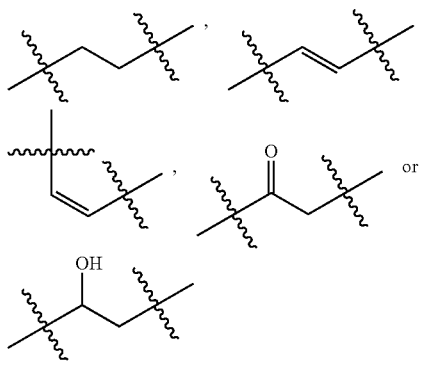

In some embodiments G can be selected from a bond (i.e., G is absent), —O—; —N($R_{2d}$)— where $R_{2d}$ can be H, alkyl, cycloalkyl, or aryl; or —S(O)$_m$— where m is 0, 1, or 2;

$R_{10}$ can be cycloalkyl, aryl, heterocycloalkyl, heterocycloalkenyl, or heteroaryl; in some embodiments $R_{10}$ is:

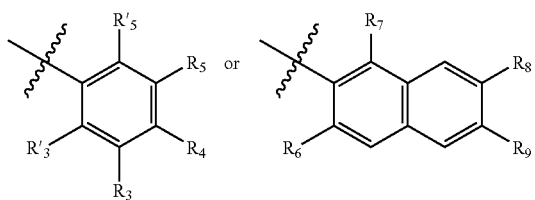

where $R_3$, $R'_3$, $R_4$, $R_5$, $R'_5$, $R_6$, $R_7$, $R_8$ and $R_9$ can each independently H, methyl, ethyl, n-propyl, isopropyl, halo, cyano, —(CH$_2$)$_p$C(═O)OH, —(CH$_2$)$_p$C(═O)O-alkyl, —(CH$_2$)$_p$C(═O)NH$_2$; n and p are integers and preferably n is independently the integer 0, 1, 2, 3, 4, or 5 and p is independently the integer 0, 1, 2, or 3; preferably at least one $R_3$, $R'_3$, $R_4$, and $R'_5$, $R_5$ or at least two of $R_6$, $R_7$, $R_8$ and $R_9$ are each independently H, methyl, ethyl, n-propyl, isopropyl, halo, or cyano; provided that when one or more of $R_3$, $R'_3$, $R'_5$, and $R_5$ is isopropyl, $R_4$ is other than isopropyl; provided that when $R_4$ is isopropyl, $R_3$, $R'_3$, $R'_5$, and $R_5$ are each independently other than isopropyl; provided that when $R_8$ is isopropyl, $R_9$ is other than isopropyl; and provided that in a therapeutic composition, (2) is not the structure where $R_2$ is

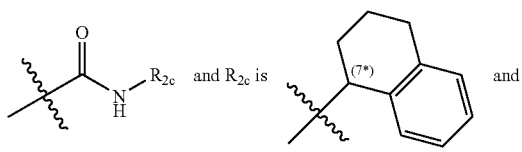

where $A_1$ is H, $A_2$ is methyl, $R_{1a}$ is H, $R_{1b}$ is methyl, $X_1$ is —NH—, J is —CH—, Y is t-butyl, Z is(—OC$_6$H$_5$) and (3*) has an (S) configuration, (4*) has an (S) configuration, (5*) has an (S) or (R) configuration, (6*) has an (S) or (R) configuration, and (7*) has an (R) configuration. Some embodiments of compounds of structure (2) have a $K_d$ as determined by the methods described, for example, in Example 1 of less than 100 micromolar, preferably less than 1 micromolar, and even more preferably less than 0.1 micromolar.

Some embodiments of the IAP binding compounds or IAP binding cargo molecules of structure (2), where $A_2$ is H, $X_1$ is —NH—, J is —CH—, and n is 0 for $R_2$, can be depicted by structure (3):

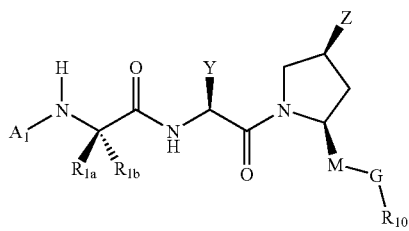

(3)

In some embodiments of compounds of structure (3), $A_1$ can be H, lower alkyl, or optionally-substituted lower alkyl group; $R_{1a}$ and $R_{1b}$ can separately be H, lower alkyl, optionally substituted lower alkyl, lower alkylene, optionally substituted lower alkylene group; or $A_1$ together with either $R_{1a}$ or $R_{1b}$ can form an optionally substituted heterocycloalkyl group of 3 to 6 atoms;

Y can be H, an alkyl group, an alkyl group of 1 to 10 carbon atoms, a branched alkyl group of 1 to 10 carbon atoms, an alkynyl group, a cycloalkyl group of 3 to 7 carbon atoms, aryl, heteroalkynyl, heteroaryl, or arylalkyl group; optionally-substituted versions of the aforementioned groups; hydroxy substituted versions of the aforementioned groups; or Y together with Z, M, G, or $R_{10}$ forms an optionally substituted carbocyclic ring, or an optionally substituted heterocyclic ring containing 1 to 5 heteroatoms, where Y is linked to Z, M, G, or $R_{10}$; preferably Y is linked to M, G, or $R_{10}$ by any number of atoms up to about 20 atoms.

Z can be H, alkyl, hydroxy, amino, alkylamino, dialkylamino, alkoxy, cycloalkyl, cycloalkyloxy, aryl, heteroaryl, aryloxy, or heteroaryloxy group; or Z together with Y, M, G, or $R_{10}$ form an optionally substituted carbocyclic ring, or an optionally substituted heterocyclic ring containing 1 to 5 heteroatoms, where Z is linked to Y, M, G, or $R_{10}$; preferably Z is linked to Y, M, G, or $R_{10}$ by any number of atoms up to about 20 atoms.

M can be an optionally substituted alkyl, alkenyl, or alkynyl group; an optionally substituted alkyl, alkenyl, or alkynyl group of 1 to 5 carbon atoms; an optionally substituted alkylene, an alkenylene, or alkynylene group; or an optionally substituted alkylene, alkenylene, or alkynylene group of 1 to 5 carbon atoms.

G can be absent (a bond), or a heteroatom including —O—; —NH—; —(C═O)—; —S(O)$_t$— where t is the integer 0, 1, or 2; —NR$_{18}$—; —NCOR$_{18}$—; or —NS(O)$_x$R$_{18}$— where x is the integer 0, 1, or 2, and $R_{18}$ can be lower alkyl, optionally-substituted lower alkyl, or cycloalkyl or $R_{18}$ is contained within an optionally substituted carbocyclic, or optionally substituted heterocyclic ring containing 1 to 5 heteroatoms, where $R_{18}$ is linked to Z, M, or $R_{10}$, preferably $R_{18}$ is linked to Z, M, or $R_{10}$, by any number of atoms up to about 20 atoms.

$R_{10}$ can be an aryl, a heteroaryl group, a fused aryl, a fused heteroaryl group or optionally substituted versions of these groups; or $R_{10}$ can be any one of structures (4a), (4b), (4c), or (4d):

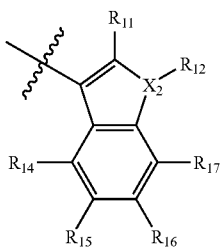

(4a)

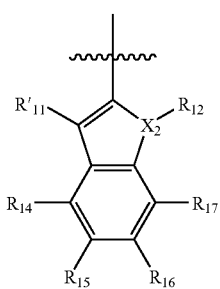

(4b)

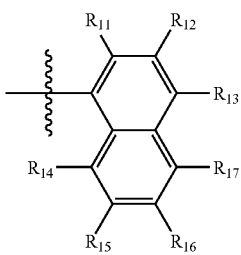

(4c)

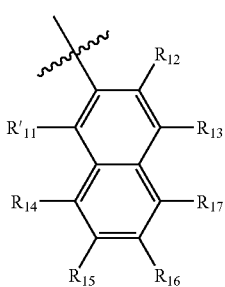

(4d)

where $X_2$ is a heteroatom in structures (4a) or (4b), or $X_2$ is a carbon-carbon bond as illustrated in structures (4c) or (4d), and independently groups $R_{11}$, $R'_{11}$, $R_{12}$, any of $R_{13-17}$, or any of $R_{14-17}$ can be H, halogen, alkyl, alkenyl, alkynyl, aryl, heteroaryl, hydroxyl, alkoxy, polyalkylether, amino, alkylamino, dialkylamino, alkyloxyalkyl, aryloxy or heteroaryloxy; or independently $R_{11}$, $R'_{11}$, $R_{12}$, any of $R_{13-17}$, or any of $R_{14-17}$ can be H, optionally-substituted alkyl, alkenyl, alkynyl, aryl, heteroaryl, hydroxyl, alkoxy, polyalkylether, amino, alkylamino, dialkylamino, alkyloxyalkyl, aryloxy, or heteroaryloxy; or independently $R_{11}$, $R'_{11}$, $R_{12}$, any of $R_{13-17}$, or any of $R_{14-17}$ can be acyl or acetyl groups, carboxylate, sulfonate, sulfone, imine, or oxime groups; or groups $R_{11}$, $R'_{11}$, $R_{12}$, any of $R_{13-17}$, or any of $R_{14-17}$ can be contained within an optionally substituted carbocyclic ring, or an optionally substituted heterocyclic ring containing 1 to 5 heteroatoms, and can be linked to groups at position Y, Z, M, G, $R_{11}$, $R'_{11}$, $R_{12}$, any of $R_{13-17}$, or any of $R_{14-17}$, preferably these groups are linked by any number of atoms up to about 20 atoms. Some embodiments of compounds of structure (3) have a $K_d$ as determined by the methods described, for example, in Example 1 of less than 100 micromolar, preferably less than 1 micromolar, and even more preferably less than 0.1 micromolar.

Some embodiments include compounds of structure (5) where:

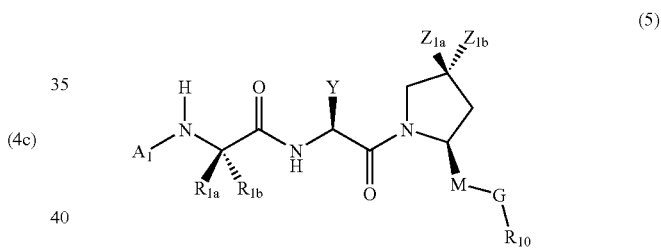

(5)

$A_1$ can be H, or lower alkyl, or $A_1$ and $R_{1b}$ together form a ring of 3-5 atoms;

$R_{1a}$ can be H; $R_{1b}$ can be a lower alkyl group, or together with $A_1$ forms a ring of 3 to 5 atoms;

Y can be an alkyl group, an alkyl group of 1 to 10 carbon atoms, a branched alkyl group of 1 to 10 carbon atoms, an alkynyl group, heteroalkynyl, a cycloalkyl group of 3 to 7 carbon atoms, optionally substituted versions of the aforementioned groups, hydroxy substituted versions of the aforementioned groups, or Y together with $Z_{1a}$, $Z_{1b}$, or $R_{10}$ forms an optionally substituted carbocyclic ring, or an optionally substituted heterocyclic ring containing 1 to 5 heteroatoms, where Y can be linked to $Z_{1a}$, $Z_{1b}$, or $R_{10}$; preferably Y is linked to $Z_{1a}$, $Z_{1b}$, or $R_{10}$ by any number of atoms up to about 20 atoms.

$Z_{1a}$ and $Z_{1b}$ can independently be an H, hydroxy, amino, alkylamino, dialkylamino, alkoxy, aryloxy, or heteroaryloxy group; or $Z_{1a}$, $Z_{1b}$, together with Y or $R_{10}$ form a carbocyclic ring, or a heterocyclic ring containing 1 to 5 heteroatoms, where $Z_{1a}$ or $Z_{1b}$, is linked to Y or $R_{10}$; preferably $Z_{1a}$ or $Z_{1b}$, is linked to Y or $R_{10}$ by any number of atoms up to about 20 atoms.

M can be an optionally-substituted alkyl or an optionally-substituted alkylene group of 1 to 5 carbon atoms.

G can be absent (a bond), or a heteroatom including —O—; —NH—; —(C=O)—; —NR$_{18}$—; —NCOR$_{18}$—; or —NS(O)$_x$R$_{18}$— where x=0, 1, or 2, and R$_{18}$ can be lower alkyl, optionally-substituted lower alkyl group.

R$_{10}$ can be aryl, a heteroaryl group, or R$_{10}$ can be anyone of structures (4a), (4b), (4c), or (4d):

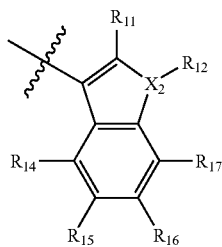
(4a)

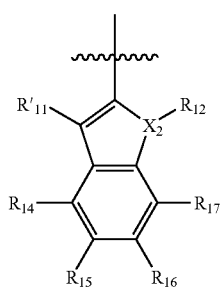
(4b)

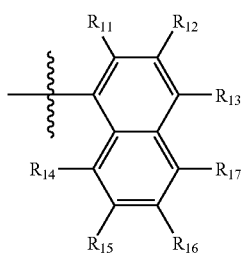
(4c)

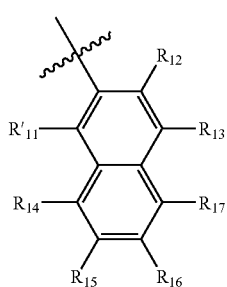
(4d)

where X$_2$ can be a heteroatom in structures (4a) or 4(b) or X$_2$ is a carbon-carbon bond as illustrated in structures (4c) or (4d), and independently groups R$_{11}$, R'$_{11}$, R$_{12}$, any of R$_{13-17}$, or any of R$_{14-17}$ can be H, halogen, alkyl, alkenyl, alkynyl, aryl, heteroaryl, hydroxyl, alkoxy, polyalkylether, amino, alkylamino, dialkylamino, alkyloxyalkyl, sulfonate, aryloxy or heteroaryloxy; or independently R$_{11}$, R'$_{11}$, R$_{12}$, any of R$_{13-17}$, or any of R$_{14-17}$ can be H, optionally-substituted alkyl, alkenyl, alkynyl, aryl, heteroaryl, hydroxyl, alkoxy, polyalkylether, amino, alkylamino, dialkylamino, alkyloxyalkyl, aryloxy, or heteroaryloxy; or independently R$_{11}$, R'$_{11}$, R$_{12}$, any of R$_{13-17}$, or any of R$_{14-17}$ can be acyl or acetyl groups, carboxylate, sulfonate, sulfone, imine, or oxime groups; or groups R$_{11}$, R'$_{11}$, R$_{12}$, any of R$_{13-17}$, or any of R$_{14-17}$ can be contained within a carbocyclic ring, or a heterocyclic ring containing 1 to 5 heteroatoms, and linked to groups at position Y, Z$_{1a}$, Z$_{1b}$, M, G, R$_{11}$, R'$_{11}$, R$_{12}$, any of R$_{13-17}$, or any of R$_{14-17}$, preferably these groups are linked by any number of atoms up to about 20 atoms. Some embodiments of compounds of structure (5) have a K$_d$ as determined by the methods described, for example, in Example 1 of less than 100 micromolar, preferably less than 1 micromolar, and even more preferably less than 0.1 micromolar.

Some embodiments include compounds of structure (5) where:

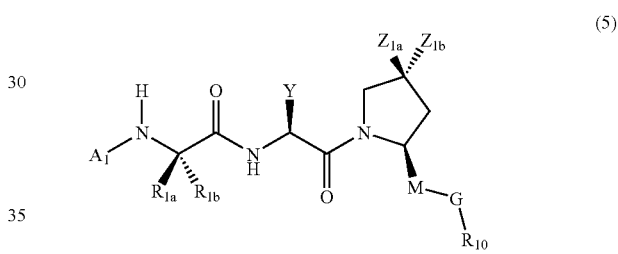
(5)

A$_1$ can be H, methyl, ethyl, or A$_1$ and R$_{1b}$ together form a ring of 3-5 atoms.

R$_{1a}$ can be H; R$_{1b}$ can be a methyl or ethyl group, or together with A$_1$ forms a ring of 3 to 5 atoms.

Y can be an alkyl group, an alkyl group of 1 to 10 carbon atoms, a branched alkyl group of 1 to 10 carbon atoms, an alkynyl group, heteroalkynyl, a cycloalkyl group of 3 to 7 carbon atoms, optionally substituted versions of the aforementioned groups; hydroxy substituted versions of the aforementioned groups; or Y together with Z$_{1a}$, Z$_{1b}$, or R$_{10}$ forms a carbocyclic ring, or a heterocyclic ring containing 1 to 5 heteroatoms, where Y is linked to Z$_{1a}$, Z$_{1b}$, or R$_{10}$; preferably Y is linked to Z$_{1a}$, Z$_{1b}$, or R$_{10}$ by any number of atoms up to about 20 atoms.

Z$_{1a}$ and Z$_{1b}$ can independently be an H, hydroxy, amino, alkylamino, diakylamino, alkoxy, aryloxy, or heteroaryloxy group; or Z$_{1a}$, Z$_{1b}$, together with Y or R$_{10}$ form a carbocyclic ring, or a heterocyclic ring containing 1 to 5 heteroatoms, where Z$_{1a}$ or Z$_{1b}$, is linked to Y or R$_{10}$; preferably Z$_{1a}$ or Z$_{1b}$, is linked to Y or R$_{10}$ by any number of atoms up to about 20 atoms.

M can be an optionally-substituted alkyl or an optionally-substituted alkylene group of 1 to 5 carbon atoms.

G can be absent (a bond), or a heteroatom including —O—; —NH—; —(C=O)—; —NR$_{18}$—; —NCOR$_{18}$—; or —NS(O)$_x$R$_{18}$— where x can be the integer 0, 1, or 2, and R$_{18}$ can be lower alkyl, optionally-substituted lower alkyl group.

$R_{10}$ can be a fused aryl, a fused heteroaryl group, or preferably $R_{10}$ is anyone of structures (4a), (4b), (4c), or (4d):

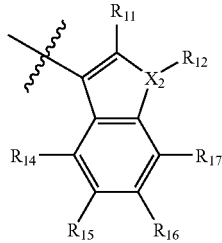
(4a)

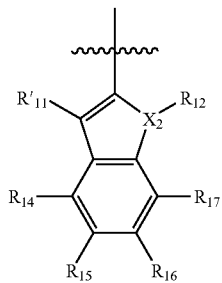
(4b)

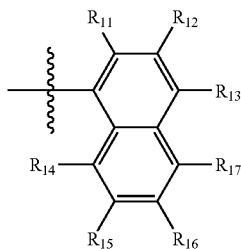
(4c)

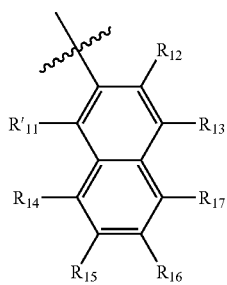
(4d)

where $X_2$ can be a heteroatom (4a) or (4b) or $X_2$ can be a carbon-carbon bond (4c) or (4d), and independently groups $R_{11}$, $R'_{11}$, $R_{12}$, any of $R_{13-17}$, or any of $R_{14-17}$ can be H, halogen, alkyl, alkenyl, alkynyl, aryl, heteroaryl, hydroxyl, alkoxy, polyalkylether, amino, alkylamino, dialkylamino, alkyloxyalkyl, sulfonate, aryloxy or heteroaryloxy; or independently $R_{11}$, $R'_{11}$, $R_{12}$, any of $R_{13-17}$, or any of $R_{14-17}$ can be H, optionally-substituted alkyl, alkenyl, alkynyl, aryl, heteroaryl, hydroxyl, alkoxy, polyalkylether, amino, alkylamino, dialkylamino, alkyloxyalkyl, aryloxy, or heteroaryloxy; or independently $R_{11}$, $R'_{11}$, $R_{12}$, any of $R_{13-17}$, or any of $R_{14-17}$ can be acyl or acetyl groups, carboxylate, sulfonate, sulfone, imine, or oxime groups; or groups $R_{11}$, $R'_{11}$, $R_{12}$, any of $R_{13-17}$, or any of $R_{14-17}$ can be contained within a carbocyclic ring, or a heterocyclic ring containing 1 to 5 heteroatoms, and linked to groups at position Y, $Z_{1a}$, $Z_{1b}$, M, G, $R_{11}$, $R'_{11}$, $R_{12}$, any of $R_{13-17}$, or any of $R_{14-17}$, preferably these groups are linked by any number of atoms up to about 20 atoms.

Some embodiments include compounds of structure (5) where:

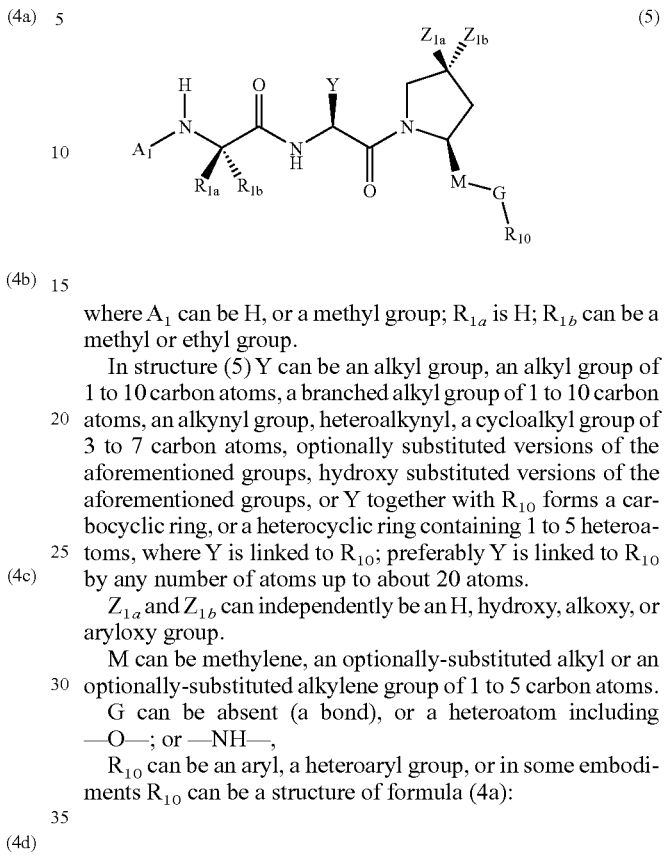
(5)

where $A_1$ can be H, or a methyl group; $R_{1a}$ is H; $R_{1b}$ can be a methyl or ethyl group.

In structure (5) Y can be an alkyl group, an alkyl group of 1 to 10 carbon atoms, a branched alkyl group of 1 to 10 carbon atoms, an alkynyl group, heteroalkynyl, a cycloalkyl group of 3 to 7 carbon atoms, optionally substituted versions of the aforementioned groups, hydroxy substituted versions of the aforementioned groups, or Y together with $R_{10}$ forms a carbocyclic ring, or a heterocyclic ring containing 1 to 5 heteroatoms, where Y is linked to $R_{10}$; preferably Y is linked to $R_{10}$ by any number of atoms up to about 20 atoms.

$Z_{1a}$ and $Z_{1b}$ can independently be an H, hydroxy, alkoxy, or aryloxy group.

M can be methylene, an optionally-substituted alkyl or an optionally-substituted alkylene group of 1 to 5 carbon atoms.

G can be absent (a bond), or a heteroatom including —O—; or —NH—, $R_{10}$ can be an aryl, a heteroaryl group, or in some embodiments $R_{10}$ can be a structure of formula (4a):

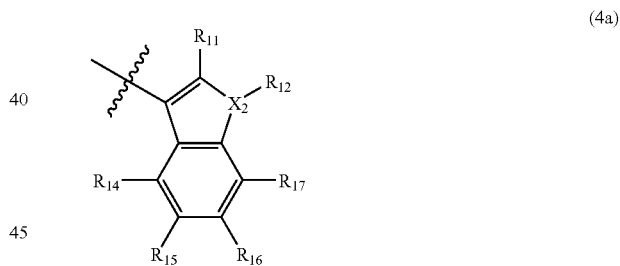
(4a)

where $X_2$ is a heteroatom and independently groups $R_{11}$, $R_{12}$, or any of $R_{14-17}$ can be H, or optional substituents including halogen, alkyl, aryl, alkenyl, alkynyl, heteroaryl, hydroxyl, alkoxy, polyalkylether, amino, alkylamino, dialkylamino, alkyloxyalkyl, sulfonate, aryloxy or heteroaryloxy; or independently $R_{11}$, $R_{12}$, or any of $R_{14-17}$ can be H, optionally-substituted alkyl, alkenyl, alkynyl, aryl, heteroaryl, hydroxyl, alkoxy, polyalkylether, amino, alkylamino, dialkylamino, alkyloxyalkyl, aryloxy, or heteroaryloxy; or independently $R_{11}$, $R_{12}$, or any of $R_{14-17}$ can be acyl or acetyl groups, carboxylate, sulfonate, sulfone, imine, or oxime groups; or groups $R_{11}$, $R_{12}$, or any of $R_{14-17}$ can be contained within a carbocyclic ring, or a heterocyclic ring containing 1 to 5 heteroatoms, and linked to groups at position Y, $Z_{1a}$, $Z_{1b}$, M, G, $R_{11}$, $R_{12}$, or any of $R_{14-17}$, preferably these groups are linked by any number of atoms up to about 20 atoms.

IAP binding compounds or IAP binding cargo molecules in various embodiments of formula (2), (3), or (5) may be used in the manufacture of a medicament for the therapeutic and/or prophylactic treatment of a cancer or cellular proliferation condition (including developmental disorders, cancer, autoimmune diseases, as well as neuro-degenerative disorders). The IAP binding compounds or IAP binding cargo molecules in various embodiments of formula (2), (3), or (5) can be used in the preparation of a drug for treating cancer or a cellular proliferation disorder condition in a ready to use form. The drug can be administered to a patient for treating or preventing cancer or a cellular proliferation disorder. In ready to use form refers to the compounds being presentable for sale and may include the compounds in a tablet, liquid, or other form for administration, suitable packaging, instructions, and other items.

One embodiment of the invention is a method of treating cells or tissue that can include administering to cells having a proliferation disorder, for example HeLa cells known to overexpress IAP (other cells may include but are not limited to those with developmental disorders, cancer, autoimmune diseases, as well as neuro-degenerative disorders), an amount of the IAP binding compounds or IAP binding cargo molecules in various embodiments of formula (2), (3), or (5) that is effective to reduce or eliminate the cellular proliferation disorder in the sample of cells or tissue.

A further embodiment of the present invention is a method of treating disorders associated with cell proliferation, including, but not limited to proliferative disorders and diseases. Such methods include administration of the compounds of the present invention alone or in combination with other active agents, including pharmaceuticals and chemotherapeutic agents. For example, the dimmers of IAP binding compounds of the present invention may be administered alone or in combination with chemotherapeutic agents as is disclosed in commonly owned U.S. Provisional Application No. 60/692,111, which is incorporated herein by reference in its entirety.

The foregoing IAP binding compounds, as well as pharmaceutically acceptable salts and solvates thereof, may be formulated as pharmaceutical compositions or as diagnostic agents, or both. These pharmaceutical compositions and diagnostic agents may be used for treatment and detection of cell proliferative disorders, as well as in screening assays for the discovery and development of additional diagnostic and therapeutic agents for modifying cell proliferation and detecting cell proliferative disorders.

The present invention includes an assay for use in high throughput screening or rational drug design of IAP binding compounds that can, like the Smac tetrapeptide or its homologs in other species, bind to a BIR domain of an IAP thereby modifying, and preferably relieving IAP-mediated suppression of apoptosis. The binding of test compounds can be used in the design of IAP binding compounds and IAP binding cargo molecules for the identification, prevention, and treatment of diseases related to cell proliferation. The IAP binding cargo molecule or compounds in embodiments of the present invention can bind to proteins such as through the BIR domain of an IAP. In some embodiments, the IAP binding molecule interacts with the BIR3 domain of the protein XIAP or BIR2 domain of DIAP1. The IAP binding molecule can interact with the protein through a specific binding groove of the BIR domain.

The assay includes the steps of providing a labeled IAP binding compound or an IAP binding-cargo molecule of structure (2), (3), or (5), that binds to the appropriate BIR domain of the IAP, wherein preferably at least one measurable feature of the labeled IAP binding compound changes as a function of the labeled IAP binding compound being bound to the IAP or free in solution. The assay may further include contacting the BIR domain of an IAP with the labeled IAP binding compound under conditions enabling binding of the labeled IAP binding compound with the BIR domain, thereby forming a labeled BIR-bound IAP binding compound complex having the measurable feature. The labeled BIR-bound IAP binding compound complex may be contacted with other peptides, IAP binding compounds, or test compounds being developed, to measure the binding of the peptides, IAP binding compounds, or test compound for the BIR domain by measuring the displacement of the labeled IAP binding compound from the labeled BIR-bound IAP binding compound complex. Displacement of the labeled IAP binding compound from the labeled BIR-bound IAP binding compound complex by the peptides, IAP binding compounds, or test compound can be determined by measuring the change in the measurable feature of the labeled IAP binding compound, thereby determining if the test compound is capable of binding to the BIR domain of the IAP and the strength of the interaction.

The present invention relates to the treatment of cell proliferation conditions and diseases and more specifically conditions where the activity of IAP in cells, tissues or an individual is abnormal. The invention features molecules that are IAP binding compounds of structure (2), (3), or (5), that bind to IAPs such as but not limited to XIAP, c-IAP1, c-IAP2, ML-IAP and surviving in cells. The mimetic molecules optionally include an integral or linked cargo portion that can include a therapeutic or diagnostic functionality. The IAP binding compound molecules may be administered to cells, a tissue, or a patient in need of treatment or detection for a cell proliferation condition or disease. The need for treatment can be identified by contacting cells or a tissue, preferably from the patient, with an IAP binding molecule having a detectable label or cargo that changes when the molecule binds to an IAP in the tissue or cells. The binding of the IAP binding compound molecule with the IAP in the cells can be used to modify a cell proliferation condition or disease or it may be combined with other therapeutic treatments such as radiation therapy. The activity of IAP in the cells or the progress of a course of treatment for a cell proliferation condition or disease may be measured with an IAP binding cargo molecule having a detectable label.

According to one aspect of the invention, a method of selectively identifying neoplastic or cancer cells in a mixed population of cells is provided. The method includes contacting the mixed cell population with a cell permeable IAP-binding cargo molecule of structure (2), (3), or (5), under conditions enabling the IAP-binding cargo molecule to bind a protein like an IAP within the neoplastic cells, thereby selectively identifying the neoplastic cells by a detectable property of the IAP binding cargo molecule, and in some embodiments a change in a detectable property of the IAP binding cargo molecule upon complexation with IAP in the neoplastic cells. The cells may be cultured cells or primary cells from a patient (human or animal). Alternatively, the cells may be present within the patient, and the contacting accomplished by introducing the IAP-binding cargo molecule into the patient.

In an embodiment of the IAP-binding cargo molecule, the cargo portion of the molecule comprises a dye label. In other embodiments, the cargo portion of the molecule can be, but is not limited to, an NMR-active nucleus or an MRI contrast agent. The selective identification of tissues or cells having IAP is performed through nuclear magnetic resonance or magnetic resonance imaging. Alternatively, the labeled IAP-binding cargo molecule comprises a radioisotope and the selective identification is performed through positron emission tomography.

Another aspect of the invention features a method of selectively damaging or inducing apoptosis in neoplastic cells by killing some or all of the neoplastic cells in a mixed population of cells. The method includes contacting a sample of the mixed cell population with an IAP-binding cargo molecule of formula (2), or (3), or (5). The IAP binding portion of the molecule or the cargo portion of the molecule can include a moiety or substituent that is directly or indirectly toxic to cells such as but not limited to a radioisotope or a photosensitizing agent. The IAP binding portion of the molecule binds to a protein like an IAP within the neoplastic cells, where the toxic moiety of the IAP-binding cargo molecule directly or indirectly exerts its toxic effect, thereby damaging or killing at least a portion the neoplastic cells in a mixed population of cells.

Another embodiment of the present invention is a composition that includes cells and an IAP-binding cargo molecule. The IAP binding cargo molecule binds to an IAP protein, such as XIAP, c-IAP1, c-IAP2, ML-IAP, or survivin, preferably it binds to a BIR surface groove of an IAP protein. In some embodiments the IAP binding molecule binds to the BIR3 surface groove of an XIAP protein. The IAP binding cargo molecule of structure (2), (3), or (5), can permeate or be transfected into the cells and can, for example, be used to displace one or more IAP proteins from caspases in the cells or displace a protein like Smac sequestered by IAPs. The IAP binding cargo molecule can have a detectable property which is modified upon chemical, physical, or a combination of these interactions, of the IAP binding molecule with the IAP protein in the cells. This composition is useful as a control for monitoring the presence of IAP in the cells undergoing treatment or for use as a standard in the detection of abnormal IAP levels in a sample of cells. The detectable property may be the emission of light by the cargo portion of the molecule which changes when the IAP bonding portion of the molecule binds to an IAP protein.

The IAP binding compounds or IAP binding cargo molecules of structure (2), (3), or (5) in embodiments of the invention may be characterized by having an IAP binding constant $K_d$. In some embodiments $K_d$ is less than about 10 µM, in other embodiments $K_d$ is less than about 1 µM, and in still other embodiments $K_d$ is less than about 0.1 µM as determined by the methods described in Example 1 or equivalents of these methods known to those skilled in the art. Molecules of formula (2), (3), or (5) having a $K_d$ of less than about 10 µM can be used in an in vitro binding assay with the BIR domain of an IAP and in some embodiments the BIR3 domain of XIAP. The IAP binding cargo molecule, and preferably the cargo portion of the molecule includes but is not limited to a fluorogenic group, a radioisotope, or other chromogenic group. In further embodiments the IAP binding cargo molecule may include another peptide or peptidomimetic unit (e.g., dimer). The IAP binding cargo molecule may include an NMR-active nucleus or an MRI contrast agent and the selective identification of the cargo portion of the molecule performed through nuclear magnetic resonance or magnetic resonance imaging. The one or more cells in the composition may include but are not limited to cells from a bodily fluid, tissue, tumor, fibroid, neoplastic cells, stem cells, nervous system cells or any combination of these from an animal, a mammal, or a human. The cells in the composition may be taken from tissue suspected of exhibiting an abnormal level of IAP based upon physical examination, motor skill tests, or detection by palpation of a lump in a part of the body. The composition may include one or more pharmaceutically acceptable excipients.

Another embodiment of the present invention is a method of identifying IAP in cells that includes monitoring a mixture of one or more IAP binding cargo molecules comprising structure (2), (3), or (5), or dimers thereof, with one or more sample cells for the presence of a detectable label from an IAP binding cargo molecule or a change in a detectable property of one or more of the IAP binding cargo molecules in the mixture. Preferably the detectable property of the IAP binding cargo molecule changes upon formation of a complex between the IAP binding cargo molecule and the BIR domain of an IAP protein, the IAPs may include but are not limited to XIAP, c-IAP1, c-IAP2, ML-IAP, or survivin in the sample cells. In the sample, the IAP may be bound to a caspase, other proteins like Smac, or combinations of these within the cell. Monitoring may be performed on cells and an IAP binding cargo molecule in a fluid sample, a flowing fluid, or fluids following purification. This invention may be used to detect abnormal expression, over or under expression, of IAP in cells and the indication of abnormal expression used to begin a course of treatment of the cells. Preferably the IAP binding cargo molecule is used to detect overexpression of IAPs in cells. The method may further include the act of comparing a change in a detectable property of one or more IAP binding cargo molecules mixed with one or more control cells to the detectable change in the property of the one or more IAP binding cargo molecules mixed with one or more sample cells. The comparison may be related to the amount or activity of IAP in the sample cells. The method may include the act of combining one or more IAP binding cargo molecules with one or more cells including but not limited to sample cells, control cells, or various combination of these cells. The monitoring may use the absorption or emission of radiant energy by the mixture of IAP binding cargo molecules and the cells, including but not limited to magnetic resonance, fluorescence, chemiluminesence, magnetic resonance imaging, and positron emission tomography. Preferably the change in the detectable property of one or more of the IAP binding cargo molecules in the mixture chemically, and or physically binding to the IAP in the cells is a change in the intensity of fluorescent emission of the IAP binding molecule. In some embodiments, a change occurs in the fluorescent emission of one or more IAP binding cargo molecules capable of displacing IAP from caspases or Smac from IAPs in the sample cells.

A method of treating cells of the present invention includes identifying the expression of IAP in cells and administering an amount of a cell permeable IAP-binding cargo molecule or other therapeutic to the cells to modify the activity of IAP in the cells. The IAP-binding cargo molecule may be formulated with a pharmaceutically acceptable excipient. For example, following identification of abnormal levels of IAP in a sample of cells, (optionally by comparison to a control sample of cells), purified Smac, an IAP binding compound, or an IAP binding cargo molecule, may be added to the cells to induce apoptosis. This invention can be used to identify cells in need of treatment, treat the cells, and monitor the progress of the treatment of the cells having the abnormal IAP levels. The act of identifying cells having abnormal IAP expression includes monitoring a mixture of one or more IAP binding cargo molecules with one or more sample cells for a change in a detectable property of one or more of the IAP binding cargo molecules. The detectable property changes upon formation of a complex between the IAP binding molecule and IAP in the sample cells.

Another embodiment of the present invention is an article or kit that includes packaging material containing a composition of IAP binding compound or an IAP binding cargo molecule of formula (2), (3), or (5) or a dimer thereof. The packaging material has a label that indicates how the IAP binding cargo composition can be used for administration, treatment, or detecting levels of IAP in a sample of cells. The label may further indicate how the IAP binding cargo molecule or another IAP binding cargo molecule included in a pharmaceutical composition can be used to treat cells where an abnormal level of IAP expression is determined.

An embodiment of the present invention is a method of selectively identifying neoplastic cells in a mixed population of cells. In the method a sample of the mixed cell population is contacted with one or more IAP-binding cargo molecules of formula (2), (3), or (5) or dimers thereof under conditions enabling the IAP-binding cargo molecule to bind IAP within the neoplastic cells and thereby selectively identifying the neoplastic cells. The cells may include but are not limited to cultured cells, cells that are removed from a subject by biopsy, or cells from a fluid. The contacting may be performed by introducing the labeled IAP-binding cargo molecule into a tissue sample or a tissue in a living subject possessing or suspected of possessing the neoplastic cells. The IAP-binding cargo molecule can have a dye label cargo portion and preferably the dye is a fluorogenic dye. The labeled IAP-binding cargo molecule may have an NMR-active nucleus or a contrast agent and the selective identification performed through nuclear magnetic resonance or magnetic resonance imaging. The labeled IAP-binding cargo molecule may have a cargo portion of the molecule that is a radioisotope and where the selective identification performed through positron emission tomography. The IAP binding cargo molecule may be formulated with pharmaceutically acceptable excipients and optionally other therapeutic agents for modifying apoptosis in the sample of cells.

Another embodiment of the present invention is a method of selectively damaging or killing neoplastic cells in a mixed population of normal and neoplastic cells. The method includes contacting a sample of the mixed cell population with a cell permeable IAP-binding cargo molecule of formula (2), (3), or (5) or dimers thereof including an agent that is directly or indirectly toxic to cells, preferably the cargo portion of the molecule is an agent that is directly or indirectly toxic to cells. Under conditions enabling the IAP-binding cargo molecule to bind IAP within the neoplastic cells, the agent directly or indirectly exerts its toxic effect, thereby damaging or killing at least a portion the neoplastic cells. The method may use a toxic agent that is a radioisotope. The method may use a photosensitizing toxic agent and the selective damaging or killing is performed by exposing the cell population to light.

DETAILED DESCRIPTION OF THE INVENTION

Before the present compositions and methods are described, it is to be understood that this invention is not limited to the particular molecules, compositions, methodologies or protocols described, as these may vary. It is also to be understood that the terminology used in the description is for the purpose of describing the particular versions or embodiments only, and is not intended to limit the scope of the present invention which will be limited only by the appended claims.

It must also be noted that as used herein and in the appended claims, the singular forms "a", "an", and "the" include plural reference unless the context clearly dictates otherwise. Thus, for example, reference to a "cell" is a reference to one or more cells and equivalents thereof known to those skilled in the art, and so forth. Unless defined otherwise, all technical and scientific terms used herein have the same meanings as commonly understood by one of ordinary skill in the art. Although any methods and materials similar or equivalent to those described herein can be used in the practice or testing of embodiments of the present invention, the embodiment's methods, devices, and materials are now described. All publications mentioned herein are incorporated by reference. Nothing herein is to be construed as an admission that the invention is not entitled to antedate such disclosure by virtue of prior invention.

"Optional" or "optionally" means that the subsequently described event or circumstance may or may not occur, and that the description includes instances where the event occurs and instances where it does not.

The IAP binding molecules of the present invention and pharmaceutical compositions containing these compounds can bind to IAP's (Inhibitor of Apoptosis Proteins) such as but not limited to XIAP, c-IAP1, c-IAP2, survin, and LIVIN/ML-IAP. These compounds may include diagnostic or therapeutic moieties or substituents as part of the binding portion of the molecule or linked to the binding portion of the molecule. The IAP binding cargo molecules may be arbitrarily divided to include an IAP binding portion and a cargo portion. The IAP binding portion of the molecule interacts with an IAP protein, preferably the BIR domain of an IAP protein, and may be a monomer or dimer. In some embodiments the IAP binding portion of the molecule interacts with the BIR3 surface groove of XIAP. The cargo portion of the molecule may be part of the backbone or IAP binding portion of the molecule or the cargo portion may be chemically bonded to the IAP binding portion of the molecule. The cargo portion of the molecule may include but is not limited to structures, moieties, and substituents for imaging, therapeutics, probes, labels, or markers. The cargo portion and IAP binding portion of the molecule may be connected by a chemical bond to the IAP binding portion including but not limited to amide, ester, or disulfide bonds, chelation, or by a linking group such as diaminobutane or ethylene glycol and its oligomers where it is desirable to separate the IAP binding portion of the molecule from the cargo portion of the molecule. One or more atoms in any portion of the IAP binding cargo molecule may be a radioisotope and used for detection or treatment. In other embodiments, the cargo portion may constitute a second monomer, thereby forming a dimer molecule, via a linking group. The binding portion of the IAP binding compound confers IAP target protein specificity to the molecule and the cargo portion can provide a functional group to the molecule for monitoring or evaluating the location of the molecule or providing a therapeutic to that location within a cell sample or a tissue in a mammal. The IAP binding compounds may be used to displace sequestered proteins in cells, for example caspase-3, 7 or 9 or Smac interacting with an IAP, so that the released protein can be used to promote apoptosis within the cell. Where the cargo portion of the molecule is linked to the IAP binding portion, the cargo portion may be bonded or chemically linked to any portion of the IAP binding portion of the molecule so that it does not adversely affect IAP binding, cell permeance or transfection into cells. While chemical interaction between the IAP binding portion and the cargo portion of the molecule may occur, the molecule is made so that the molecule's cell permeance, its IAP binding property, and function of the cargo portion are not adversely affected by their combination. The suitability of any IAP binding cargo molecule made by the method disclosed may be tested against fluorescently labeled peptide [AbuRPF-K(5-Fam)-NH$_2$] in cells such but not limited to renal cell carcinoma, non-small cell lung cancer, HeLa cells, or others known to overexpress IAP, or other cells having a proliferation disorder. The IAP binding molecules of the present invention are capable of permeating cells of interest, binding to IAP in the cells, and optionally delivering the cargo to the cells.

Embodiments of compounds of structure (2), (3), (5) include 2-substituted pyrrolidine-1-carbonyls, or 2, 4-independently substituted pyrrolidine-1-carbonyls that have a K$_d$ as determined by methods described, for example, in Example 1 of less than 100 micromolar, preferably less than 1 micromolar, and even more preferably less than 0.1 micromolar.

The pharmaceutically active compounds of the invention are sometimes referred to herein as drugs, to highlight their therapeutic utility in promoting apoptosis by binding IAPs. However, another embodiment of the invention utilizes the compounds as diagnostic agents, for detection of IAP in vitro, in situ or in vivo, or for IAP binding assays. In these embodiments, the compounds of the invention are detectably labeled, for example, with a fluorophore. Another embodiment of the invention utilizes the compounds as targeting agents, i.e., by incorporating into their structure tumor cell-killing or other anti-tumor or therapeutic agents, such as radionuclides. Accordingly, drugs refer to pharmaceutically/biologically active (i.e., IAP-binding) compounds of the invention, for use as therapeutic, prophylactic, or diagnostic agents.

The term heteroatom refers to nitrogen, oxygen, sulfur, other atoms or groups where the nitrogen, sulfur and other atoms may optionally be oxidized, and the nitrogen may optionally be quaternized. Any heteroatom with unsatisfied valences is assumed to have hydrogen atoms sufficient to satisfy the valences. In some embodiments, for example where the heteroatom is nitrogen and includes a hydrogen or other group to satisfy the valance of the nitrogen atom, replacement of the nitrogen in a similar structure by another heteroatom, for example by oxygen, will result in the hydrogen or group previously bonded to the nitrogen to be absent. The term heteroatom may include but is not limited to for example —O—, —S—, —S(O)—, —S(O)$_2$—, —N—, —N(H)—, and —N(C$_1$-C$_6$ alkyl).

The term alkyl refers to a saturated straight, branched, or cyclic hydrocarbon having from about 1 to about 30 carbon atoms (and all combinations and subcombinations of ranges and specific numbers of carbon atoms therein). Lower alkyl group refers to a saturated straight, branched, or cyclic hydrocarbon having group of 1 to 10 carbon atoms, more preferably 1 to 5 carbon atoms and all combinations and subcombinations of ranges and specific numbers of carbon atoms therein. Alkyl groups include, but are not limited to methyl, ethyl, n-propyl, isopropyl, n-butyl, isobutyl, t-butyl, n-pentyl, cyclopropyl, methylcyclopropyl, cyclopentyl, isopentyl, neopentyl, n-hexyl, isohexyl, cyclohexyl, cyclooctyl, adamantyl, 3-methylpentyl, 2,2-dimethylbutyl, and 2,3-dimethylbutyl.

The term substituted alkyl refers to a saturated straight, branched, or cyclic hydrocarbon having from about 1 to about 30 carbon atoms (and all combinations and subcombinations of ranges and specific numbers of carbon atoms therein) having from 1 to 5 substituents. Substituted lower alkyl group refers to a saturated straight, branched, or cyclic hydrocarbon of 1 to 10 carbon atoms, more preferably 1 to 5 carbon atoms (and all combinations and subcombinations of ranges and specific numbers of carbon atoms therein) having from 1 to 5 substituents. Substituted alkyl radicals and substituted lower alkyl groups can have from 1 to 5 substituents including but not limited to alkoxy, substituted alkoxy, acylamino, thiocarbonylamino, acyloxy, amino, amidino, alkylamidino, amidalkyl (such as —CH$_2$C(=O)NH$_2$ or —CH$_2$CH$_2$C(=O)NH$_2$), thioamidino, acylalkylamino, cyano, halogen atoms (F, Cl, Br, I) to give halogenated or partially halogenated alkyl groups, including but not limited to —CF$_3$, —CF$_2$CF$_3$, —CH$_2$CF$_2$Cl and the like, hydroxy, nitro, carboxyl, carboxylalkyl, carboxylheterocyclic, carboxyl-substituted heterocyclic, cycloalkyl, guanidino, heteroaryl, aryl, heterocyclic, alkylamino, dialkylamino, or optionally substituted versions of any of the aforementioned groups.

The term alkylene radical as used herein includes reference to a di-functional saturated branched or unbranched hydrocarbon radical containing from 1 to 30 carbon atoms, and includes, for example, methylene (—CH$_2$—), ethylene (—CH$_2$CH$_2$—), propylene (—CH$_2$CH$_2$CH$_2$—), 2-methylpropylene (—CH$_2$CH(CH$_3$)CH$_2$—), hexylene (—(CH$_2$)$_6$—), and the like. Lower alkylene includes an alkylene group of 1 to 10, more preferably 1 to 5, carbon atoms.

Substituted alkylene radicals includes reference to a di-functional saturated branched or unbranched alkylene radical or group having 1-30 carbon atoms and having from 1 to 5 substituents. Lower substituted alkylene radicals refer to a substituted alkylene radical group, having 1-10 carbon atoms, preferably having 1-5 carbon atoms, and having from 1 to 5 substituents. Substituents can include but are not limited to those for the alkyl groups.

The term alkenyl radical as used herein includes reference to a branched, cyclic hydrocarbon, or unbranched hydrocarbon radical of 2 to 30 carbon atoms containing at least one carbon-carbon double bond, such as ethenyl, n-propenyl, isopropenyl, n-butenyl, isobutenyl, t-butenyl, octenyl, decenyl, tetradecenyl, hexadecenyl, eicosenyl, tetracosenyl and the like. The term lower alkenyl includes an alkenyl group of 2 to 10 carbon atoms, preferably 2 to 5 carbon atoms, containing at least one carbon-carbon double bond. The one or more carbon-carbon double bonds may independently have a cis or trans configuration. Substituted alkenyl radical refers to an alkenyl radical or lower alkenyl group having from 1 to 5 substituents that can include but are not limited to those for the alkyl groups.

The term alkenylene radical includes reference to a difunctional branched or unbranched hydrocarbon radical or group containing from 2 to 30 carbon atoms and at least one carbon-carbon double bond. "Lower alkenylene" includes an alkenylene group of 2 to 10, more preferably 2 to 5, carbon atoms, containing one carbon-carbon double bond. Substituted alkenylene radical refers to an alkenylene radical or lower alkenyl group having from 1 to 5 substituents that can include but are not limited to those for the alkyl groups.

The term alkynyl radical or group refers to straight or branched chain hydrocarbon radical having 2 to 12 carbon atoms and at least one triple bond, some embodiments include alkynyl groups of 2 to 6 carbon atoms that have one triple bond. A substituted alkynyl will contain one, two, or three substituents as defined for substituted alkyl groups. Alkynylene includes reference to a difunctional branched or unbranched hydrocarbon chain containing from 2 to 12 carbon atoms and at least one carbon-carbon triple bond; some embodiments include an alkynylene groups of 2 to 6 carbon atoms with one triple bond. A substituted alkynylene will contain one, two, or three substituents as defined for substituted alkyl groups.

As used herein, "halo" or halogen refers to any halogen, such as I, Br, Cl or F. As used herein, "cyano" refers to the —C≡N group.

The term aryl radical or group refers to an optionally substituted, mono or bicyclic aromatic ring radicals having from about 5 to about 14 carbon atoms (and all combinations and subcombinations of ranges and specific numbers of carbon atoms therein), with from about 6 to about 10 carbons being preferred. Non-limiting examples or aryl groups include, for example, phenyl and naphthyl. A substituted aryl group will contain one or more substituents as defined for substituted alkyl groups.

Aralkyl radical refers to alkyl radicals bearing an aryl substituent and have from about 6 to about 20 carbon atoms (and all combinations and subcombinations of ranges and specific numbers of carbon atoms therein), with from about 6 to about 12 carbon atoms being preferred. Aralkyl groups can be optionally substituted. Non-limiting examples include, for example, benzyl, naphthylmethyl, diphenylmethyl, triphenylmethyl, phenylethyl, and diphenylethyl. A substituted arylalkyl group will contain one or more substituents on the aryl or alkyl group as defined for substituted alkyl groups.

Cycloalkylaryl radical or group refers to a cycloalkyl radical fused to an aryl group, including all combinations of independently substituted alkyl cycloalkylaryls, the cycloalkyl and aryl group having two atoms in common. Examples of fused cycloalkylaryl groups used in compounds of the present invention may include 1-indanyl, 2-indanyl, 1-(1,2,3,4-tetrahydronaphthyl), and the like. Tetrahydronaphthyl more specifically refers to those univalent radicals or groups derived from fused polycyclic hydrocarbons including all combinations of independently substituted alkyl tetrahydronaphthyls. These radicals may have a point of attachment at ($C_1$) or equivalently ($C_4$) in structure (11), or position labeled ($C_2$) and equivalently ($C_3$) in structure (11a). The chiral carbon atoms $C_{1-4}$ in tetrahydronaphthlene and its alkyl substituted derivatives may have either an (R) or (S) configuration.

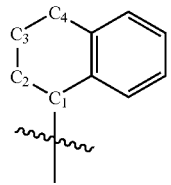

(11)

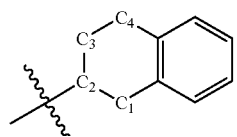

(11a)

Cycloalkyl radical or group more specifically includes reference to a monovalent saturated carbocyclic alkyl radical consisting of one or more rings in their structures and having from about 3 to about 14 carbon atoms (and all combinations and subcombinations of ranges and specific numbers of carbon atoms therein), with from about 3 to about 7 carbon atoms being preferred. Multi-ring structures may be bridged or fused ring structures. The rings can optionally be substituted with one or more of the substituents for the alkyl groups. Examples of cycloalkyl groups include, but are not limited to, cyclopropyl, cyclobutyl, cyclopentyl, cyclohexyl, cyclooctyl, and adamantyl. A substituted cycloalkyl group will contain one or more substituents as defined for substituted alkyl groups.

Cycloalkylalkyl radical more specifically refers to alkyl radicals bearing an cycloalkyl substituent and having from about 4 to about 20 carbon atoms (and all combinations and subcombinations of ranges and specific numbers of carbon atoms therein), with from about 6 to about 12 carbon atoms being preferred and can include but are not limited to methylcyclopropyl, methylcyclohexyl, isopropylcyclohexyl, and butyl-cyclohexyl groups. Cycloalkylalkyl radical or group can be optionally substituted with one or more substituents for the alkyl groups including but not limited to hydroxy, cyano, alkyl, alkoxy, thioalkyl, halo, haloalkyl, hydroxyalkyl, nitro, amino, alkylamino and dialkylamino.

The term acyl refers to an alkyl, substituted alkyl, alkenyl, alkynyl, cycloalkyl, cycloalkenyl, aryl, heteroaryl, or heterocyclyl group as defined above bonded through one or more carbonyl —C(=O)— groups to give a group of formula —C(=O)R where R is the substituted alkyl, alkenyl, alkynyl, cycloalkyl, cycloalkenyl, aryl, heteroaryl, or heterocyclyl group. When the term acyl is used in conjunction with another group, as in acylamino, this refers to the carbonyl group {—C(=O)} linked to the second named group. Thus, acylamino or carbamoyl refers to —C(=O)NH$_2$, acylalkylamino can refer to groups such as —C(=O)NR'R" where R' and R" can be H or alkyl. Amidalkyl refers to groups such as —CH$_2$C(=O)NH$_2$, —CH$_2$CH$_2$C(=O)NH$_2$) and more generally —(CH$_2$)$_p$C(=O)NH$_2$. Carboxy refers to the radical or group —C(=O)OH, carboxyalkyl refers to the groups such as —(CH$_2$)$_p$C(=O)OH, alkyl carboxyalkyl refers to groups such as (—C(=O)O-(alkyl)), and alkoxycarbonyl or acylalkoxy refers to a (—C(=O)O-(alkyl)) group, where alkyl is previously defined. As used herein aroyoyl or acylaryl refers to a (—C(=O)(aryl)) group, wherein aryl is as previously defined. Exemplary aroyl groups include benzoyl and naphthoyl. Acetyl refers to the group CH$_3$C(=O)— and may be abbreviated by the term "Ac" as is Table 5. Formyl refers to the radical or group HC(=O)—. In the aforementioned group p can be independently the integer 0, 1, 2, or 3.

Aryloxy radical refers to optionally substituted mono or bicyclic aromatic radical having from about 5 to about 14 carbon atoms and an (aryl-O—) radical group wherein aryl is as previously defined. Such aryloxy radicals include but are not limited to that illustrated by the radical of formula (12). Optional substituents on the aryl ring in the aryloxy radical may include but are not limited to hydrogen, alkyl, halogen, hydroxy, alkoxy, alkoxycarbonyl or other substituents. Embodiments of IAP binding compounds of the present invention can include an optionally aryloxy group like the phenoxy radical linked to the pyrrolidine ring as illustrated but not limited to compounds in Table 5. Some embodiment of IAP binding compounds include include a phenoxy radical where the $K_d$ as determined by methods described, for example, in Example 1 is less than about 0.1 micromolar.

The terms "alkoxy" and "alkoxyl" refer to an optionally substituted (alkyl-O—) radical or group wherein alkyl is as previously defined. Exemplary alkoxy radicals or groups include methoxy, ethoxy, n-propoxy, i-propoxy, n-butoxy, cyclopropyl-methoxy, and heptoxy. Alkoxy radicals can also include optionally substituted alkyl in the alkylO— group. Alkoxy can include including optionally substituted aryl groups as previously defined and illustrated by the non-limiting radical of formula (13). A "lower alkoxy" group refers to an optionally substituted alkoxy group containing from one to five carbon atoms. "Polyether" refers to a compound or moiety possessing multiple ether linkages, such as, but not limited to, polyethylene glycols or polypropylene glycols. "Polyalkylethers" refers to alkyls interconnected by or otherwise possessing multiple ether linkages as illustrated by the non-limiting structure of formula (85) in Scheme VIII of Example 16. "Arylalkyloxy" means an arylalkyl-O— group in which the arylalkyl group is as previously described. Exemplary arylalkyloxy groups include benzyloxy (C$_6$H$_5$CH$_2$O—) radical (BnO—), or 1- or 2-naphthalenemethoxy. Optional substituents on the aryl ring in the benzyloxy radical may include but are not limited to hydrogen, alkyl, halogen, hydroxy, alkoxy, and alkoxycarbonyl or other substituents as defined for the alkyl group.

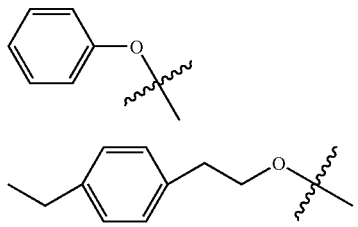

(12)

(13)

Arylamino radical refers to optionally substituted mono or bicyclic aromatic radical having from about 5 to about 14 carbon atoms and an (—NH(aryl)) radical group wherein aryl can be optionally substituted as previously defined for alkyl. Optional substituents on the aryl ring in the arylamino radical may include but are not limited to hydrogen, alkyl, halogen, hydroxy, alkoxy, and alkoxycarbonyl. A example of an arylamino group is the anilino radical or group. Amino refers to an —NH$_2$ group and alkylamino refer to a radical (—NHR') group wherein R' is H, alkyl, cycloalkyl, aryl, heteroaryl, aralkyl or optionally substituted versions of these as previously defined. Exemplary alkylamino radical groups include methylamino, ethylamino, n-propylamino, i-propylamino, n-butylamino, and heptylamino. The benzylamino radical refers to the arylamino group C$_6$H$_5$CH$_2$NH—, the aryl group may have optional substituents including but are not limited to hydrogen, alkyl, halogen, hydroxy, alkoxy, and alkoxycarbonyl or other substituents.

Dialkylamino includes reference to a radical (—NR'R"), wherein R' and R" can be each independently be an H, alkyl, cycloalkyl, aryl, heteroaryl, aralkyl or optionally substituted versions of these as previously defined. Examples of dialkylamino radicals include, but are not limited to, dimethylamino, methylethylamino, diethylamino, di(1-methylethyl)amino, and the like.

Heteroaryl includes reference to a monovalent aromatic radical or group having one or more rings incorporating one, two or three heteroatoms within the ring (chosen from nitrogen, oxygen, or sulfur). These heteroaryls can optionally have hydrogen atoms substituted with one or more other substituents. Examples of these heteroaryl radicals include optionally substituted benzofurans, benzo[b]thiophene 1-oxide, indoles, 2- or 3-thienyls or thiophenyls, thiazoyls, pyrazines, pyridines, or the structures of (4a) or (4b). For example, the structure of formula (E10) with derivatives listed in Table 9, can include a fused ring R$_{10}$ with a heteroatom X$_2$ (N, O, or other) and substituents such as R$_{11}$ or R'$_{11}$ including but not limited to hydrogen, halogens, optionally substituted heteroaryls like pyridine, benzofuran, indoles, thiazoyl, pyrazine, an alkoxyheteroaryl like methoxy pyridine, or other groups.

The terms heteroalkyl, heteroalkylene, heteroalkenyl, heteroalkenylene, heteroalkynyl, and heteroalkynylene include reference to alkyl, alkylene, alkenyl, alkenylene, alkynyl, and alkynylene radicals or groups, in which one or more of the carbon atoms have been replaced or substituted with atoms such as but not limited to single or multiply bonded nitrogen, sulfur, oxygen, or these atoms having one or more hydrogens to satisfy the valancy requirements of the atom. Such substitutions can be used to form molecules having functional groups including but not limited to amines, ethers, and sulfides. A non-limiting example of a heteroalkynyl group is illustrated by the group —CH(Me)OCH$_2$C≡CH.

Heterocycloalkyl radical include reference to a monovalent saturated carbocyclic radical or group consisting of one or more rings, incorporating one, two or three heteroatoms (chosen from nitrogen, oxygen or sulfur), which can optionally be substituted with one or more substituents.

Heterocycloalkenyl includes reference to a monovalent unsaturated carbocyclic radical consisting of one or more rings containing one or more carbon-carbon double bonds where carbon atoms are replaced or substituted for by one, two or three heteroatoms within the one or more rings, the heteroatoms chosen from nitrogen, oxygen, or sulfur, the heterocycloalkenyl can optionally be substituted with one or more substituents.

Various groups used in the molecules of the present invention can have one or more hydrogens atoms substituted for chemical moieties or other substituents. Substituents may include but are not limited to halo or halogen (e. g, F, Cl, Br, I), haloalkyls such as —CF$_3$, —CF$_2$CF$_3$, —CH$_2$CF$_3$ and the like, thioalkyl, nitro, optionally substituted alkyl, cycloalkyl, aralkyl, aryl, heteroaryls like benzofurans, indoles, thienyls, thiophenyls, thiazoyls, pyrazines, pyridines, alkoxy pyridine, hydroxy (—OH), alkoxy (—OR), aryloxy, alkoxyheteroaryl, cyano (—CN), carbonyl —C(=O)—, carboxy (—COOH) and carboxylate salts; —(CH$_2$)$_p$C(=O)OH, groups or radicals —(CH$_2$)$_p$C(=O)O(alkyl), and —CH$_2$)$_p$C(=O)NH$_2$ where p is independently the integer 0, 1, 2, or 3; sulfonates such as but not limited to tosyl, brosyl, or mesyl; sulfone, imine, or oxime groups, groups like —(C=O)Oalkyl, aminocarbonyl or carbamoyl —(C=O)NH$_2$), —N-substituted aminocarbonyl —(C=O)NHR", amino, alkylamino (—NHR') and dialkylamino (—NHR'R"). In relation to the aforementioned amino and related groups, each moiety R' or R" can be, independently include of H, alkyl, cycloalkyl, aryl, heteroaryl, aralkyl or optionally-substituted alkyl, cycloalkyl, aryl, heteroaryl, araalkyl. Where one or more hydrogens atoms are substituted for chemical moieties or other substituents, the substituents can be chosen so that IAP binding compounds of formula (2), (3), or (5) that contain them have a K$_d$ as measured by methods described, for example, in Example 1 of less than about 100 micromolar, in some embodiments have a K$_d$ of less than 1 micromolar, and in other embodiments have a K$_d$ of less than 0.1 micromolar. In embodiments of where one or more hydrogens atoms are substituted for chemical moieties or other substituents, the substituents can be chosen so that IAP binding compounds of formula (2), (3), or (5) that contain them have an EC$_{50}$ as measured by methods described, for example, in Example 2 of less than about 0.5 micromolar, in some embodiments have an EC$_{50}$ of less than about 0.06 micromolar. In embodiments of where one or more hydrogens atoms are substituted for chemical moieties or other substituents, the substituents can be chosen so that IAP binding compounds of formula (2), (3), or (5) that contain them have a binding constant K$_d$ of less than about 1 micromolar, preferably less than 0.1 micromolar and an EC$_{50}$ of less than about 1 micromolar, preferably less than about 0.5 micromolar, and in some embodiments an EC$_{50}$ of less than about 0.06 micromolar.

Amino acids can be used in the IAP binding compound compounds of this invention and may include the 20 naturally-occurring amino acids, known artificial amino acids such as beta or gamma amino acids, and amino acids containing non-natural side chains, and/or other similar monomers such as hydroxyacids. Preferably the amino acids used in the IAP binding compounds of the present invention are the 20 naturally-occurring amino acids. The amino acids or artificial amino acids are chosen with the effect that the corresponding IAP binding compound binds IAPs, and preferably binds the BIR domain of an IAP, and the resulting IAP binding compound is permeable to the cell. A non-limiting example of such an amino acid includes the use of Abu (2-aminobutyric acid) as an amino acid in the IAP binding cargo molecule. Where the molecule of structure (2), (3), or (5) includes amino acids, it is preferred that the N-terminal amino acid is Ala or Abu.

Where one or more chiral centers exist in an amino acid, artificial amino acid, or atom of an IAP binding compound of structure (2), (3), or (5), any of the enantiomers, D or L and more generally R or S configuration, or diastereoisomers may optionally be used in the IAP binding compound.

When any variable occurs more than one time in any constituent or in any formula, its definition in each occurrence is independent of its definition at every other occurrence. Combinations of substituents and/or variables are permissible only if such combinations result in stable compounds.

It is believed the chemical formulas and names used herein correctly and accurately reflect the underlying chemical compounds. However, the nature and value of the present invention does not depend upon the theoretical correctness of these formulae, in whole or in part. Thus it is understood that the formulas used herein, as well as the chemical names attributed to the correspondingly indicated compounds, are not intended to limit the invention in any way, including restricting it to any specific tautomeric form or to any specific optical; or geometric isomer, except where such stereochemistry is clearly defined.

In embodiments of compounds of structure (2), (3), or (5) substituents such as $A_1$, $A_2$, $R_{1a}$, and $R_{1b}$, $R_2$, $X_1$, Y, Z, M, G, or $R_{10}$, may be chosen independently so that compounds of structure (2), (3), or (5) are not a tripeptide or a tetrapeptide of amino acids, for example AVPI or AVP.

Some embodiments of the compounds of structure (2), when $A_2$ is H, $X_1$ is —NH—, J is —CH—, and n is 0 for $R_2$, can be depicted by structure (3):

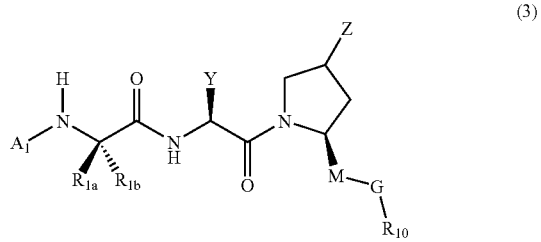

(3)

In some embodiments of compounds of structure (3), $A_1$ is H, lower alkyl, or optionally-substituted lower alkyl group, an N-acyl derivative like acylamino or acylalkylamino, t-butoxycarbonyl, acetyl, formyl, carbamoyl, alkylene, or other; $R_{1a}$ and $R_{1b}$ are separately H, lower alkyl, optionally-substituted lower alkyl, lower alkylene, optionally substituted lower alkylene group; or $A_1$ together with either $R_{1a}$ or $R_{1b}$ form an optionally substituted heterocycloalkyl group of 3 to 6 atoms as illustrated by some of the non-limiting embodiments of compounds in Table 5.

In IAP binding compounds of structure (3), Y can be H, an alkyl group, an alkyl group of 1 to 10 carbon atoms, a branched alkyl group of 1 to 10 carbon atoms, an alkynyl group, heteroalkynyl, a cycloalkyl group of 3 to 7 carbon atoms, aryl, heteroaryl, arylalkyl; optionally-substituted versions of the aforementioned groups such as optionally substituted alkyl group, optionally substituted alkyl group of 1 to 10 carbon atoms, an optionally substituted branched alkyl group of 1 to 10 carbon atoms, an optionally substituted alkenyl group, an optionally substituted alkynyl group, an optionally substituted heteroalkynyl group, an optionally substituted cycloalkyl group or 3 to 7 carbon atoms, an optionally substituted aryl group, an optionally substituted heteroaryl group, an optionally substituted arylalkyl group; in some embodiments the substituent or moiety for the aforementioned substituted group includes one or more hydroxy groups; or Y together with Z, M, G, or $R_{10}$ can for an optionally substituted carbocyclic ring, or an optionally substituted heterocyclic ring containing 1 to 5 heteroatoms, where Y is linked to Z, M, G, or $R_{10}$; preferably Y is linked to Y, M, G, or $R_{10}$ by any number of atoms up to about 20 atoms. A non-limiting example of such a heterocyclic ring is illustrated by the IAP binding molecule having the structure of formula (E12-2) in Example 12.

In IAP binding compounds of structure (3), Z can be H, alkyl, hydroxy, amino, alkylamino, diakylamino, alkoxy, cycloalkyl, cycloalkyloxy, aryl, heteroaryl, aryloxy, heteroaryloxy; optionally substituted versions of these groups; optionally substituted versions of these groups including one or more hydroxyl groups; or Z together with Y, M, G, or $R_{10}$ can form an optionally substituted carbocyclic ring, or an optionally substituted heterocyclic ring containing 1 to 5 heteroatoms, where Z is linked to Y, M, G, or $R_{10}$; preferably Z is linked to Y, M, G, or $R_{10}$ by any number of atoms up to about 20 atoms. In some embodiments, Z is an alkyl, hydroxy, amino, alkylamino, dialkylamino, alkoxy, cycloalkyl, cycloalkyloxy, aryl, heteroaryl, aryloxy, or heteroaryloxy group. The stereochemistry of the Z substituent or group may be indicated using a bold wedged bond to show a Z group coming out of the plane of the page or a dashed wedged bond to show a Z group behind the plane of the page. In embodiments of (3), the IAP binding molecule may have a structure where the Z group is directed out of the plane of the page, the IAP binding molecule may have a structure where the Z group is directed behind the plane of the page, or the IAP binding molecule may include a mixture where the Z group is a combination of these.

In IAP binding compounds of structure (3), M can be an optionally-substituted alkyl, alkenyl, or alkynyl group; M can be an optionally-substituted alkyl, alkenyl, or alkynyl group of 1 to 5 carbon atoms; M can be an optionally-substituted alkylene, alkenylene, or alkynylene group; or an optionally-substituted alkylene, alkenylene, or alkynylene group of 1 to 5 carbon atoms. In some embodiments, for example but not limited to IAP binding compounds of structure (E6) or (E14), M is a diradical alkylene like the methylene group linked at one end of the methylene group the 2 position of the pyrrolidine ring and at the other end of the methylene group to an aryl group, a heteroaryl group, or an optionally substituted heteroaryl group like a benzofuran or indole group, or optionally substituted versions of groups of structure (4a-d).

In IAP binding compounds of structure (3), G can be absent (a bond) as in the non-limiting examples of compounds of structure (E6) or (E14), or G can be a heteroatom including but not limited to —O—; —NH—; —(C═O)—; —S(O)$_t$— where t can be the integer 0, 1, or 2; —NR$_{18}$—; —NCOR$_{18}$—; or —NS(O)$_x$R$_{18}$— where x can be the integer 0, 1, or 2, and R$_{18}$ can be lower alkyl, optionally-substituted lower alkyl, or cycloalkyl or R$_{18}$ can be contained within an optionally substituted carbocyclic, or optionally substituted heterocyclic ring containing 1 to 5 heteroatoms, where $R_{18}$ is linked to Z, M, or $R_{10}$, preferably $R_{18}$ is linked to Z, M, or $R_{10}$, by any number of atoms up to about 20 atoms.

In IAP binding compounds of structure (3), $R_{10}$ can be an aryl, a heteroaryl group, a fused aryl, or a fused heteroaryl group. In some embodiments, for example but not limited to compounds in Table 5, $R_{10}$ can be a substituted aryl, a substituted heteroaryl group, a substituted fused aryl, or a substituted fused heteroaryl group. In some embodiments $R_{10}$ can be any one of structures (4a), (4b), (4c), or (4d):

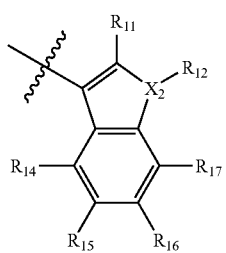

(4a)

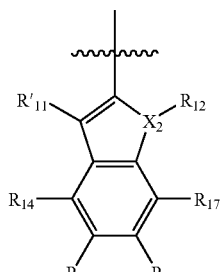

(4b)

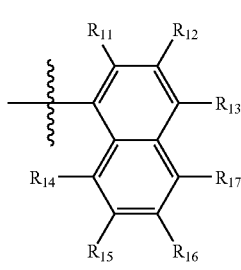

(4c)

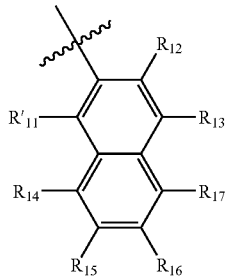

(4d)

where $X_2$ is a heteroatom in structures (4a) or (4b) or $X_2$ is a carbon-carbon bond in structures (4c) or (4d), and independently groups $R_{11}$, $R'_{11}$, $R_{12}$, any of $R_{13-17}$, or any of $R_{14-17}$ can be H, halogen, alkyl, alkenyl, alkynyl, aryl, heteroaryl, hydroxyl, alkoxy, polyalkylether, amino, alkylamino, dialkylamino, alkyloxyalkyl, sulfonate, aryloxy, heteroaryloxy, other substituents or optionally substituted versions of these groups. In embodiments where $R_{11}$ or $R'_{11}$ is a heteroaryl group, it can be a 2- or 3-thienyl $SC_4H_3$—(thiophenyl) group, pyridine, pyrazine or optionally substituted versions of these. In some embodiments $R_{12}$ can be an aryl or a heteroaryl group, such as but not limited to benzofuran, indole, benzo[b]thiophene-1-oxide or benzo[b]thiophene-1,1-dioxide or optionally substituted versions of these. Where $X_2$ is either —O— or —S(O)$_k$—, for the integer k which can independently be 0, 1, or 2, $R_{12}$ is absent. Independently $R_{11}$, $R'_{11}$, $R_{12}$, any of $R_{13-17}$, or any of $R_{14-17}$ can be H, optionally-substituted alkyl, alkenyl, alkynyl, aryl, heteroaryl, hydroxyl, alkoxy, polyalkylether, carboxyalkyl, alkyl carboxyalkyl, amino, alkylamino, dialkylamino, alkyloxyalkyl, aryloxy, or heteroaryloxy. Independently $R_{11}$, $R'_{11}$, $R_{12}$, any of $R_{13-17}$, or any of $R_{14-17}$ can be acyl or acetyl groups, carboxylate, sulfonate, sulfone, imine, or oxime groups; or groups $R_{11}$, $R'_{11}$, $R_{12}$, any of $R_{13-17}$, or any of $R_{14-17}$ can be contained within a carbocyclic ring, or a heterocyclic ring containing 1 to 5 heteroatoms, and linked to groups at position Y, Z, M, G, $R_{11}$, $R'_{11}$, $R_{12}$, any of $R_{13-17}$, or any of $R_{14-17}$, preferably these groups are linked by any number of atoms up to about 20 atoms. In some embodiments $R_{10}$ can be cycloalkyl, aryl, heterocycloalkyl, heterocycloalkenyl, heteroaryl, or optionally substituted embodiments of these. In some embodiments $R_{10}$ can be the group:

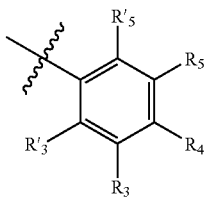

where $R_3$, $R'_3$, $R_4$, $R_5$, $R'_5$, can each independently be substituents like H, alkyl, cycloalkyl, alkylene, aryl, heteroaryl, alkoxy optionally substituted alkyl, cycloalkyl, alkylene, aryl, heteroaryl, halo, cyano, —(CH$_2$)$_p$C(=O)OH, —(CH$_2$)$_p$C(=O)O-alkyl, —(CH$_2$)$_p$C(=O)NH$_2$, p is independently the integer 0, 1, 2, or 3. For example, in the IAP binding compound of structure (E4) where M is alkenylene, G is a heteroatom like —O—, $R_{10}$ can be an optionally substituted aryl group having substituents for example but not limited to hydrogen, chloro, bromo, alkyl, alkylene, alkoxy, or combinations of these.

Some embodiments of IAP binding compounds of formula (3) include compounds of structure (5) where:

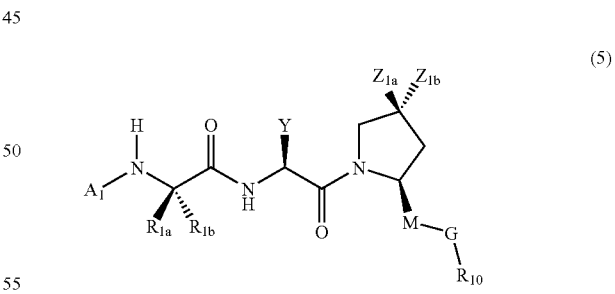

(5)

$A_1$ is H, or lower alkyl, or $A_1$ and $R_{1b}$ together form a ring of 3-5 atoms. In these embodiments, $R_{1a}$ is H and $R_{1b}$ can be lower an alkyl group, or together with $A_1$ forms a ring of 3 to 5 atoms.

In embodiments of IAP binding compounds of structure (5), Y can be an alkyl group, an alkyl group of 1 to 10 carbon atoms, a branched alkyl group of 1 to 10 carbon atoms, an alkynyl group, heteroalkynyl, a cycloalkyl group of 3 to 7 carbon atoms, optionally substituted versions of the aforementioned groups, and/or hydroxy substituted versions of the aforementioned groups, or Y together with $Z_{1a}$, $Z_{1b}$, or $R_{10}$ forms a carbocyclic ring, or a heterocyclic ring containing 1 to 5 heteroatoms, where Y is linked to $Z_{1a}$, $Z_{1b}$, or $R_{10}$; preferably Y is linked to $Z_{1a}$, $Z_{1b}$, or $R_{10}$ by any number of atoms up to about 20 atoms;

In embodiments of IAP binding compounds of structure (5), $Z_{1a}$ and $Z_{1b}$ can independently be an H, hydroxy, amino, alkylamino, diakylamino, alkoxy, aryloxy, or heteroaryloxy group; or $Z_{1a}$, or $Z_{1b}$, together with Y or $R_{10}$ form a carbocyclic ring, or a heterocyclic ring containing 1 to 5 heteroatoms, where $Z_{1a}$ or $Z_{1b}$, is linked to Y or $R_{10}$; preferably $Z_{1a}$ or $Z_{1b}$, is linked to Y or $R_{10}$ by any number of atoms up to about 20 atoms;

In embodiments of IAP binding compounds of structure (5), M can be an optionally-substituted alkyl or an optionally-substituted alkylene group of 1 to 5 carbon atoms. In these structures, G can be absent (a bond), or a heteroatom including —O—; —NH—; —(C=O)—; —$NR_{18}$—; —$NCOR_{18}$—; or —$NS(O)_xR_{18}$— where x=0, 1, or 2, and $R_{18}$ is lower alkyl, optionally-substituted lower alkyl group.

The IAP binding compounds or molecules of structure (2), (3), or (5) can be prepared by various processes, which are described by the non-limiting Schemes in the Examples and which also form part of the subject matter of the present invention. These IAP binding molecules may be prepared from molecules of structure (6a) or (6b):

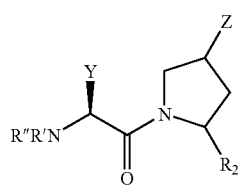

(6a)

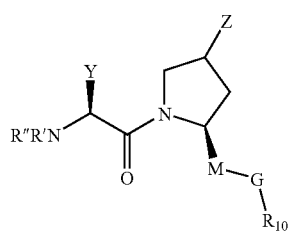

(6b)

where Y, M, Z, G, $R_2$ and $R_{10}$ are previously described and where R' and R" can be H, or a protecting group. The stereochemistry of the Z or M substituent or group may be indicated using a bold wedged bond to show either group coming out of the plane of the page or a dashed wedged bond to show a Z or M group behind the plane of the page. In embodiments of structure (6a) or (6b), the IAP binding molecule may have a structure where the Z or M group is directed out of the plane of the page, the IAP binding molecule may have a structure where the Z or M group is directed behind the plane of the page, or the IAP binding molecule may include a mixture where the Z or M group includes a combination of these.

Structures of formula structure (6a) or (6b) may be prepared from compounds such as but not limited to pyrrolidines like (1) in Scheme I or (29) in Scheme IVa using the procedures or similar processes described herein. The structures of formula structure (6a) or (6b) may be further reacted to yield IAP binding molecules of structure (2), (3), or (5) by treatment with an N-Boc-amino acid or other suitable amine containing moiety that includes $A_1$, $A_2$, $R_{1a}$, or $R_{1b}$ or combinations of these as described herein.

Certain acidic or basic compounds of the present invention may exist as zwitterions. All forms of the compounds, including free acid, free base and zwitterions, are contemplated to be within the scope of the present invention. It is well known in the art that compounds containing both amino and carboxyl groups often exist in equilibrium with their zwitterionic forms. Thus, any of the compounds described herein throughout that contain, for example, both amino and carboxyl groups also include reference to their corresponding zwitterions.

In any of the above teachings, an IAP binding cargo molecule or other IAP binding compound of the invention may be either a compound of one of the formulae herein described, or a stereoisomer, prodrug, pharmaceutically acceptable salt, hydrate, solvate, acid salt hydrate, or isomorphic crystalline form thereof.

Pharmaceutically acceptable salt refers to those salts of the IAP binding cargo molecules and IAP binding compounds of structure (2), (3), or (5) or dimers thereof which retain the biological effectiveness and properties of the free bases or free acids, cell permeation and IAP binding, and which are not biologically or otherwise undesirable. If the compound exists as a free base, the desired salt may be prepared by methods known to those of ordinary skill in the art, such as treatment of the compound with an inorganic acids such as hydrochloric acid, hydrobromic acid, sulfuric acid, nitric acid, phosphoric acid and the like; or with an organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. If the compound exists as a free acid, the desired salt may also be prepared by methods known to those of ordinary skill in the art, such as the treatment of the compound with an inorganic base or an organic base. Salts derived from inorganic bases include, but are not limited to, the sodium, potassium, lithium, ammonium, calcium, magnesium, iron, zinc, copper, manganese, aluminum salts and the like. Salts derived from organic bases include, but are not limited to, salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-dimethylaminoethanol, 2-diethylaminoethanol, trimethamine, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins and the like.

The IAP binding cargo molecules or their pharmaceutically acceptable salts may include pharmaceutically acceptable solvent molecules within their crystal lattice. Where the solvent is water, the compounds may form hydrates, in the case of other solvents and in particular organic solvents such as but not limited to ethanol the compounds may form solvates. The IAP binding cargo molecules or IAP binding compounds of structure (2), (3), or (5) and its homologs may be formulated, isolated, or purified as solvates.

The compounds employed in the methods of the present invention may exist in prodrug form. Prodrug includes any covalently bonded carriers which release the active parent drug, for example, as according to formula (2) or other formulas or compounds employed in the methods of the present invention in vivo when such prodrug is administered to a mammalian subject. Since prodrugs are known to enhance numerous desirable qualities of pharmaceuticals (e.g. solubility, bioavailability, manufacturing, etc.) the compounds employed in the present methods may, if desired, be delivered in prodrug form. Thus, the present invention contemplates methods of delivering prodrugs. Prodrugs of the compounds employed in the present invention, for example formula (2) may be prepared by modifying functional groups present in the compound in such a way that the modifications are cleaved, either in routine manipulation or in vivo, to the parent compound.

Accordingly, prodrugs include, for example, compounds described herein in which a hydroxy, amino, or carboxy group is bonded to any group that, when the prodrug is administered to a mammalian subject, cleaves to form a free hydroxyl, free amino, or carboxylic acid, respectively. Examples include, but are not limited to, acetate, formate and benzoate derivatives of alcohol and amine functional groups; and alkyl, carbocyclic, aryl, and alkylaryl esters such as methyl, ethyl, n-propyl, iso-propyl, butyl, isobutyl, sec-butyl, tert-butyl, cyclopropyl, phenyl, benzyl, and phenethyl esters, and the like.

The compounds employed in the methods of the present invention may be prepared in a number of ways well known to those skilled in the art. The compounds can be synthesized, for example, by the methods described in the specification and example, or variations thereon as appreciated by the skilled artisan. All processes disclosed in association with the present invention are contemplated to be practiced on any scale, including microgram, milligram, gram, multi-gram, kilogram, multi-kilogram or commercial industrial scale.

IAP binding compounds of structure (2), (3), or (5) can be mixed or combined with pharmaceutically acceptable excipients or treated by lyophilization. These pharmaceutical compositions may be administered topically, locally or systemically to a sample of cells, a tissue, or patient. Topical or local administration can allow for greater control of application of the pharmaceutical composition. The IAP binding molecules or compounds including structure (2), (3), or (5) singularly or in combination, can be mixed with an appropriate pharmaceutical carrier prior to administration. Examples of generally used pharmaceutical carriers and additives that can be used to form pharmaceutical, diagnostic, or therapeutic composition of the IAP binding molecules may include but are not limited to conventional diluents, binders, lubricants, coloring agents, disintegrating agents, buffer agents, isotonizing agents, preservants, anesthetics and the like. Pharmaceutical carriers that may be used include but are not limited to water, saline, ethanol, dextran, sucrose, lactose, maltose, xylose, trehalose, mannitol, xylitol, sorbitol, inositol, serum albumin, gelatin, creatinine, polyethylene glycol, non-ionic surfactants (e.g. polyoxyethylene sorbitan fatty acid esters, polyoxyethylene hardened castor oil, sucrose fatty acid esters, polyoxyethylene polyoxypropylene glycol) and similar compounds. Pharmaceutical carriers and excipients as well as IAP binding molecules may also be used in combination.

Stereoisomers are compounds having identical molecular formulae and nature or sequence of bonding but differing in the arrangement of their atoms in space and include optical and geometrical isomers. Compounds of the present invention, or their pharmaceutically acceptable salts, can have one or more asymmetric carbon atoms or other asymmetric atoms in their structure, and may therefore exist as single stereoisomers, enantiomers, diastereoisomers, racemates, and mixtures of enantiomers or diastereomers. These compounds may also include geometric isomers. All such stereoisomers, racemates and mixtures thereof the IAP binding compounds and IAP binding cargo molecules of the present invention are intended to be within the scope of this invention unless the specific stereochemistry or isomeric form is specifically indicated. It is well known in the art how to prepare and isolate such optically active forms. For example, mixtures of stereoisomers may be separated by standard techniques including, but not limited to, resolution of racemic forms, normal, reverse-phase, and chiral chromatography, preferential salt formation, recrystallization, and the like, or by chiral synthesis either from chiral starting materials or by deliberate synthesis of target chiral centers.

IAP binding molecules of structures (2), (3), or (5) that contain chiral centers and the molecules can be in the form of a single enantiomer or as a racemic mixture of enantiomers. In some cases, i.e., with regard to the structure of certain specific IAP binding molecules, chirality (i.e., relative stereochemistry) of substituents or groups is indicated in the structure using a bold wedged bond to indicate a substituent coming out of the plane of the page and a dashed wedged bond to indicate a substituent behind the plane of the page. In other cases the stereochemistry is not indicated and such structures are intended to encompass both the enantiomerically pure or purified forms of the compound shown as well as a racemic mixture of enantiomers.

As will be readily understood, functional groups present may contain protecting groups during the course of synthesis. Protecting groups are chemical functional groups that can be selectively appended to and removed from functionalities, such as amine, hydroxyl groups or carboxyl groups. These groups are present in a chemical compound to render such functionality inert to chemical reaction conditions to which the compound is exposed. Any of a variety of protecting groups may be employed with the present invention. Protecting groups include the benzyloxycarbonyl group and the tert-butyloxycarbonyl group. The term "protecting group" or "blocking group" refers to any group which when bound to one or more hydroxyl, amino, carboxyl or other groups of the compounds (including intermediates thereof such as the aminolactams, aminolactones, etc.) prevents reactions from occurring at these groups and which protecting group can optionally be removed by conventional chemical or enzymatic steps to reestablish the hydroxyl, amino, carboxyl group for use in an IAP binding compound. The particular removable blocking group employed is not critical and preferred removable hydroxyl or amine blocking groups include conventional substituents such as allyl, benzyl, acetyl, chloroacetyl, thiobenzyl, benzylidine, phenacyl, t-butyl-diphenylsilyl, t-butyl carbamate, benzyl carbamate and any other group that can be introduced chemically onto a hydroxyl, amine, or other functionality and later selectively removed either by chemical or enzymatic methods in mild conditions compatible with the nature of the product.

The cargo portion of the molecule may be part of the backbone or IAP binding portion of the molecule or the cargo portion may be chemically bonded or linked to the IAP binding portion of the molecule. For example, the cargo portion may be another unit of the formula (2), (3) or (5), linked by a linking group to the first unit, thereby forming a dimer and may further comprise an additional cargo portion. The cargo portion may also be any of the substituents $A_1$, $A_2$, $R_{1a}$, $R_{1b}$, Y, $R_2$, or Z in molecules of formula (2), preferably the cargo portion is linked to Y, $R_2$, or Z in molecules of formula (2). In molecules of formula (3), or (5), the cargo portion may be any of the substituents $A_1$, $R_{1a}$, $R_{1b}$, $R_{10}$, Y, M, G, or Z (includes $Z_{1a}$ and $Z_{1b}$), preferably the cargo portion includes a substituent linked at Y, Z (include $Z_{1a}$ and $Z_{1b}$), or $R_{10}$. The cargo portion of the molecule may include but is not limited to structures, moieties, and substituents for imaging, therapeutics, detectable groups, probes, labels, or markers. The cargo portion and IAP binding portion of the molecule may be connected by a chemical bond to the IAP binding portion including but not limited to amide, ester, or disulfide bonds, chelation, or by a linking group such as diaminobutane or ethylene glycol and its oligomers where it is desirable to separate the IAP binding portion of the molecule from the cargo portion of the molecule. One or more atoms in any portion of the IAP binding cargo molecule may be a radioisotope and used for detection or treatment.

The ability to quickly assay small molecules for their effectiveness in disrupting protein-protein interactions can be used in the development of viable drug candidates. One aspect of the present invention comprises an assay that can be used to test the binding affinity of a library of IAP binding compounds for their ability to bind to the BIR domain of an inhibitor of apoptosis protein (IAP), for example the BIR3 domain of mammalian XIAP. The assay may be based on a detectable label, which can be a fluorogenic dye molecule that is the cargo portion of an IAP-binding cargo molecule. The detectable label may be any of the substituents in the molecules of formula (2), (3), or (5). For example, the detectable label may be linked to the substituent $R_2$, or linked to the substituents $R_{2a-c}$ supra in molecules having the structure of formula (2)

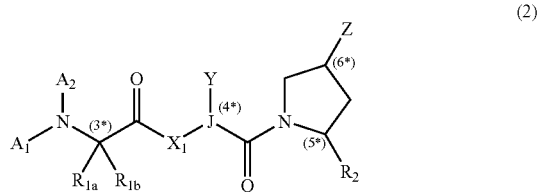

(2)

Similarly the detectable label may be linked to substituents like Y, Z, M, G, $R_{10}$, or other substituents in molecules having the structure of formula (3), or (5) and pharmaceutically acceptable salt thereof.

A detectable label included in a molecule of formula (2), (3), or (5) can be a dye such as is a fluorogenic dye whose emission is sensitive to the environment of the dye. However, the detectable label portion of an IAP binding cargo molecule may also be an NMR-active nucleus or a contrast agent and the selective identification is performed through nuclear magnetic resonance or magnetic resonance imaging. The detectable label in an IAP-binding cargo molecule may also be a radioisotope and where the selective identification is performed through positron emission tomography. The cargo portion of the molecule may also be used to destroy cells through a toxic effect of the cargo portion of the molecule.

Without wishing to be bound by theory, it is believed that the molecule of structure (2), (3), or (5) packs into the BIR domain of an IAP. Where the molecule of structure (2), (3), or (5) has a fluorogenic dye as a cargo substituent, preferably the packing of the molecule of structure (2), (3), or (5) into the groove of the BIR of an IAP causes a large shift in emission maximum and intensity of the dye when the environment of the IAP binding cargo molecule changes from water to the hydrophobic pocket or binding in or near the groove of the IAP. If a molecule (e. g., the native Smac protein or a test IAP binding compound) displaces the IAP binding cargo molecule of formula (2), (3), or (5) with the fluorogenic dye from the IAP, then emission will shift back to the spectrum observed for the IAP binding cargo molecule with the fluorogenic dye in water. Since the emission intensity is related to the binding of a test peptide, or IAP binding compound with the IAP, the intensity can be used to estimate the equilibrium constant, $K_a$, for displacement of the molecule of formula (2), (3), or (5) by the IAP binding compound; $K_a$ refers to an equilibrium constant for association that is inversely related to the dissociation $K_d=1/K_a$. The larger the equilibrium constant $K_a$, the greater affinity the IAP binding compound has for the BIR or BIR3. This allows the most promising inhibitors to be quickly determined, and structural information about effective inhibitors can be incorporated into the design of candidates for the next round of testing. An IAP binding cargo molecule of formula (2) having a detectable label may be complexed to an IAP and used to screen other IAP binding compounds.

It will be understood by those of skill in the art that, although the IAP binding cargo molecule of formula (2), (3), or (5) described above is exemplified and preferred for practice of the invention, various combinations of IAP binding compounds, BIR binding domains of different IAP's, and detectable labels may be used interchangeably to create variations of the assay described above.

The IAP binding cargo molecule of structure (2), (3), or (5) or dimers thereof may comprise any suitable therapeutic molecule or detectable label, such as but not limited to a fluorophore, radioisotope, or NMR active nucleus, such that binding of the IAP binding cargo molecule to the BIR domain of an IAP, and preferably the BIR3 groove of XIAP, is not detrimentally affected by the presence of the detectable label or therapeutic in the IAP binding cargo molecule. Preferably the molecule is cell permeable. A non-limiting example of a detectable label which may be coupled to the IAP binding compounds and IAP binding cargo molecules of structure (2), (3), or (5) is the fluorogenic dye 6-Bromoacetyl-2-dimethylaminonaphthalene (badan) dye. Badan is a fluorogenic dye whose sensitivity to environmental changes has previously been made use of to probe protein binding interactions.

The IAP binding cargo molecules of structure (2), (3), or (5) can be used in an assay of test compounds that can bind to the BIR domain of an IAP. These molecules may be used for example to relieve suppression of apoptosis or to release sequestered proteins like Smac from IAPs in cells. A high-throughput, cell-free assay, for compounds of structure (2), (3), or (5) may also be prepared using a fluorescently labeled peptide like (AbuRPF-K(5-Fam)-NH$_2$). A wide variety of IAP binding compounds may be screened or assayed for their ability to bind to the BIR domain of IAPs. IAP binding molecules with greater binding ability than the naturally-occurring Smac, or IAP binding molecules that can release sequestered Smac from IAP in cells can be identified by such an assay. These compounds may be developed as therapeutic agents, pharmaceutical compositions for the modification, and preferably the promotion, of apoptosis in treatment of diseases or pathological conditions in which cell proliferation plays a role. These identified compounds may be used as prophylactics and can also be modified to include detectable labels or toxic agents. The assay may be further used in high throughput screening of large panels of compounds generated by combinatorial chemistry or other avenues of rational drug design. The fluorescence assay can be used to test the binding of a library of IAP binding cargo molecules modeled on the binding of Smac and its homologs, and preferably the binding of Smac N-terminus, to the surface pocket of the BIR3 region of XIAP. The results of such screening make it possible to parse the contribution of each moiety in the structure of the IAP binding cargo molecule to the total binding of the interaction. For example, by comparing the binding, $K_d$, of molecules (5-54) and (5-55) in Table 5 for different sized alkyl groups for $R_{1b}$, the contribution of methylene group to the IAP binding $K_d$, can be used to make further modifications to the molecules.

The present invention features, IAP binding compounds and methods of their use for binding to Inhibitor of Apoptosis Proteins (IAPs), including but not limited to XIAP, c-IAP1, c-IAP2, survivin, ML-IAP or combinations of these. One function of IAPs is to suppress programmed cell death, whereas Smac, or IAP binding compounds of structure (2), (3), or (5) can be used to relieve that suppression. The mammalian IAP binding protein Smac is dependent upon binding of its N-terminal four residues to a featured surface groove in a portion of XIAP referred to as the BIR3 domain. This binding prevents XIAP from exerting its apoptosis-suppressing function with caspases in the cell. An IAP binding cargo molecule, such as those of formula (2), (3), or (5), may be used to relieve XIAP-mediated or other IAP-mediated suppression of apoptosis in mammalian cells and can optionally provide a functional group having a detectable property or a therapeutic function to the cell. IAP binding cargo molecule, such as those of formula (2), (3), or (5), may be used or to release sequestered proteins like Smac from IAPs in cells.

One embodiment of the invention is a method of using versions of IAP binding compounds of formula (2), (3), or (5) that can include administering to abnormal cells or tissue, which may be known to overexpress IAP as well as other cell lines related to developmental disorders, cancer, autoimmune diseases, as well as neuro-degenerative disorders such as but not limited to for example SK-OV-3 cells, HeLa cells, or other cells, an amount of the LIP binding compounds or IAP binding cargo molecules in various embodiments of formula (2), (3), or (5) that is effective to reduce, eliminate, or otherwise treat the sample of cells. An amount of the IAP binding compounds or IAP binding cargo molecules in various embodiments of formula (2), (3), or (5) can be administered to normal cells or tissue as a control. The amount of compound of formula (2), (3), or (5), combinations of these, or combinations that include other therapeutic compounds that are effective to reduce the proliferation condition can be determined from changes in the optical density of treated and control cell or tissue samples. The administered compound of structure (2), (3), or (5), in some embodiments include those with an $EC_{50}$ as measured using the method described, for example, in Example 1 for the IAP binding compounds of less than about 1 micromolar, in other embodiments an $EC_{50}$ of less than about 0.5 micromolar, and in still other embodiments the $EC_{50}$ for the administered IAP binding compounds of structure (2), (3), or (5) can be less than about 0.06 micromolar.

The term IAP binding compound refers to a molecule that provides tertiary binding or activity with the BIR-containing protein's functional domain (e.g., binding motif or active site) of an IAP. These IAP binding compounds can be non-peptide agents such as small molecule drugs of structure (2), (3), or (5) or that include molecules of structure (2), (3), or (5). Knowing the structural features and bonding of naturally-occurring IAP-binding cargo molecules such as Smac and its homologs, it is advantageous to make IAP binding compounds that have similar or improved binding compared to the core IAP-binding N-terminal tetrapeptides of Smac and its homologs. One added advantages of IAP binding cargo molecules of structure (2), (3), or (5) in various embodiments of the invention is that compounds of this size and structure can be prepared by large scale syntheses, they can be chemically modified to have improved solubility in aqueous solution, have improved cell permeance, and provide ease of delivery to selected targets in vivo.

IAP-binding cargo molecules of the invention can include amino acids as well as molecules where the amino acids are modified to produce IAP binding compounds by elimination, replacement or modification, of one or more naturally occurring side chains of the genetically encoded amino acids. Replacement can include exchange of one or more of the L amino acids with D amino acids. Where the naturally occurring side chains of the amino acids are replaced, groups such as alkyl, lower alkyl, cyclic 4-, 5-, 6-, to 7-membered alkyl, amide, lower alkyl amide, di(lower alkyl) amide, lower alkoxy, hydroxy, carboxy and the lower ester derivatives thereof, and with 4-, 5-, 6-, to 7-membered heterocyclics can be used. For example, proline analogs can be made in which the ring size of the proline residue is changed from 5 members to 4, 6, or 7 members or substituents are added at various positions (2, 3, 4, or 5) on the ring. For example in the structure of formula (2), the substituents may be an ester group $R_2$, or an aryloxy group Z. Cyclic groups can be saturated or unsaturated, and if unsaturated, can be aromatic or non-aromatic. Heterocyclic groups may be used in as a side group in $R_2$ in the molecules of formula (2), (3), or (5). The heterocyclics can contain one or more nitrogen, oxygen, and/or sulphur heteroatoms. Examples of such heterocyclic groups include the furazanyl, furyl, imidazolidinyl, imidazolyl, imidazolinyl, isothiazolyl, isoxazolyl, morpholinyl (e.g. morpholino), oxazolyl, piperazinyl (e.g. 1-piperazinyl), piperidyl (e.g. 1-piperidyl, piperidino), pyranyl, pyrazinyl, pyrazolidinyl, pyrazolinyl, pyrazolyl, pyridazinyl, pyridyl, pyrimidinyl, pyrrolidinyl (e.g. 1-pyrrolidinyl), pyrrolinyl, pyrrolyl, thiadiazolyl, thiazolyl, thienyl, thiomorpholinyl (e.g. thiomorpholino), and triazolyl. These heterocyclic groups can be substituted or unsubstituted. Where a group is substituted, the substituent can be alkyl, alkoxy, halogen, oxygen, or substituted or unsubstituted phenyl. The IAP binding compounds may also have amino acid residues that have been chemically modified by phosphorylation, sulfonation, biotinylation, or the addition or removal of other moieties.

A variety of synthetic techniques known to those skilled in the art are available for constructing IAP binding compounds with the same or similar desired biological activity as the corresponding native peptide but with more favorable activity than the peptide with respect to solubility, stability, cell permeability, immunogenicity, and/or susceptibility to hydrolysis or proteolysis. These IAP binding cargo molecules are synthetic compounds having a three-dimensional structure (i.e. a "peptide motif") based upon the three-dimensional structure of a selected Smac peptide or homolog. The peptide motif provides the IAP binding compound with the desired biological activity, i.e., binding to IAP, wherein the binding activity of the IAP binding compound compound is not substantially reduced, and is often the same as or greater than the activity of the native peptide on which the IAP binding compound is modeled. IAP binding cargo molecules of the present invention, can have additional beneficial characteristics that enhance their therapeutic application, such as decrease cost for synthesis, increased cell permeability, enhanced stability to radiological elements, greater affinity and/or avidity for target IAPs, and prolonged biological half-life.

In one class of IAP binding compounds, the backbone can include various chemical bonds such as ester, thioester, thioamide, retroamide, reduced carbonyl, dimethylene and ketomethylene bonds, to modify IAP binding in the IAP binding cargo compounds.

Because caspases are cytosolic enzymes, diagnostic, imaging, prophylactic, and therapeutic IAP binding cargo molecules that chemically bind with the IAP proteins preferably cross cell membranes. The cell membrane-permeant IAP binding cargo molecule complexes of the present invention are preferably those that can confer the desired intracellular translocation and IAP binding properties to the IAP binding cargo molecules. Preferably, these IAP binding cargo molecules are characterized by their ability to confer transmembrane translocation and internalization of a complex IAP binding cargo molecule of structure (2), (3), or (5) when administered to the external surface of an intact cell, tissue or organ. The ability of the IAP binding cargo molecules of the present invention to permeate the cell and become localized within cytoplasmic and/or nuclear compartments may be demonstrated by a variety of detection methods such as, for example, fluorescence microscopy, confocal microscopy, electron microscopy, autoradiography, or immunohistochemistry.

Without wishing to be bound by theory, the IAP binding cargo molecule of structure (2), (3), or (5) can bind to IAPs in the cell and can but is not limited to competitively displacing IAPs bound to a caspases in the cells or releasing Smac sequestered with IAPs in the cells. The IAP binding cargo molecule chemically, physically, or by a combination of these, binds to an IAP protein and may displace it from a mature caspase or Smac protein in a cell. The physical interaction between the IAP binding portion of the IAP binding cargo molecule and an IAP protein can be used to modify apoptosis in cells.

IAP binding molecules or cargo molecules of formula (2), (3), or (5) can have an IAP binding portion which can, for example, displace a molecule or polypeptide such as a mature caspase or fluorescently labeled peptide (AbuRPF-K(5-Fam)-NH$_2$) from the BIR domain of an IAP. Where an increase in apoptosis in cells is desirable, IAP binding molecules of formula (2), (3), or (5) having a binding constant $K_d$ as measured by the methods described, for example, in Example 1 for the displacement of (AbuRPF-K(5-Fam)-NH$_2$) from the BIR domain of an IAP can be less than about 10 µM, in some embodiments $K_d$ can be less than about 1 µM, and in still other embodiments $K_d$ can be less than 0.1 micromolar under the assay conditions described in the examples.

The labeled IAP-binding cargo molecule of structure (2), (3), or (5) may include any suitable detectable label, including fluorophores, chromophores, fluorescent nanoparticles, and other dyes, isotopes, radioisotopes, metals, small molecules and the like. Where the label is linked or bonded to the IAP binding portion of the molecule, the label preferably does not interfere substantially with the cell permeance or binding of the molecule to IAP and permits its use in diagnostic or therapeutic applications. In selecting a label, preferably a detectable property of the label changes with the binding of the IAP binding cargo molecule to the BIR domain of an IAP protein. The detectable property of the label may change because the interaction of the label with the cellular environment changes when the molecule binds to IAP thereby enhancing or diminishing the property.

IAP-binding cargo molecules can also find utility as therapeutic agents. In one instance the binding of the IAP binding cargo molecule to IAP in cells can be used to modify apoptosis in cells in need of treatment. In another instance, an IAP binding cargo molecule where the cargo portion is radiolabeled may be used for radiation therapy. Through the use of these cargo molecules, radioactive atoms may be administered to a tumor, tissue, or other population of cancer cells that overexpress IAP protein. The IAP in the tumor becomes bonded to the IAP binding cargo molecule with the radionuclei. Similarly, IAP-binding cargo molecules may be designed to incorporate a dye that is active in photodynamic therapy. Other such therapeutic utilities will be apparent to those skilled in the art.

Cells being evaluated to detect abnormal levels of IAP in the cells may be mixed and optionally incubated with an IAP binding cargo molecule in a fluid sample in a vessel or wells, a flowing fluid, or fluids following purification. These samples may be monitored for changes in a detectable property of the IAP binding cargo molecule. For example, flow cytometry is a method for analyzing cells labeled with a fluorescent probe molecule on a flow cytometer. In a flow cytometer the cells pass single-file through a focused laser beam where they emit fluorescence from the probe within the cell that can be detected by the photomultiplier tubes of the cytometer. Cells with abnormal expression, high or low, of IAP may be contacted and optionally incubated with IAP binding cargo molecules of structure (2), (3), or (5) having a fluorescent probe cargo portion. The binding of the IAP binding cargo molecules to the IAP protein in the cells may be detected by the flow cytometer. The intensity of the fluorescence emission can be measured, digitized, and stored on a computer disk for analysis and comparison to the fluorescent emission from control cells, samples of cells being treated, or other cell samples whose IAP expression is to be determined.

A method of screening for IAP proteins in cells with a molecule that binds the BIR domain in an IAP protein is provided. The method includes combining an IAP binding cargo molecule of formula (2), (3), or (5) and the IAP proteins from cells, under conditions wherein the IAP binding cargo molecule and IAP protein can combine. It may include the step of incubating a sample of cells with an IAP binding cargo molecule. IAP binding by the molecule, an indication of the presence of IAP in the cells may be determined by monitoring a detectable binding property of the IAP binding cargo molecule. A change in the detectable property of the IAP binding molecule may be used to determine the expression of IAP in the cells. Where IAP protein is over expressed in cells, the IAP binding cargo molecule can be used to bind the IAP and relieve IAP-mediated inhibition of caspase activity in the cell. Alternatively, where an IAP protein sequesters a protein like Smac or other protein involved in apoptosis, the IAP binding cargo molecule of structure (2), (3), or (5) can be used to release the sequestered Smac or other protein from the IAP and modify apoptosis within the cells. Where desirable or necessary in a course of treatment, other IAP binding cargo molecules may be administered to the cells. These additional IAP binding cargo molecules may have different binding affinity for the IAP and may optionally include a cargo portion that is a therapeutic agent such as a radioisotope.

The IAP-binding cargo molecules, for example those of formula (2), may be utilized in various assays to screen for and identify compounds capable of acting as agonists or antagonists of the IAP-caspase protein or IAP-Smac interactions within cells. For example, IAP binding cargo molecules which can disrupt IAP-caspase interaction, antagonists of this interaction, are expected to be useful as pro-apoptotic drugs for treatment of cell proliferative diseases such as cancer. Agonists of this interaction may be useful as anti-apoptotic drugs for treatment of diseases where inhibition of apoptosis is needed, e.g., degenerative diseases such as Alzheimer's disease.

A living system may include plants, animals, single and multicellular organisms, and insects. The term mammal includes humans and all domestic and wild animals, including, without limitation, cattle, horses, swine, sheep, goats, dogs, cats, and the like.

An effective amount refers to that amount of a an IAP binding cargo molecule of formula (2), (3), or (5) of the present invention which, when administered to a sample of one or more cells including a tissue, or a living system such as an animal, preferably a mammal, in need thereof, is sufficient to effect detection of IAP in tissue or cells, prophylaxis of tissue or cells, or therapeutic treatment of IAP in the cells or tissue, preferably those in a living system. For disease-states alleviated by the inhibition of IAP activity, the amount of a compound of the present invention which constitutes a therapeutically effective amount that modifies or promotes apoptosis in one or more cells including a tissue, or a subject will vary depending on the compound, the disease-state and its severity, and the mammal to be treated, but can be determined routinely by one of ordinary skill in the art having regard to his own knowledge and to this disclosure. A diagnostically effective amount is an amount of an IAP binding cargo molecule sufficient to permit detection of IAP in cells or tissue and may for example vary depending upon the location of the cell or tissue and the stability of the IAP binding-cargo molecule. A prophylactically effective amount is an amount of an IAP binding cargo molecule that prevents the occurrence of a disease state and may be determined for example by prophylactic administration of IAP binding cargo molecules to cells, tissue, or test animals with controls and then exposing these to conditions known to induce abnormal cellular proliferation and then determining the prophylactically effective amount of the IAP binding cargo molecule.

Treating or treatment of a disease-state in a sample of cells, a tissue, a mammal, and particularly in a human can include detecting the presence of disease in the cells using compounds of structure (2), (3), or (5) of the present invention and where a disease is detected, optionally followed by administration of compounds of the present invention to the one or more cells, to an animal or tissue including human subjects, to modify and preferably promote apoptosis. The disease-state in the case of over expression of IAP proteins in cells may be alleviated by the inhibition of an IAP-caspase interaction or an IAP-Smac interaction by administering IAP binding cargo molecules of the present invention to the cells thereby causing regression of the disease-state. The treatment can also include: preventing the disease-state from occurring in a mammal. For example, in a mammal that is predisposed to a disease-state characterized by inhibition of apoptosis, but the mammal has not yet been diagnosed as having the disease; an effective amount of the IAP binding compounds of the present invention may be administered to cells or the patient to inhibit the disease-state or arrest its development.

In one embodiment, molecules of structure (2), (3), of (5) can be administered as a composition to provide systemic distribution of the IAP binding molecules such as by oral, buccal or parenteral administration in the mammal or human. The administration can be included in a method of treating mammals, especially humans, suffering from a proliferation disorder or that are at risk of a proliferation disorder. "At risk" refers to mammals like persons whose genotype, family history, or other risk factors indicates a greater than normal likelihood that the person will suffer from a proliferation disorder if left untreated.

The expression of IAP in cells can be detected in patients without the need for surgery. Accordingly, the present invention encompasses compounds and methods for detecting intracellular biochemical activities in living systems such as, whole animals, tissues, or cells, by administering IAP binding cargo molecules of this invention which translocate into cells, and which are detectable in living cells at distances removed from the cells by the presence of intervening tissue. The methods and compositions can be used for identifying cells or tissue having abnormal expression of IAP in a combination of one or more cells or tissues; and administering an effective amount of an IAP-binding cargo molecule to bind with the IAP in the sample cells and modify the activity of the IAP in the cells or tissue. Examples of tissues to which the methods and compositions of the present invention can be applied include, for example, cancer cells, in particular, central nervous system tumors, breast cancer, liver cancer, lung, head and neck cancer, lymphomas, leukemias, multiple myeloma, bladder cancer, ovarian cancer, prostate cancer, renal tumors, sarcomas, colon and other gastrointestinal cancers, metastases, and melanomas. Other examples of diseases, conditions or disorders where modification of apoptosis or abnormal IAP activity are involved and to which the methods and compositions of the present invention can be applied include, but are not limited to infection, inflammation, neurodegenerative diseases such as Alzheimer disease and Parkinson's disease. A proliferation disorder may include a disorder in which IAP activity inhibits apoptosis in cells receiving an apoptotic stimulus.

Apoptosis may be promoted in a sample of cells by administering to the cells an amount of an IAP-binding cargo molecule effective to stimulate apoptosis in the cells. The cells may be cultured cells, cells from within a tissue, and the tissue preferably is located within a living organism, preferably an animal, more preferably a mammal, and most preferably a human. These latter embodiments are carried out by formulating the IAP-binding cargo molecules of the invention in a therapeutically effective amount as a pharmaceutical preparation for administration to a mammalian subject. Such a pharmaceutical preparation constitutes another aspect of the present invention.

The ability of a pharmaceutical agent to simulate or inhibit apoptosis may be tested in a cell-free activity assay of downstream targets of IAP. In the absence of an IAP-binding cargo molecule, IAP itself can for example interact with Smac or inhibit the activity of caspases, thereby arresting apoptosis. Such assays include, but are not limited to, direct caspase-9 activity assays and caspase activation assays (cleavage of procaspases). In these assays, an IAP-binding cargo molecule of the invention, having a pre-determined level of activity in such assays, is used as a positive control and, optionally, a corresponding molecule known not to be active in the assay is used as a negative control. Assays can be conducted using these controls, and the cells undergoing the treatment evaluated on relief of inhibition of Smac or caspase activity by IAP in the presence of the IAP binding cargo molecule of structure (2), (3), or (5). Cells that undergo apoptosis can be differentiated from normal cells by distinct morphological changes or by molecular markers, such as cleavage of chromosomes into nucleosome ladders (detected by nuclear DNA staining).

Pharmaceutically active or biologically active IAP binding cargo molecules of the invention are those that bind IAP (inhibitor of apoptosis protein), specifically the BIR domain of IAP, more specifically the BIR3 binding groove of XIAP.

This biological activity may be measured with respect to any IAP, including but not limited to XIAP, c-IAP1, c-IAP2, survivin, ML-IAP, and DIAP.

Various aspects of the present invention will be illustrated with reference to the following non-limiting examples.

EXAMPLE 1

Binding constants ($K_d$) were measured using fluorescence polarization as described by Zaneta Nikolovska-Coleska, Renxiao Wang, Xueliang Fang, Hongguang Pan, York Tomita, Peng Li, Peter P. Roller, Krzysztof Krajewski, Naoyuki Saito, Jeanne Stuckey and Shaomeng Wang, in "Development and Optimization of a Binding Assay for the XIAP BIR3 Domain Using Fluorescence Polarization", *Analytical Biochemistry* 2004, 332,261-273). Briefly, test IAP binding compounds at various concentrations for binding measurements were mixed with 5 nM fluorescently labeled peptide (AbuRPF-K(5-Fam)-NH$_2$) and 40 nM of XIAP-BIR3 for 15 minutes at room temperature in 100 μL of 0.1M Potassium Phosphate buffer, pH 7.5 containing 100 μg/ml bovine γ-globulin. Following incubation, the polarization values (mP) were measured on a Victor$^2$V using a 485 nm excitation filter and a 520 nm emission filter. IC$_{50}$ values were determined from the plot using nonlinear least-squares analysis using GraphPad Prism. The $K_d$ values of competitive inhibitors were calculated using the equation described by by Zaneta Nikolovska-Coleska et al. based upon the measured IC$_{50}$ values, the $K_d$ value of the probe and XIAP BIR3 complex, and the concentrations of the protein and probe in the competition assay. In various examples of IAP binding or IAP binding cargo molecules ranges for $K_d$ values: Group A: $K_d$<0.1 μM; Group B: $K_d$=0.1-1 μM; Group C: $K_d$=1-10 μM; Group D: $K_d$>10 μM.

EXAMPLE 2

This example illustrates use of compounds of embodiments of the present invention that can be used in a method of treating cells. The method using these IAP binding compounds can include administering to abnormal cells, which may be known to overexpress IAP as well as other cell lines related to developmental disorders, cancer, autoimmune diseases, as well as neuro-degenerative disorders such as but not limited to for example SK-OV-3 cells, HeLa cells or other cells, an amount of the IAP binding compounds or IAP binding cargo molecules in various embodiments of formula (2), (3), or (5) that is effective to reduce, eliminate, or otherwise treat the sample of cells.

The MTT assay is an example of an assay that has been used for measuring cell growth as previously described (Hansen, M. B., Nielsen, S. E., and Berg, K. *J. Immunol. Methods* 1989, 119, 203-210) and incorporated herein by reference in its entirety. Briefly, SK-OV-3 cells were seeded in 96-well plates in McCoy's medium containing 10% fetal bovine serum albumin (20,000 per well) and incubated overnight at 37° C. Next day, test compounds were added at various concentrations typically from about 10 to about 0.0001 μM and the plates were incubated at 37° C. for an additional 72 hrs. This incubation time was optimal for measuring inhibitory effects of different analogs. 50 microliters of 5 mg/mL MTT reagent to each well was added and the plates were incubated at 37° C. for 3 hours. At the end of incubation period, 50 microliters of DMSO was added to each well to dissolve cells and the optical density (OD) of the wells was measured with a microplate reader (Victor$^2$ 1420, Wallac, Finland) at 535 nm. Cell survival (CS) was calculated by the following equation:

$$CS = (OD\text{ treated well/mean }OD\text{ control wells}) \times 100\%$$

The EC$_{50}$, defined as the drug concentration that results in 50% CS, was derived by calculating the point where the dose-response curve crosses the 50% CS point using GraphPad Prism.

Representative results for IAP binding compounds are:

TABLE 1

(E2)

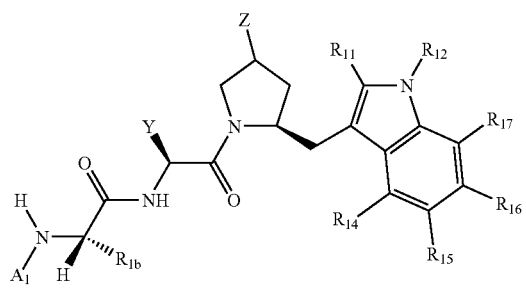

| Entry | A$_1$ | R$_{1b}$ | Y | Z | R$_{12}$ | R$_{14-17}$ | R$_{11}$ | EC$_{50}$, μM (±sd) |
|---|---|---|---|---|---|---|---|---|
| 1-1 | Me | Me | tBu | H | MeO(CH$_2$CH$_2$O)$_2$CH$_2$CH$_2$ | 6-F (R$_{16}$) | H | 0.092 ± 0.077 |
| 1-2 | Me | Me | cHex | H | MeO(CH$_2$CH$_2$O)$_2$CH$_2$CH$_2$ | 6-F (R$_{16}$) | H | 0.060 ± 0.026 |
| 1-3 | Me | Me | cHex | H | H | 6-F (R$_{16}$) | H | 0.515 ± 0.093 |

EXAMPLE 3

This example illustrates the preparation of pyrrolidine derivatives of Table 2. The examples include molecules of formula (E3) that can include heteroalkynyl substituents.

Scheme I

The Preparation of 2S-Amino-N-[2-methyl-1S-(4S-phenoxy-2S-phenoxymethyl-pyrrolidine-1-carbonyl)-propyl]-propionamide hydrochloride (7)

A. (4S)-Phenoxy-(2S)-phenoxymethyl-pyrrolidine-1-carboxylic acid tert-butyl ester (2): To a solution of alcohol 1 (0.53 g, 1.8 mmol) in anhydrous DCM (10 mL) was added phenol (0.21 g, 2.3 mmol), $Ph_3P$ (0.52 g, 2.0 mmol), and 1,1'-(azodicarbonyl)-dipiperidine (ADDP, 0.50 g, 1.9 mmol) in sequential order. After 2 hr at ambient temperature, the heterogeneous reaction mixture was filtered. The white solid was washed with DCM and the clarified filtrate was washed with 2M NaOH, water, brine, dried with anhydrous $Na_2SO_4$, filtered and concentrated. The crude aryl ether was purified by flash silica gel chromatography (3:1 hexane/EtOAc) to afford 0.36 g (54%) of 2 as a colorless oil. $^1$H NMR ($CDCl_3$, 300 MHz) δ 7.29-7.24 (m, 4H), 6.94-6.82 (m, 6H), 4.91 (t, J=5.1 Hz, 1H), 4.37-4.28 (m, 2H), 4.12-4.05 (m, 1H), 3.79-3.64 (m, 2H), 2.48 (app d, J=13.8 Hz, 1H), 2.32-2.25 (m, 1H), 1.48 (s, 9H) ppm.

B. (4S)-Phenoxy-(2S)-phenoxymethyl-pyrrolidine (3): Trifluoroacetic acid (2 mL) was added at ambient temperature to a solution of 2 (0.36 g, 0.98 mmol) in DCM (10 mL). After 1.5 h, the solution was concentrated to dryness and the crude product was dissolved in EtOAc. The organic solution was washed with aqueous $NaHCO_3$, brine, dried over anhydrous $Na_2SO_4$, filtered, and concentrated. The crude pyrrolidine was purified by flash silica gel chromatography (10% MeOH/DCM) to afford 0.23 g (88%) of 3 as a brown-orange oil. $^1$H NMR ($CDCl_3$, 300 MHz) δ 7.32-7.26 (m, 4H), 6.98-6.87 (m, 6H), 4.90-4.87 (m, 1H), 4.07-4.01 (m, 2H), 3.63-3.57 (m, 1H), 3.35 (app d, J=12.3 Hz, 1H), 3.17 (app q, J=5.4 Hz, 1H), 2.77 (br s, 1H), 2.45-2.35 (m, 1H), 1.93-1.86 (m, 1H) ppm.

C. [2-Methyl-1-(4S-phenoxy-2S-phenoxymethyl-pyrrolidine-1-carbonyl)-propyl]-carbamic acid tert-butyl ester (4): O-(7-Azabenzotriazol-1-yl)-N,N,N',N'-tetramethyluronium $PF_6$ (HATU, 0.38 g, 1.0 mmol) was added to a solution of N-Boc-Val (0.28 g, 1.3 mmol) in anhydrous NMP (5 mL) at ambient temperature. N-Methylmorpholine (0.1 mL) was added to reaction mixture. After 10 min, pyrrolidine 3 (0.23 g, 0.86 mmol) in NMP (5 mL) was added. After 2 h, the reaction mixture was diluted with EtOAc and washed with dilute aqueous $NaHCO_3$, 1N HCl, water, and brine. The organic phase was dried over anhydrous $Na_2SO_4$, filtered and concentrated. The crude amide was purified by flash silica gel chromatography (3:1 hexane/EtOAc) to afford 0.36 g (90%) of 4 as a colorless oil. $^1$H NMR ($CDCl_3$, 300 MHz) δ 7.34-7.26 (m, 4H), 7.03-6.82 (m, 6H), 5.30 (d, J=9.3 Hz, 1H), 5.01-4.99 (m, 1H), 4.69-4.65 (m, 1H), 4.38-4.34 (m, 1H), 4.27-4.07 (m, 3H), 3.83-3.78 (m, 1H), 2.53-2.48 (m, 1H), 2.38-2.31 (m, 1H), 2.00-1.94 (m, 1H), 1.48 (s, 9H), 0.97 (d, J=7.2 Hz, 3H), 0.93 (d, J=7.2 Hz, 3H) ppm.

D. 2-Amino-3-methyl-1-(4S-phenoxy-2S-phenoxymethyl-pyrrolidin-1-yl)-butan-1-one (5): Trifluoroacetic acid (2 mL) was added at ambient temperature to a solution of 4 (0.36 g, 0.79 mmol) in DCM (10 mL). After 1.5 h, the solution was concentrated to dryness and the crude product was dissolved in EtOAc. The organic solution was washed with aqueous $NaHCO_3$, brine, dried over anhydrous $Na_2SO_4$, filtered, and concentrated. The crude amine was purified by flash silica gel chromatography (5% MeOH/DCM) to afford 0.27 g (96%) of 5 as a light yellow oil. $^1$H NMR ($CDCl_3$, 300 MHz) δ 7.32-7.01 (m, 4H), 7.01-6.82 (m, 6H), 4.99 (m, 1H), 4.67-4.48 (m, 1H), 4.38-4.27 (m, 1H), 4.16-4.05 (m, 1H), 3.99 (app q, J=5.1 Hz, 1H), 3.78-3.72 (m, 1H), 2.50-2.28 (m, 2H), 1.86 (br s, 2H), 0.97 (d, J=7.2 Hz, 3H), 0.91 (d, J=7.2 Hz, 3H) ppm.

E. {1S-[2-Methyl-1S-(4S-phenoxy-2S-phenoxymethyl-pyrrolidine-1-carbonyl)-propylcarbamoyl]-ethyl}-carbamic acid tert-butyl ester (6): O-(7-Azabenzotriazol-1-yl)-N,N,N',N'-tetramethyluronium $PF_6$ (HATU, 0.23 g, 0.61 mmol) was added to a solution of N-Boc-Ala (0.14 g, 0.74 mmol) in anhydrous NMP (3 mL) at ambient temperature. N-Methylmorpholine (0.1 mL) was added to reaction mixture. After 10 min, pyrrolidine 5 (0.17 g, 0.48 mmol) in NMP (5 mL) was added. After 16 h, the reaction mixture was diluted with EtOAc and washed with dilute aqueous $NaHCO_3$, 1N HCl, water, and brine. The organic phase was dried over anhydrous $Na_2SO_4$, filtered and concentrated. The crude amide was purified by flash silica gel chromatography (1:1 hexane/EtOAc) to afford 0.23 g (92%) of 6 as a colorless oil. $^1$H NMR ($CDCl_3$, 300 MHz) δ 7.33-7.23 (m, 4H), 7.02-6.87 (m, 6H), 5.02-4.99 (m, 2H), 4.68-4.48 (m, 2H), 4.33 (dd, J=3.9, 9.3 Hz, 1H), 4.23-4.09 (m, 4H), 3.83-3.78 (m, 1H), 2.52-2.47 (m, 1H), 2.38-2.28 (m, 1H), 2.08-1.99 (m, 1H), 1.80 (br s, 1H), 1.45 (s, 9H), 1.36 (d, J=6.9 Hz, 3H), 0.95 (d, J=6.9 Hz, 3H), 0.90 (d, J=7.0 Hz, 3H) ppm.

F. 2S-Amino-N-[2-methyl-1S-(4S-phenoxy-2S-phenoxymethyl-pyrrolidine-1-carbonyl)-propyl]-propionamide hydrochloride (7): Trifluoroacetic acid (2 mL) was added at ambient temperature to a solution of 6 (0.23 g, 0.44 mmol) in DCM (10 mL). After 1.5 h, the solution was concentrated to dryness and the crude product was dissolved in EtOAc. The organic solution was washed with aqueous $NaHCO_3$, brine, dried over anhydrous $Na_2SO_4$, filtered, and concentrated. The crude amine was dissolved in diethyl ether then treated with HCl(g). The crude salt was triturated with diethyl ether and hexane to afford 0.13 g (65%) of 7 as a white solid. $^1$H NMR, free base ($CDCl_3$, 300 MHz) δ 7.89-7.87 (m, 1H), 7.32-7.24 (m, 4H), 7.01-6.79 (m, 5H), 5.01-4.98 (m, 1H), 4.68-4.62 (m, 1H), 4.51-4.43 (m, 1H), 4.36-4.26 (m, 2H), 4.18-4.10 (m, 1H), 3.84-3.78 (m, 1H), 2.51-2.46 (m, 1H), 2.35-2.28 (m, 1H), 2.09-2.02 (m, 1H), 1.38-1.25 (m, 4H), 0.96-0.92 (m, 6H) ppm. Mass spectra, m/z=440 [(M+H)$^+$].

TABLE 2
(E3)
| Entry | $A_1$ | $R_{1b}$ | Y | Z | $R_{3-5}$, $R'_{3-5}$, $R_4$ | MS $(M+H)^+$ | $K_D$ Range |
|---|---|---|---|---|---|---|---|
| 2-1 | H | Me | iPr | (S)-OPh | H | 440.3 | B |
| 2-2 | Me | Me | iPr | (S)-OPh | H | 454.3 | B |
| 2-3 | H | Me | iPr | H | H | 348.3 | B |
| 2-4 | H | Me | iPr | H | 2,3-$(CH_2)_4$ | 402.3 | B |
| 2-5 | Me | Me | iPr | H | 2-Ph | 438.3 | B |
| 2-6 | H | Me | iPr | H | 2-Ph | 424.2 | B |
| 2-7 | H | Me | —CH(Me)OCH$_2$C≡CH | (S)-OPh | H | 480.2 | A |
EXAMPLE 4
This example illustrates the preparation of substituted pyrrolidines of Table 3.
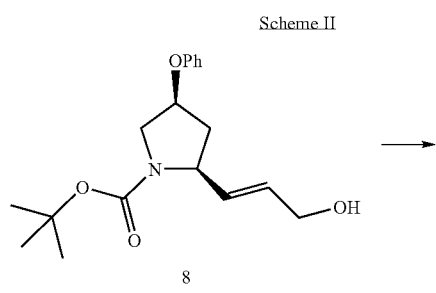
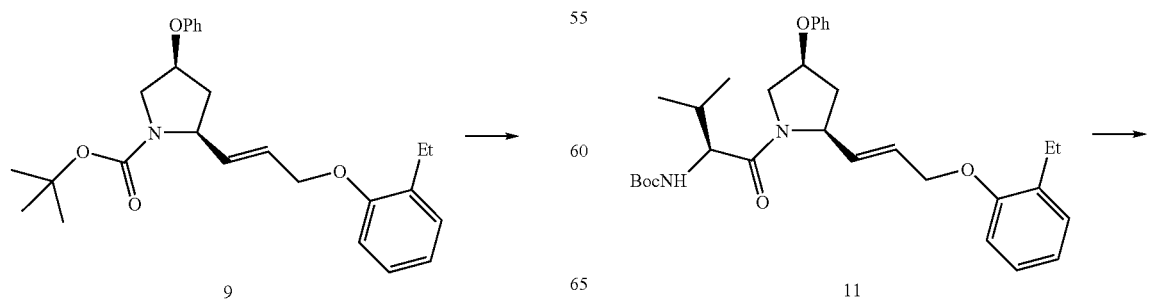

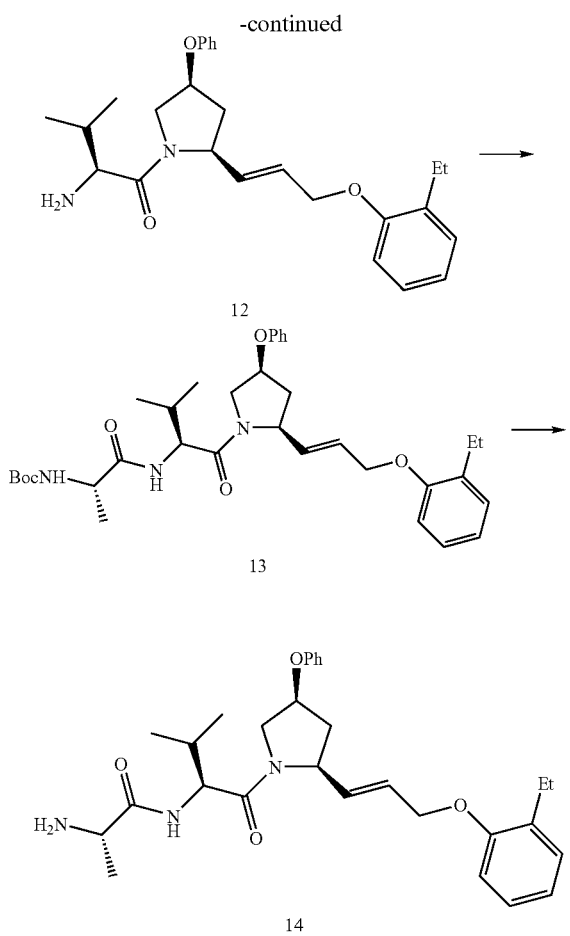

The Preparation of trans-2S-Amino-N-(1S-{2S-[3-(2-ethyl-phenoxy)-propenyl]-4S-phenoxy-pyrrolidine-1-carbonyl}-2-methyl-propyl)-propionamide (14)

A. trans-2S-[3-(2-Ethyl-phenoxy)-propenyl]-4S-phenoxy-pyrrolidine-1-carboxylic acid tert-butyl ester (9): To a solution of alcohol 8 (0.3 g, 0.94 mmol) in DCM (6 mL) was added 2-ethylphenol (0.14 g, 1.16 mmol) and $Ph_3P$ (0.27 g, 1.03 mmol). The solution was cooled to 0° C. and ADDP (0.28 g, 1.13 mmol) was added in one portion. After 10 min, the reaction mixture was allowed to warm to ambient temperature and stirring was continued for 16 h. The white precipitate was removed by filtration and washed with DCM. The clarified filtrate was washed successively with 1M NaOH, water, and brine. The organic phase was dried with anhydrous $Na_2SO_4$, filtered, and concentrated. The crude ether was purified by flash silica gel chromatography (3:1 hexane/EtOAc) to afford 0.18 g (45%) of 9 as a colorless oil. $^1$H NMR ($CDCl_3$, 300 MHz) δ 7.30-7.26 (m, 2H); 7.15 (m, 2H); 7.00-6.79 (m, 4H); 6.01-5.98 (m, 1H), 5.84 (m, 1H); 4.92 (br s, 1H); 4.53-4.43 (m, 3H); 3.76 (m, 2H); 2.65 (q, 2H); 2.39 (m, 1H); 2.16 (d, 1H); 1.46 (s, 9H), 1.21 (t, 3H) ppm.

B. trans-2S-[3-(2-Ethyl-phenoxy)-propenyl]-4S-phenoxy-pyrrolidine (10): Trifluoroacetic acid (2 mL) was added at ambient temperature to a solution of 9 (0.18 g, 0.43 mmol) in DCM (10 mL). After 1 h, the solution was concentrated to dryness and the crude product was dissolved in EtOAc. The organic solution was washed with aqueous $NaHCO_3$, brine, dried over anhydrous $MgSO_4$, filtered, and concentrated. The crude amine (10) was used without further purification (0.13 g obtained). $^1$H NMR ($CDCl_3$, 300 MHz) δ 7.31-7.25 (m, 3H); 7.17-7.11 (m, 2H); 6.97-6.80 (m, 4H); 5.97-5.88 (m, 2H); 4.86 (m, 1H); 4.54-4.50 (m, 2H); 3.70 (q, 1H); 3.34 (d, 1H); 3.07 (d of d, 1H); 2.66 (q, 2H); 2.48-2.41 (m, 1H); 1.82-1.75 (m, 2H); 1.20 (t, 3H) ppm.

C. trans-(1S-{2S-[3-(2-Ethyl-phenoxy)-propenyl]-4S-phenoxy-pyrrolidine-1-carbonyl}-2-methyl-propyl)-carbamic acid tert-butyl ester (11): O-(7-Azabenzotriazol-1-yl)-N,N,N',N'-tetramethyluronium $PF_6$ (HATU, 0.23 g, 0.62 mmol) was added to a solution of N-Boc-Val (0.18 g, 0.82 mmol) in anhydrous NMP (3 mL) at ambient temperature. N-Methylmorpholine (0.12 mL) was added to reaction mixture. After 10 min, amine 10 (0.13 g, 0.41 mmol) in NMP (3 mL) was added. After 16 h, the reaction mixture was diluted with EtOAc and washed with dilute aqueous $NaHCO_3$, 1N HCl, water, and brine. The organic phase was dried over anhydrous $Na_2SO_4$, filtered and concentrated. The crude amide was purified by flash silica gel chromatography (3:2 hexane/EtOAc) to afford 0.20 g (92%, 2 steps) of 11 as a colorless oil. $^1$H NMR ($CDCl_3$, 300 MHz) δ 7.32-7.24 (m, 2H); 7.15-7.06 (m, 2H); 6.99 (t, 1H); 6.89-6.77 (m, 4H); 5.96-5.91 (m, 2H); 5.23-5.20 (m, 1H); 5.01-4.86 (m, 2H); 4.53 (m, 2H); 4.21-4.09 (m, 2H); 4.09-3.97 (m, 1H); 2.68 (q, 2H); 2.36-2.32 (m, 1H); 2.18 (d, 1H); 1.97-1.91 (m, 1H); 1.44 (s, 9H); 1.29-1.18 (m, 6H); 0.99-0.81 (m, 6H) ppm.

D. trans-2S-Amino-1-{2S-[3-(2-ethyl-phenoxy)-propenyl]-4S-phenoxy-pyrrolidin-1-yl}-3-methyl-butan-1-one (12): Trifluoroacetic acid (2 mL) was added at ambient temperature to a solution of 11 (0.20 g, 0.39 mmol) in DCM (10 mL). After 1 h, the solution was concentrated to dryness and the crude product was dissolved in EtOAc. The organic solution was washed with aqueous $NaHCO_3$, brine, dried over anhydrous $MgSO_4$, filtered, and concentrated. The crude amine (12) was used without further purification (0.14 g obtained). $^1$H NMR ($CDCl_3$, 300 MHz) δ 7.28-7.26 (m, 2H); 7.15 (m, 2H); 6.99 (m, 1H); 6.89-6.76 (m, 4H); 6.10-5.86 (m, 2H); 5.01-4.95 (m, 2H); 4.56 (m, 3H); 3.92-3.79 (m, 1H); 3.31 (m, 1H); 2.66 (q, 2H); 2.32-2.16 (m, 1H); 1.68 (m, 4H); 1.28-1.19 (m, 3H); 0.97-0.81 (m, 6H) ppm.

E. trans-[1S-(1S-{2S-[3-(2-Ethyl-phenoxy)-propenyl]-4S-phenoxy-pyrrolidine-1-carbonyl}-2-methyl-propylcarbamoyl)-ethyl]-carbamic acid tert-butyl ester (13): O-(7-Azabenzotriazol-1-yl)-N,N,N',N'-tetramethyluronium $PF_6$ (HATU, 0.19 g, 0.51 mmol) was added to a solution of N-Boc-Ala (0.13 g, 0.67 mmol) in anhydrous NMP (3 mL) at ambient temperature. N-Methylmorpholine (0.1 mL) was added to reaction mixture. After 10 min, amine 12 (0.14 g, 0.34 mmol) in NMP (3 mL) was added. After 72 h, the reaction mixture was diluted with EtOAc and washed with dilute aqueous $NaHCO_3$, 1N HCl, water, and brine. The organic phase was dried over anhydrous $Na_2SO_4$, filtered and concentrated. The crude amide was purified by flash silica gel chromatography (1:1 hexane/EtOAc) to afford 0.11 g (49%, 2 steps) of 13 as a colorless oil. $^1$H NMR ($CDCl_3$, 300 MHz) δ 7.31-7.22 (m, 2H); 7.15-6.95 (m, 3H); 6.88-6.76 (m, 4H); 5.96-5.87 (m, 2H); 5.19 (br, 1H); 5.00 (m, 1H); 4.86 (t, 1H); 4.51-4.49 (m, 3H); 4.17-4.10 (m, 2H); 3.89-3.80 (m, 1H); 2.64 (q, 2H); 2.34-2.29 (m, 1H); 2.21-2.14 (m, 1H); 2.04-1.98 (m, 1H); 1.44 s, 9H); 1.35-1.23 (m, 4H); 1.17 (t, 3H); 0.97-0.87 (m, 6H) ppm.

F. trans-2S-Amino-N-(1S-{2S-[3-(2-ethyl-phenoxy)-propenyl]-4S-phenoxy-pyrrolidine-1-carbonyl}-2-methyl-propyl)-propionamide (14): Trifluoroacetic acid (2 mL) was added at ambient temperature to a solution of 13 (0.11 g, 0.18 mmol) in DCM (10 mL). After 1 h, the solution was concentrated to dryness and the crude product was dissolved in EtOAc. The organic solution was washed with aqueous NaHCO$_3$, brine, dried over anhydrous Na$_2$SO$_4$, filtered, and concentrated to afford 0.068 g (76%) of 14 as a white solid. $^1$H NMR (CDCl$_3$, 300 MHz) δ 7.86 (br, 1H); 7.31-7.22 (m, 2H); 7.15-7.05 (m, 2H); 6.98 (t, 1H); 6.88-6.76 (m, 4H); 5.97-5.86 (m, 2H); 5.00-4.98 (m, 1H); 4.88-4.83 (m, 1H); 4.57-4.51 (m, 2H); 4.44 (t, 1H); 4.21 (d of d, 1H); 3.89-3.82 (m, 1H); 2.64 (q, 2H); 2.33-2.29 (m, 1H); 2.17 (d, 1H); 2.04-2.00 (m, 1H); 1.36-1.25 (m, 6H); 1.17 (t, 3H); 0.99-0.88 (m, 6H) ppm.

TABLE 3

(E4)

| Entry | A$_1$ | R$_{1b}$ | Y | Z | R$_{3-5}$, R$_{3-5}$, R$_4$ | MS (M + H)$^+$ | K$_D$ Range |
|---|---|---|---|---|---|---|---|
| 3-8 | H | Me | iPr | OPh | H | 466.2 | B |
| 3-9 | H | Me | iPr | OPh | 2-Br | 544.0 | B |
| 3-10 | H | Me | iPr | OPh | 2,3-di-Cl | 534.1 | B |
| 3-11 | H | Me | iPr | OPh | 2,4-di-Cl | 534.1 | B |
| 3-12 | H | Me | iPr | OPh | 2-Et | 494.4 | B |
| 3-13 | Me | Me | iPr | OPh | 2,3-di-Cl | 548.2 | B |
| 3-14 | H | Me | iPr | OPh | 3-Br | 544.1 | B |
| 3-15 | H | Me | iPr | OPh | 2-iPrO | 524.3 | B |
| 3-16 | Boc | Me | iPr | OPh | 3,4-(CH$_2$)$_4$ | 620.3 | D |
| 3-17 | H | Me | iPr | OPh | 3,4-(CH$_2$)$_4$ | 520.3 | C |
| 3-18 | H | Me | iPr | OPh | 2-MeO | 496.3 | B |
| 3-19 | H | H | iPr | OPh | 2-MeO | 482.3 | D |
| 3-20 | H | Me | iPr | OPh | 2-Ph | 542.3 | B |
| 3-21 | H | Me | iPr | OPh | 2-cyclopentyl | 534.3 | C |
| 3-22 | H | Me | iPr | OPh | 2,6-di-Me | 494.3 | A |

EXAMPLE 5

This example illustrates the preparation of pyrrolidine derivatives of Table 4.

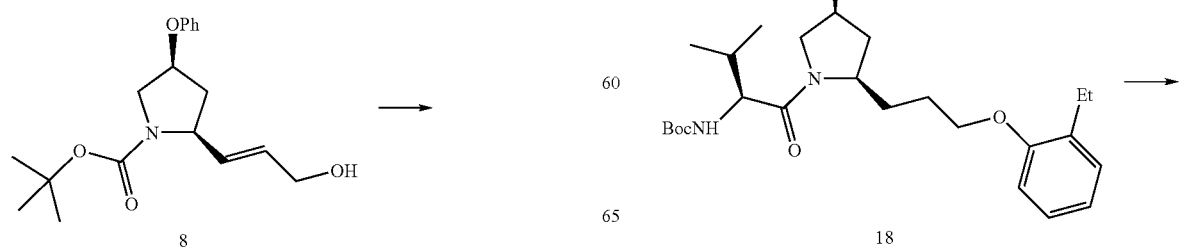

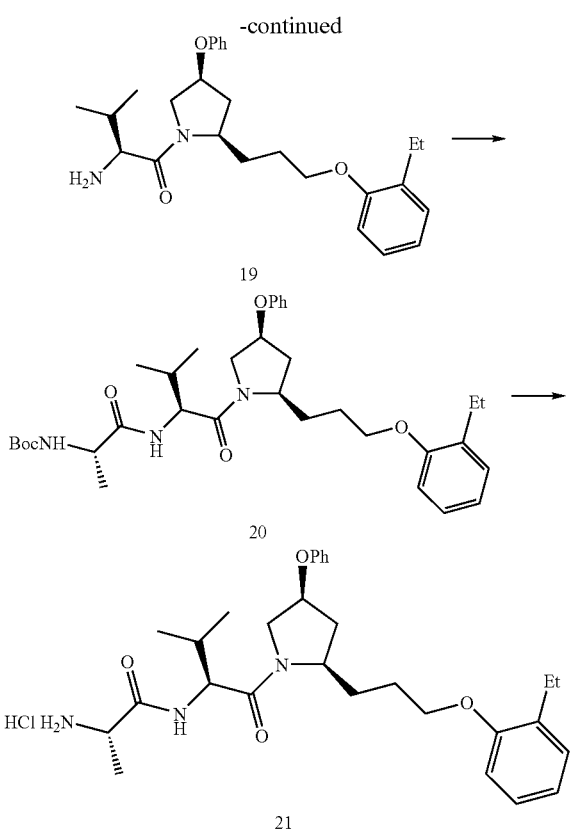

The Preparation of 2S-Amino-N-(1S-{2S-[3-(2-ethyl-phenoxy)-propyl]-4S-phenoxy-pyrrolidine-1-carbonyl}-2-methyl-propyl)-propionamide (21)

A. 2S-(3-Hydroxy-propyl)-4S-phenoxy-pyrrolidine-1-carboxylic acid tert-butyl ester (15): [Re: SRR-006-062] Palladium-on-carbon (10%, 0.3 g) was added to a solution of alcohol 8 (3 g, 9.4 mmol) in EtOAc (30 mL). The reaction mixture was placed on a Parr shaker and pressurized to 45 PSI $H_2$ (g). The heterogeneous mixture was shaken for 24 h at ambient temperature. The catalyst was removed via filtration through a 0.45 μm PVDF filter disc (Millipore Millex-HV®) and the clarified filtrate was concentrated in vacuo to afford 2.9 g (97%) of 15 which was used without further purification. $^1$H NMR (CDCl$_3$, 300 MHz) δ 7.29 (t, 2H); 6.96 (t, 1H); 6.85 (d, 2H); 4.88 (br s, 1H); 4.08-3.74 (m, 2H); 3.67-3.65 (m, 2H); 3.55 (d, 1H); 2.27-2.23 (m, 2H); 2.05-1.90 (m, 2H); 1.76-1.65 (m, 1H); 1.55 (q, 2H); 1.47 (s, 9H) ppm.

B. 2S-[3-(2-Ethyl-phenoxy)-propyl]-4S-phenoxy-pyrrolidine-1-carboxylic acid tert-butyl ester (16): To a solution of alcohol 15 (0.61 g, 1.91 mmol) in DCM (10 mL) was added 2-ethylphenol (0.28 g, 2.33 mmol) and Ph$_3$P (0.55 g, 2.09 mmol). The solution was cooled to 0° C. and ADDP (0.58 g, 2.29 mmol) was added in one portion. After 10 min, the reaction mixture was allowed to warm to ambient temperature and stirring was continued for 16 h. The white precipitate was removed by filtration and washed with DCM. The clarified filtrate was washed successively with 1M NaOH, water, and brine. The organic phase was dried with anhydrous Na$_2$SO$_4$, filtered, and concentrated. The crude ether was purified by flash silica gel chromatography (3:1 hexane/EtOAc) to afford 0.46 g of 16 as a colorless oil. $^1$H NMR (CDCl$_3$, 300 MHz) δ 7.28 (t, 2H); 7.13 (t, 2H); 6.96 (t, 1H); 6.89-6.84 (m, 3H); 6.78 (d, 1H); 4.91-4.87 (m, 1H); 3.96 (br, 4H); 3.56 (d, 1H); 2.63 (q, 2H); 2.28-2.26 (m, 1H); 2.11-2.06 (m, 2H); 1.86-1.77 (m, 3H); 1.46 (s, 9H); 1.17 (t, 3H) ppm.

C. 2S-[3-(2-Ethyl-phenoxy)-propyl]-4S-phenoxy-pyrrolidine (17): Trifluoroacetic acid (2 mL) was added at ambient temperature to a solution of 16 (0.46 g, 1.08 mmol) in DCM (10 mL). After 1 h, the solution was concentrated to dryness and the crude product was dissolved in EtOAc. The organic solution was washed with aqueous NaHCO$_3$, brine, dried over anhydrous Na$_2$SO$_4$, filtered, and concentrated to afford 0.30 g (85%) of 17 as a colorless oil. $^1$H NMR (CDCl$_3$, 300 MHz) δ 7.32-7.26 (m, 3H); 7.16-7.12 (m, 2H); 6.98 6.78 (m, 4H); 4.86 (s, 1H); 3.99-3.97 (m, 2H); 3.35 (d, 1H); 3.23 (m, 1H); 3.08 (m, 1H); 2.74-2.60 (m, 3H); 2.42 (m, 2H); 1.90-1.85 (m, 3H); 1.67-1.61 (m, 1H); 1.16 (t, 3H) ppm.

D. (1S-{2S-[3-(2-Ethyl-phenoxy)-propyl]-4S-phenoxy-pyrrolidine-1-carbonyl}-2-methyl-propyl)-carbamic acid tert-butyl ester (18): O-(7-Azabenzotriazol-1-yl)-N,N,N',N'-tetramethyluronium PF$_6$ (HATU, 0.39 g, 1.03 mmol) was added to a solution of N-Boc-Val (0.30 g, 1.38 mmol) in anhydrous NMP (3 mL) at ambient temperature. N-Methylmorpholine (0.2 mL) was added to reaction mixture. After 10 min, amine 17 (0.22 g, 0.67 mmol) in NMP (3 mL) was added. After 16 h, the reaction mixture was diluted with EtOAc and washed with dilute aqueous NaHCO$_3$, 1N HCl, water, and brine. The organic phase was dried over anhydrous Na$_2$SO$_4$, filtered and concentrated. The crude amide was purified by flash silica gel chromatography (3:1 hexane/EtOAc) to afford 0.30 g (83%) of 18 as a colorless oil. $^1$H NMR (CDCl$_3$, 300 MHz) δ 7.33-7.26 (m, 2H); 7.12 (t, 2H); 6.99 (t, 1H); 6.89-6.77 (m, 4H); 5.28-5.24 (m, 1H); 5.00-4.98 (m, 1H); 4.39-4.36 (m, 1H); 4.22-4.17 (m, 2H); 4.02-3.94 (m, 2H); 3.72 (d of d, 1H); 2.61 (q, 2H); 2.30-2.24 (m, 1H); 2.14-2.07 (, 1H); 1.98-1.89 (m, 1H); 1.82-1.74 (m, 4H); 1.44 (s, 9H); 1.18-1.13 (m, 3H); 0.99-0.93 (m, 6H) ppm.

E. 2S-Amino-1-{2S-[3-(2-ethyl-phenoxy)-propyl]-4S-phenoxy-pyrrolidin-1-yl}-3-methyl-butan-1-one (19): Trifluoroacetic acid (2 mL) was added at ambient temperature to a solution of 18 (0.30 g, 0.57 mmol) in DCM (10 mL). After 1 h, the solution was concentrated to dryness and the crude product was dissolved in EtOAc. The organic solution was washed with aqueous NaHCO$_3$, brine, dried over anhydrous Na$_2$SO$_4$, filtered, and concentrated to afford 0.23 g of 19 as a colorless oil. $^1$H NMR (CDCl$_3$, 300 MHz) δ 7.33-7.28 (m, 2H); 7.17-7.12 (m, 2H); 6.99 (t, 1H); 6.89-6.83 (m, 3H); 6.78 (d, 1H); 4.98 (br, 2H); 4.39 (br, 1H), 4.07-3.92 (m, 4H); 3.75-3.67 (m, 1H); 2.61 (q, 2H); 2.31-2.24 (m, 2H); 2.13-2.08 (m, 2H); 1.94-1.75 (m, 6H); 1.16 (t, 3H); 1.01-0.85 (m, 6H) ppm.

F. [1S-(1S-{2S-[3-(2-Ethyl-phenoxy)-propyl]-4S-phenoxy-pyrrolidine-1-carbonyl}-2-methyl-propylcarbamoyl)-ethyl]-carbamic acid tert-butyl ester (20): O-(7-Azabenzotriazol-1-yl)-N,N,N',N'-tetramethyluronium PF$_6$ (HATU, 0.11 g, 0.27 mmol) was added to a solution of N-Boc-Ala (0.07 g, 0.37 mmol) in anhydrous NMP (3 mL) at ambient temperature. N-Methylmorpholine (0.05 mL) was added to reaction mixture. After 10 min, amine 19 (0.078 g, 0.18 mmol) in NMP (1 mL) was added. After 16 h, the reaction mixture was diluted with EtOAc and washed with dilute aqueous NaHCO$_3$, 1N HCl, water, and brine. The organic phase was dried over anhydrous Na$_2$SO$_4$, filtered and concentrated. The crude amide was purified by flash silica gel chromatography (1:1 hexane/EtOAc) to afford 0.038 g of 20 as a colorless oil. $^1$H NMR (CDCl$_3$, 300 MHz) δ 7.33-7.26 (m, 2H); 7.12 (t, 2H); 6.99 (t, 1H); 6.88-6.76 (m, 4H); 5.08-5.00 (m, 1H); 4.98-4.96 (m, 1H); 4.52-4.47 (m, 1H); 4.37 4.34

(m, 1H); 4.21-4.16 (m, 2H); 3.98-3.92 (m, 2H); 3.75 (d, 1H); 2.61 (q, 2H); 2.32-2.22 (m, 1H); 2.14-1.99 (m, 4H); 1.86-1.77 (m, 3H); 1.44-1.41 (m, 8H); 1.36-1.13 (m, 4H); 1.16 (t, 3H); 0.96-0.88 (m, 6H) ppm.

G. 2S-Amino-N-(1S-{2S-[3-(2-ethyl-phenoxy)-propyl]-4S-phenoxy-pyrrolidine-1-carbonyl}-2-methyl-propyl)-propionamide (21): Trifluoroacetic acid (1 mL) was added at ambient temperature to a solution of 20 (0.038 g, 0.06 mmol) in DCM (5 mL). After 1 h, the solution was concentrated to dryness and the crude product was dissolved in EtOAc. The organic solution was washed with aqueous $NaHCO_3$, brine, dried over anhydrous $Na_2SO_4$, filtered, and concentrated. The crude amine was dissolved in diethyl ether then treated with HCl(g). The crude salt was triturated with diethyl ether and hexane to afford 0.022 g of 21 as a white solid. $^1$H NMR ($CDCl_3$, 300 MHz) δ 7.87 (br, 1H); 7.33-7.25 (m, 2H); 7.12 (t, 2H); 6.96 (t, 1H); 6.89-6.77 (m, 4H); 4.98-4.96 (m, 1H); 4.45 (t, 1H); 4.37-4.25 (m, 2H); 4.00-3.94 (m, 2H); 3.77 (d, 1H); 2.61 (q, 2H); 2.32-2.21 (m, 1H); 2.14-2.04 (m, 3H); 1.61 (br, 2H); 1.35-1.25 (m, 4H); 1.16 (t, 3H); 0.97-0.89 (m, 6H) ppm.

TABLE 4

(E5)

| Entry | $A_1$ | $R_{1b}$ | Y | Z | $R_{3-5}$, $R'_{3-5}$, $R_4$ | MS $(M+H)^+$ | $K_D$ Range |
|---|---|---|---|---|---|---|---|
| 4-23 | H | Me | iPr | OPh | 2-Br | 524.3 | B |
| 4-24 | H | Me | iPr | OPh | 2-Ph | 543.7 | B |
| 4-25 | H | Me | iPr | OPh | 2-Et | 552.4 | B |
| 4-26 | Me | Me | iPr | OPh | 2-Et | 510.3 | B |
| 4-27 | H | H | iPr | OPh | 2-Et | 482.3 | D |
| 4-28 | Me | Me | tBu | OPh | 2-Et | 524.2 | B |
| 4-29 | H | Me | iPr | OPh | 2-iPrO | 526.3 | B |
| 4-30 | H | Me | iPr | OPh | 2-iPr | 510.3 | B |
| 4-31 | H | Me | iPr | OPh | 2,6-di-Me | 496.2 | B |
| 4-32 | H | Me | iPr | H | 2-Ph | 452.3 | B |
| 4-33 | H | H | iPr | H | 2-Ph | 438.3 | D |
| 4-34 | H | Me | iPr | H | 2-Et | 404.3 | C |
| 4-35 | H | Me | iPr | H | 2-iPrO | 434.3 | C |
| 4-36 | H | (R)-Me | iPr | H | 2-Ph | 452.3 | D |
| 4-37 | H | Me | iPr | H | H | 376.3 | C |
| 4-38 | H | Me | iPr | H | 2,6-di-Me | 404.3 | D |

EXAMPLE 6

This example illustrated pyrrolidine derivatives of Table 5.

Scheme IV(a)

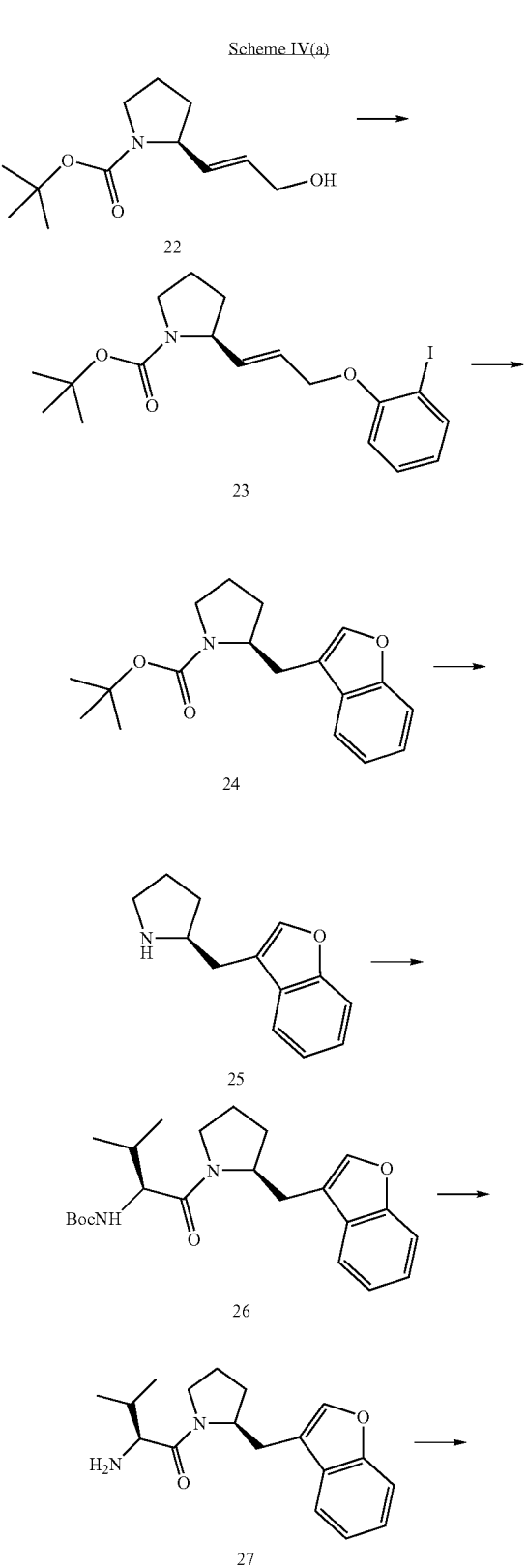

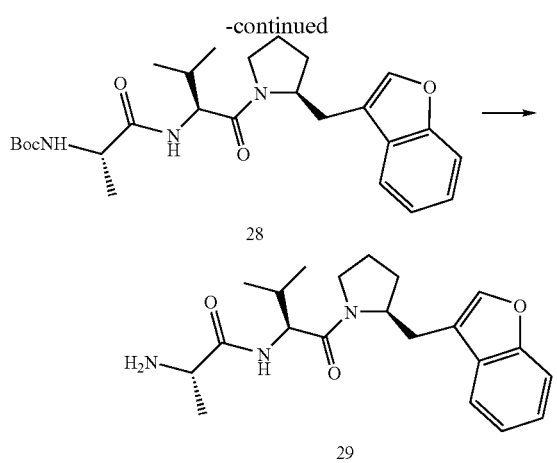

The Preparation of 2S-Amino-N-[1S-(2S-benzofuran-3-ylmethyl-pyrrolidine-1-carbonyl)-2-methyl-propyl]-propionamide (29)

A. trans-2S-[3-(2-Iodo-phenoxy)-propenyl]-pyrrolidine-1-carboxylic acid tert-butyl ester (23): To a solution of alcohol 22 (10.4 g, 0.04 mol) in DCM (300 mL) was added 2-iodophenol (12.1 g, 0.05 mol) and Ph₃P (14.4 g, 0.05 mol). At ambient temperature, ADDP (13.8 g, 0.05 mol) was added in one portion. After 16 h, the white precipitate was removed by filtration and washed with DCM. The clarified filtrate was washed successively with 1M NaOH, water, and brine. The organic phase was dried with anhydrous Na₂SO₄, and then filtered through a short column of silica gel. The product was eluted with DCM and then 1:1 hexane/EtOAc to afford 15.5 g (79%) of 23 as a colorless oil. ¹H NMR (CDCl₃, 300 MHz) δ 7.76 (dd, J=7.6, 1.1 Hz, 1H), 7.27 (app t, J=7.6, 1.1 Hz, 1H), 6.78 (dd, J=7.6, 1.1 Hz, 1H), 6.70 (app t, J=7.6, 1.1 Hz, 1H), 5.74 (m, 2H), 4.58 (app d, J=4.7 Hz, 2H), 4.33 (m, 1H), 3.40 (m, 2H), 2.02-1.75 (m, 4H), 1.43 (s, 9H) ppm.

B. 2S-Benzofuran-3-ylmethyl-pyrrolidine-1-carboxylic acid tert-butyl ester (24): To a solution of 23 (15.5 g, 36.1 mmol) in anhydrous DMF (250 mL) was added n-Bu₄NCl (10.0 g, 36.1 mmol), K₂CO₃ (5.0 g, 36.1 mmol), NaHCO₃ (2.45 g, 36.1 mmol), and Pd(OAc)₂ (0.16 g, 0.72 mmol). The orange-brown reaction mixture was immersed in a pre-heated (100° C.) oil bath. After 2 h, the reaction mixture was cooled to ambient temperature then diluted with diethyl ether and water. The layers were separated and the aqueous phase was extracted twice with diethyl ether. The combined organic extract was washed with water, brine, dried over anhydrous Na₂SO₄, filtered, and concentrated. The crude benzofuran was purified by flash silica gel chromatography (4:1 hexane/EtOAc) and then by normal-phase HPLC (30% EtOAc/hexane) to afford 4.6 g (42%) of 24 as a colorless oil. ¹H NMR (CDCl₃, 300 MHz) δ 7.62 (m, 1H), 7.46 (m, 1H), 7.26 (m, 3H), 4.13 (m, 1H), 3.40-3.21 (m, 2H), 3.15 (m, 1H), 2.68 (m, 1H), 1.80-1.61 (m, 4H), 1.51 (s, 9H) ppm.

C. 2S-Benzofuran-3-ylmethyl-pyrrolidine (25): Trifluoroacetic acid (2 mL) was added at 0° C. to a solution of 24 (0.5 g, 1.65 mmol) in DCM (40 mL). After 2 h, an additional portion of TFA (2 mL) was added. After 1 h, the reaction was quenched by the careful addition of aqueous NaHCO₃. The reaction mixture was diluted with water and the crude product was extracted with diethyl ether. The organic extract was washed with aqueous NaHCO₃, brine, dried over anhydrous Na₂SO₄, filtered, and concentrated. The crude amine was purified by reverse-phase HPLC (C18; 10-100% ACN/water, 0.1% TFA) which, following neutralization, afforded 0.24 g (72%) of 25 as a colorless oil. ¹H NMR (CDCl₃, 300 MHz) δ 7.53 (app d, J=8.7 Hz, 2H), 7.43 (d, J=8.2 Hz, 1H), 7.27 (dd, J=7.0, 8.2 Hz, 1H), 7.21 (dd, J=7.0, 8.7 Hz, 1H), 6.96 (br s, 1H), 3.59 (m, 1H), 3.16-2.86 (m, 4H), 1.96-1.75 (m, 3H), 1.60 (m, 1H) ppm.

D. [1S-(2S-Benzofuran-3-ylmethyl-pyrrolidine-1-carbonyl)-2-methyl-propyl]-carbamic acid tert-butyl ester (26): A solution of N-Boc L-valine (121 mg, 0.56 mmol) in NMP (3 mL) was treated with HATU (182 mg, 0.48 mmol) followed by N-methylmorpholine (0.1 mL, 0.9 mmol) at room temperature. After 10 min, amine 25 (80 mg, 0.4 mmol) in NMP (5 mL) was added dropwise. After 16 h, the reaction was diluted with EtOAc, washed with saturated NaHCO₃, 1M HCl, brine, dried over Na₂SO₄, filtered and concentrated. The residual oil was purified by HPLC (20% EtOAc/hexane) to afford 111 mg (69%) of 26 as a colorless oil. ¹H NMR (CDCl₃, 300 MHz) δ 7.87 (d, J=6.9 Hz, 1H), 7.48-7.32 (m, 2H), 7.30-7.24 (m, 4H), 5.35 (d, J=9.3 Hz, 1H), 4.53-4.47 (m, 1H), 4.31 (dd, J=6.6, 9.6 Hz, 1H), 3.72-3.56 (m, 2H), 3.31 (dd, J=3.0, 13.2 Hz, 1H), 2.49 (dd, J=10.5, 13.5 Hz, 1H), 2.05-1.74 (m, 6H), 1.44 (s, 9H), 1.03 (d, J=6.9 Hz, 3H), 097 (d, J=6.6 Hz, 3H) ppm.

E. 2S-Amino-1-(2S-benzofuran-3-ylmethyl-pyrrolidin-1-yl)-3-methyl-butan-1-one (27): A solution of carbamate 26 (111 mg, 0.28 mmol) in DCM (10 mL) was treated with TFA (1 mL) at room temperature. After 2 h, the reaction mixture was concentrated, diluted with EtOAc, washed with saturated aqueous NaHCO₃ and brine, dried over Na₂SO₄, filtered and concentrated to afford 67 mg (80%) of 27 as a light yellow oil. The product was used without further purification. ¹H NMR (CDCl₃, 300 MHz) δ 7.89 (d, J=8.1 Hz, 1H), 7.47-7.44 (m, 2H), 7.32-7.27 (m, 3H), 4.54-4.49 (m, 1H), 3.59-3.53 (m, 2H), 3.33 (d, J=13.5 Hz, 1H), 2.50 (dd, J=10.8, 13.5 Hz, 1H), 2.03-1.72 (m, 6H), 1.04 (d, J=7.2 Hz, 3H), 0.99 (d, J=7.0 Hz, 3H) ppm.

F. {1S-[1S-(2S-Benzofuran-3-ylmethyl-pyrrolidine-1-carbonyl)-2-methyl-propylcarbamoyl]-ethyl}-carbamic acid tert-butyl ester (28): A solution of N-Boc L-alanine (46 mg, 0.24 mmol) in NMP (3 mL) was treated with HATU (72 mg, 0.19 mmol) followed by N-methylmorpholine (0.1 mL, 0.9 mmol) at room temperature. After 10 min, amine 27 (41 mg, 0.14 mmol) in NMP (5 mL) was added dropwise. After 16 h, the reaction was diluted with EtOAc, washed with saturated NaHCO₃, 1M HCl, and brine, dried over Na₂SO₄, filtered and concentrated. The residual oil was purified by flash silica gel chromatography (1:1 hexane/EtOAc) to afford 62 mg (93%) of 28 as a colorless oil. ¹H NMR (CDCl₃, 300 MHz) δ 7.85 (d, J=6.6 Hz, 1H), 7.48-7.44 (m, 2H), 7.33-7.25 (m, 3H), 6.93 (d, J=8.7 Hz, 1H), 5.08 (d, J=7.8 Hz, 1H), 4.62 (dd, J=6.3, 8.7 Hz, 1H), 4.50-4.43 (m, 1H), 4.23-4.16 (m, 1H), 3.74-3.55 (m, 3H), 3.32 (dd, J=2.4, 14.1 Hz, 1H), 2.49 (dd, J=10.8, 13.5 Hz, 1H), 2.14-1.71 (m, 6H), 1.46 (s, 9H), 1.37 (d, J=6.9 Hz, 3H), 1.02 (d, J=6.9 Hz, 3H), 0.97 (d, J=7.2 Hz, 3H) ppm.

G. 2S-Amino-N-[1S-(2S-benzofuran-3-ylmethyl-pyrrolidine-1-carbonyl)-2-methyl-propyl]-propionamide (29): A solution of carbamate 28 (62 mg, 0.13 mmol) in DCM (10 mL) was treated with TFA (1 mL) at room temperature. After 1.5 h, the reaction was concentrated, diluted with EtOAc, washed with saturated NaHCO₃ and brine, dried over Na₂SO₄, filtered and concentrated. The residue was purified by flash silica gel chromatography (5% MeOH/DCM) to afford 38 mg (72%) of 29 as a colorless oil. ¹H NMR (CDCl₃, 300 MHz) δ 7.92 (d, J=9.3 Hz, 1H), 7.87-7.84 (m, 1H), 7.48-7.44 (m, 2H), 7.32-7.23 (m, 2H), 4.59 (dd, J=6.9, 9.3 Hz, 1H), 4.52-4.45 (m, 1H), 3.84-3.76 (m, 1H), 3.67-3.60 (m, 1H), 3.57-3.50 (m, 1H), 3.34 (dd, J=3.0, 13.0 Hz, 1H), 2.50 (dd, J=10.5, 13.8 Hz, 1H), 2.16-1.91 (m, 3H), 1.82-1.69 (m, 2H), 1.65 (bs, 2H), 1.38 (d, J=7.2 Hz, 3H), 1.03 (d, J=6.9 Hz, 3H), 0.99 (d, J=6.9 Hz, 3H) ppm. The free amine (29) was diluted with Et$_2$O and treated with HCl (g) to form a white solid. The solution was concentrated and the solid was triturated with Et$_2$O and hexanes to provide 29·HCl.

TABLE 5

(E6)

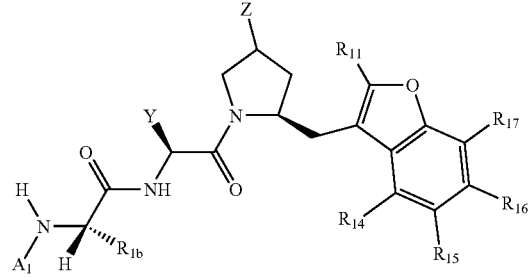

| Entry | $A_1$ | $R_{1b}$ | Y | Z | $R_{11}$ $R_{14-17}$ | MS $(M+H)^+$ | $K_D$ Range |
|---|---|---|---|---|---|---|---|
| 5-39 | H | Me | iPr | (S)-OPh | H | 464.2 | A |
| 5-40 | H | Me | tBu | (S)-OPh | H | 478.3 | A |
| 5-41 | H | Me | iPr | H | H | 372.2 | A |
| 5-42 | H | Me | cHex | (S)-OPh | H | 504.2 | A |
| 5-43 | Me | Me | cHex | (S)-OPh | H | 518.2 | A |
| 5-44 | H | Et | iPr | (S)-OPh | H | 478.2 | A |
| 5-45 | Me | Me | iPr | (S)-(S)-OPh | H | 478.2 | A |
| 5-46 | H | H | iPr | H | H | 358.3 | D |
| 5-47 | H | Me | cHex | H | H | 412.3 | A |
| 5-48 | Me | Me | cHex | H | H | 426.2 | A |
| 5-49 | H | Me | iPr | H | 5-Me ($R_{15}$) | 386.3 | A |
| 5-50 | Me | Me | iPr | H | 5-Me ($R_{15}$) | 400.3 | A |
| 5-51 | Me | Me | iPr | H | 5-F ($R_{15}$) | 404.2 | A |
| 5-52 | H | H | iPr | (S)-OPh | H | 450.2 | C |
| 5-53 | H | (R)-Me | iPr | (S)-OPh | H | 464.2 | C |
| 5-54 | H | Me | Et | (S)-OPh | H | 450.2 | A |
| 5-55 | H | Et | Et | (S)-OPh | H | 464.2 | B |
| 5-56 | H | Et | cHex | (S)-OPh | H | 518.2 | B |
| 5-57 | Me | Me | iPr | H | H | 386.3 | A |
| 5-58 | H | Et | iPr | H | H | 386.2 | B |
| 5-59 | H | Me | Et | H | H | 358.3 | B |
| 5-60 | H | Me | —CH(Me)OCH$_2$C≡CH | H | H | 412.2 | A |
| 5-61 | H | Me | iPr | H | 5-Cl ($R_{15}$) | 406.2 | A |
| 5-62 | Me | Me | iPr | H | 5-Cl ($R_{15}$) | 420.2 | A |
| 5-63 | H | Me | iPr | H | 5-BnO ($R_{15}$) | 478.2 | B |
| 5-64 | H | gem-di-Me | iPr | H | H | 386.3 | D |
| 5-65 | Ac | Me | iPr | H | H | 414.4 | D |
| 5-66 | H$_2$NCO | Me | iPr | H | H | 416.2 | D |
| 5-67 | HCO | Me | iPr | H | H | 400.3 | D |
| 5-68 | Et | Me | iPr | H | H | 400.3 | C |
| 5-69 | iPr | Me | iPr | H | H | 413.3 | C |
| 5-70 | cPrCH$_2$ | Me | iPr | H | H | 426.2 | C |
| 5-71 | HC≡CCH$_2$ | Me | iPr | H | H | 409.2 | D |
| 5-72 | (CH$_2$)$_2$ | | iPr | H | H | 384.3 | B |
| 5-73 | CH$_2$ | | iPr | H | H | 370.2 | D |
| 5-74 | (CH$_2$)$_3$ | | iPr | H | H | 398.4 | D |

EXAMPLE 7

This example illustrated pyrrolidine derivatives of Table 6.

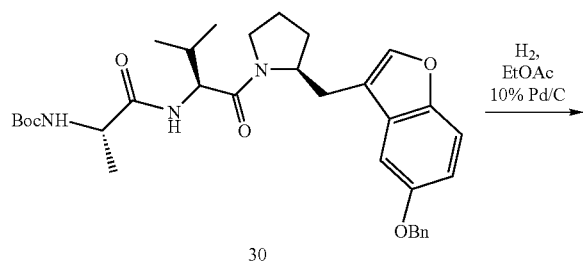

Scheme IV(b)

Preparation of 2-Amino-N-{1-[2-(5-hydroxy-benzofuran-3-ylmethyl)-pyrrolidine-1-carbonyl]-2-methyl-propyl}-propionamide (32)

A. (1-{1-[2-(5-Hydroxy-benzofuran-3-ylmethyl)-pyrrolidine-1-carbonyl]-2-methyl-propylcarbamoyl}-ethyl)-carbamic acid tert-butyl ester (31): A mixture of 30 (0.52 g, 0.90 mmol) and 10% Pd-on-carbon (0.05 g) in EtOAc (25 mL) was placed on a Parr apparatus and pressurized to 45 PSI H$_2$ atmosphere. The reaction mixture was shaken for 24 h. TLC analysis revealed only unconsumed starting material therefore the catalyst was removed by filtration and the clarified filtrate was concentrated to dryness. The residue was redissolved in EtOAc (25 mL) and 10% Pd-on-carbon (0.208 g) was added. The reaction mixture was shaken under a H$_2$ atmosphere (45 PSI) for 4 h at which time a second portion of palladium catalyst (0.05 g) was added. Hydrogenation was continued until all of the starting material was consumed (~2 h). The catalyst was removed by filtration and the filtrate was concentrated under reduced pressure. The crude product was purified by flash silica gel chromatography (EtOAc/hexane, 1:1) to afford 0.37 g (84%) of 31 as a white solid. $^1$H NMR (CDCl$_3$, 300 MHz) δ7.37 (s, 1H); 7.33-7.31 (m, 1H); 7.28-7.26 (m, 1H); 6.88-6.85 (m, 2H); 5.18 (br, 1H); 4.56 (t, 1H); 4.45-4.24 (m, 3H); 3.82-3.74 (m, 1H); 3.66-3.58 (m, 1H); 3.22 (d, 1H); 2.44-2.36 (m, 1H); 2.12-2.09 (m, 1H); 2.03-1.89 (m, 2H); 1.73-1.67 (m, 2H); 1.45 (s, 9H); 1.37 (d, 3H); 1.02-0.97 (m, 6H) ppm.

B. 2-Amino-N-{1-[2-(5-hydroxy-benzofuran-3-ylmethyl)-pyrrolidine-1-carbonyl]-2-methyl-propyl}-propionamide (32): To a solution of 31 (0.04 g, 0.082 mmol) in DCM (5 mL) was added TFA (1 mL) at ambient temperature. After 1 h, the solvent was removed under reduced pressure. The residue was dissolved in EtOAc and washed with aqueous NaHCO$_3$, brine, dried over anhydrous Na$_2$SO$_4$, filtered and concentrated. The crude product was purified by flash silica gel chromatography (10% MeOH/DCM) to afford 0.011 g (37%) of 32 as a white solid. $^1$H NMR (CDCl$_3$, 300 MHz) δ8.54 (d, 1H); 7.37 (s, 1H); 7.31 (d, 1H); 7.09 (d, 1H); 6.83 (dd, 1H); 4.64 (t, 1H); 4.56-4.51 (m, 1H); 4.09-3.93 (m, 2H); 3.73-3.65 (m, 1H); 3.36 (dd, 1H); 2.35 (t, 1H); 2.19-1.94 (m, 3H); 1.77-1.69 (m, 2H); 1.33 (d, 2H); 1.25-1.19 (m, 1H); 1.04-1.00 (m, 5H); 0.94 (t, 1H) ppm.

TABLE 6

(E7)

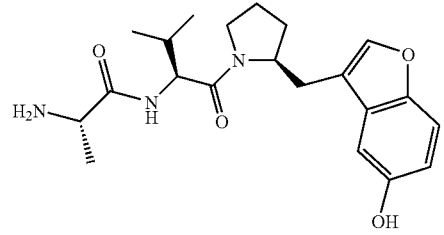

| Entry | $A_1$ | $R_{1b}$ | Y | Z | $R_{11,12}$, $R_{14-17}$ | MS $(M+H)^+$ | $K_D$ Range |
|---|---|---|---|---|---|---|---|
| 6-75 | H | Me | iPr | H | 5-OH ($R_{15}$) | 388.3 | C |

EXAMPLE 8

This example illustrated pyrrolidine derivatives of Table 7.

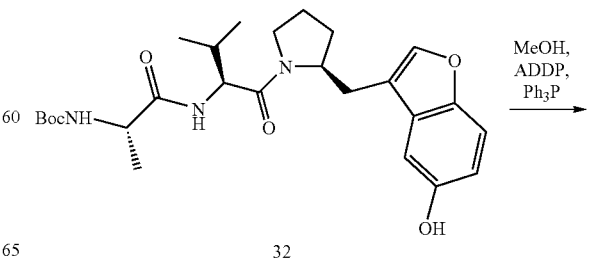

Scheme IV(c)

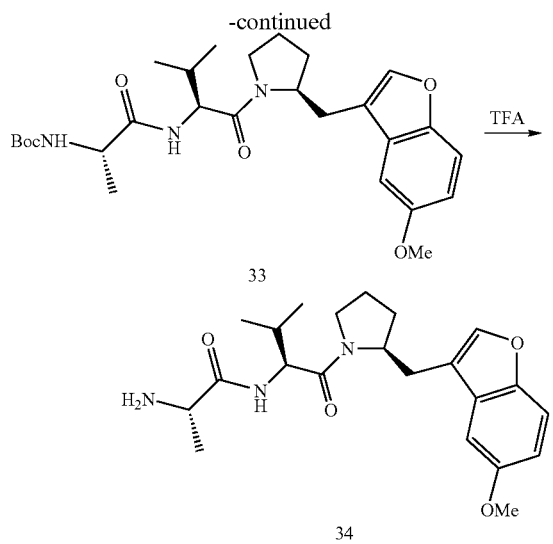

33

34

Preparation of 2-Amino-N-{1-[2-(5-methoxy-benzofuran-3-ylmethyl)-pyrrolidine-1-carbonyl]-2-methyl-propyl}-propionamide (34)

A. (1-{1-[2-(5-Methoxy-benzofuran-3-ylmethyl)-pyrrolidine-1-carbonyl]-2-methyl-propylcarbamoyl}-ethyl)-carbamic acid tert-butyl ester (33): To a solution of 32 (0.06 g, 0.12 mmol) in anhydrous DCM (3 mL) was added MeOH (10 µL), Ph$_3$P (0.036 g, 0.13 mmol), and ADDP (0.037 g, 0.14 mmol). The reaction mixture was maintained at ambient temperature for 16 h at which point TLC analysis revealed incomplete reaction. A second portion of MeOH (100 µL), Ph$_3$P (0.036 g, 0.13 mmol), and ADDP (0.037 g, 0.14 mmol) was added and the reaction mixture was maintained for an additional 5 h at ambient temperature. The reaction mixture was diluted with DCM and washed twice with 1 N NaOH, followed by brine, dried over anhydrous Na$_2$SO$_4$, filtered and concentrated. The crude product was purified by flash silica gel chromatography (EtOAc/hexane, 2:1) to afford 0.057 g (91%) of 33 as a white solid. $^1$H NMR (CDCl$_3$, 300 MHz) δ7.41 (s, 1H); 7.38-7.33 (m, 1H); 7.30-7.28 (m, 1H); 6.90 (dd, 1H); 6.77 (d, 1H); 4.98 (br, 1H); 4.64-4.59 (m, 1H); 4.48-4.43 (m, 1H); 4.21-4.14 (m, 1H); 3.88 (s, 3H); 3.72-3.53 (m, 2H); 3.30-3.25 (m, 1H); 2.51-2.43 (m, 1H); 2.13-1.72 (m, 5H); 1.45 (s, 9H); 1.37 (d, 3H); 1.03-0.95 (m, 6H) ppm.

B. 2-Amino-N-{1-[2-(5-methoxy-benzofuran-3-ylmethyl)-pyrrolidine-1-carbonyl]-2-methyl-propyl}-propionamide (34): To a solution of 33 (0.057 g, 0.11 mmol) in DCM (5 mL) was added TFA (1 mL) at ambient temperature. After 1 h, the solvent was removed under reduced pressure. The residue was dissolved in EtOAc and washed with aqueous NaHCO$_3$, brine, dried over anhydrous Na$_2$SO$_4$, filtered and concentrated. The crude product was purified by flash silica gel chromatography (10% MEOH/DCM) to afford 0.015 g (35%) of 34 as a white solid. $^1$H NMR (CDCl$_3$, 300 MHz) δ7.42 (m, 1H); 7.35 (d, 1H); 7.28 (m, 1H); 6.90 (dd, 1H); 4.60 (m, 1H); 4.48-4.45 (m, 1H); 3.89-3.76 (m, 4H); 3.65-3.56 (m, 2H); 3.31 (dd, 1H); 2.52-2.44 (m, 1H); 2.13-1.72 (m, 6H); 1.43-1.27 (m, 5H); 1.05-0.97 (m, 6H) ppm.

TABLE 7

(E8)

| Entry | A$_1$ | R$_{1b}$ | Y | Z | R$_{11, 12}$, R$_{14-17}$ | MS (M + H)$^+$ | K$_D$ Range |
|---|---|---|---|---|---|---|---|
| 7-76 | H | Me | iPr | H | 5-MeO (R$_{15}$) | 402.2 | C |
| 7-77 | H | Me | iPr | H | 5-cPrCH$_2$O (R$_{15}$) | 442.2 | D |

EXAMPLE 9

This example illustrated pyrrolidine derivatives of Table 8.

Scheme IV(d)

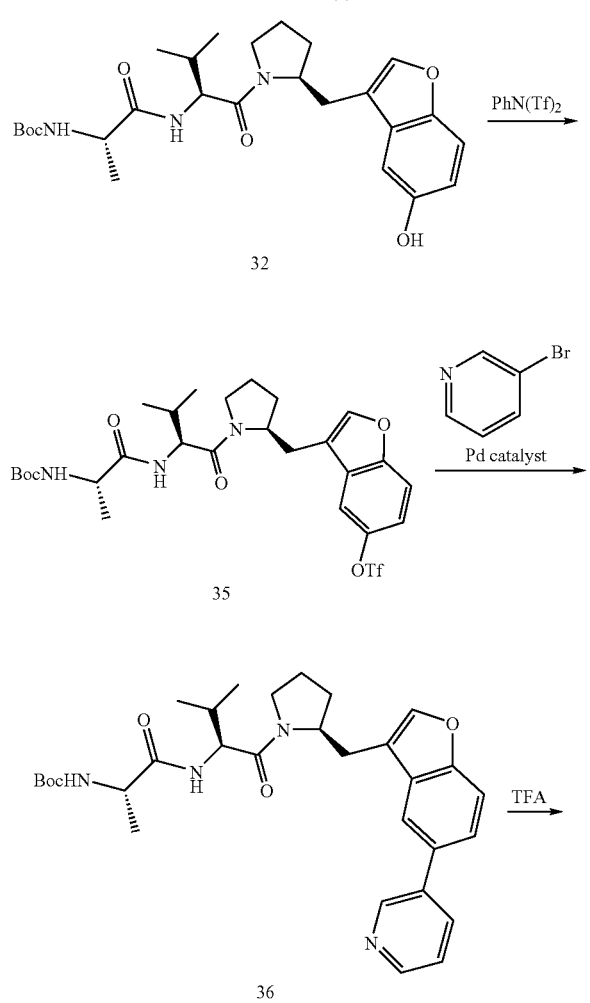

32

35

36

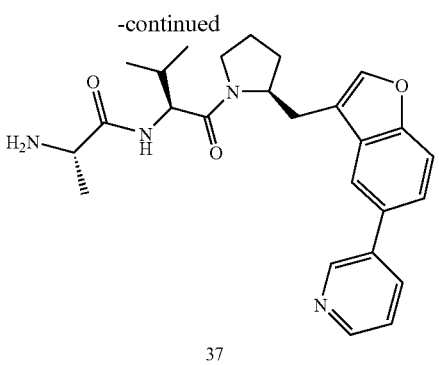

37

Preparation of 2-Amino-N-{2-methyl-1-[2-(5-pyridin-2-yl-benzofuran-3-ylmethyl)-pyrrolidine-1-carbonyl]-propyl}-propionamide (37)

A. Trifluoro-methanesulfonic acid 3-{1-[2-(2-tert-butoxycarbonylamino-propionylamino)-3-methyl-butyryl]-pyrrolidin-2-ylmethyl}-benzofuran-5-yl ester (35): To a solution of 32 (0.16 g, 0.32 mmol) and DIPEA (60 µL, 0.32 mmol) in anhydrous DCM (4 mL) was added N-phenyl-bis(trifluoromethanesulfonimide) (0.14 g, 0.38 mmol) at 0° C. After ~10 min, the reaction mixture was allowed to warm to ambient temperature and then maintained for 16 h. The reaction mixture was concentrated and the residue was dissolved in EtOAc, washed with water, brine, dried over anhydrous $Na_2SO_4$, filtered and concentrated. The crude product was purified by flash silica gel chromatography (EtOAc/hexane, 1:1) to afford 126 mg (63%) of 35 as a white solid. $^1$H NMR (CDCl$_3$, 300 MHz) δ7.73 (d, 1H); 7.55-7.48 (m, 2H); 7.20 (dd, 1H); 6.78-6.75 (m, 1H); 4.99 (br, 1H); 4.63-4.58 (m, 1H); 4.41-4.35 (m, 1H); 4.19 (m, 1H); 3.75-3.68 (m, 1H); 3.64-3.57 (m, 1H); 3.29 (dd, 1H); 2.54-2.46 (m, 1H); 1.99-1.84 (m, 3H); 1.71-1.66 (m, 2H); 1.45 (s, 9H); 1.37 (d, 3H); 1.02-0.94 (m, 6H) ppm.

B. (1-{2-Methyl-1-[2-(5-pyridin-3-yl-benzofuran-3-ylmethyl)-pyrrolidine-1-carbonyl]-propylcarbamoyl}-ethyl)-carbamic acid tert-butyl ester (36): A mixture of 35 (0.063 g, 0.10 mmol), $K_2CO_3$ (70 mg, 0.50 mmol), 3-pyridineboronic acid (0.015 g, 0.12 mmol), and (Ph$_3$P)$_4$Pd (5 mg, 3 mol %) in anhydrous toluene (5 mL) was heated at 100° C. in a sealed tube for 1 h. The reaction mixture was cooled to room temperature, diluted with EtOAc, washed with saturated aqueous NaHCO$_3$, brine, dried over anhydrous $Na_2SO_4$, filtered and concentrated. The crude product was purified by flash silica gel chromatography (EtOAc) to afford 40 mg (72%) of 36 as an oil. $^1$H NMR (CDCl$_3$, 300 MHz) δ8.94 (d, 1H); 8.59 (d, 1H); 8.01-7.95 (m, 1H); 7.74-7.64 (m, 1H); 7.58-7.37 (m, 4H); 6.94 (d, 1H); 4.61 (t, 1H); 4.50-4.47 (m, 1H); 4.30 (t, 1H0; 4.21 (br, 1H); 3.79-3.71 (m, 1H); 3.66-3.59 (m, 1H); 2.42-3.36 (m, 1H); 2.58-2.50 (m, 1H); 2.13-2.09 (m, 1H); 2.01-1.71 (m, 4H); 1.45 (m, 9H); 1.37 (d, 3H); 1.03-0.94 (m, 6H) ppm.

C. 2-Amino-N-{2-methyl-1-[2-(5-pyridin-2-yl-benzofuran-3-ylmethyl)-pyrrolidine-1-carbonyl]-propyl}-propionamide (37): To a solution of 36 (0.04 g, 0.07 mmol) in DCM (5 mL) was added TFA (1 mL) at ambient temperature. After 1 h, the solvent was removed under reduced pressure. The residue was dissolved in EtOAc and washed with aqueous NaHCO$_3$, brine, dried over anhydrous $Na_2SO_4$, filtered and concentrated. The crude product was purified by flash silica gel chromatography (10% MeOH/DCM) to afford 0.024 g (76%) of 37 as a white solid. $^1$H NMR (CDCl$_3$, 300 MHz) δ8.0 (s, 1H); 7.95 (d, 1H); 7.71-7.64 (m, 2H); 7.56-7.46 (m, 4H); 4.61-4.48 (m, 2H); 4.29 (t, 1H); 3.83-3.77 (m, 1H); 3.67-3.54 (m, 2H); 3.41 (dd, 1H); 2.58-2.49 (m, 1H); 2.13-1.70 (m, 5H); 1.40-1.25 (m, 5H); 1.04-0.84 (m 6H) ppm.

TABLE 8

(E9)

| Entry | $A_1$ | $R_{1b}$ | Y | Z | $R_{11, 12, 14-17}$ | MS $(M + H)^+$ | $K_D$ Range |
|---|---|---|---|---|---|---|---|
| 8-78 | H | Me | iPr | H | 5-(4-Pyr) ($R_{15}$) | 449.2 | B |
| 8-79 | H | Me | iPr | H | 5-(3-Pyr) ($R_{15}$) | 449.2 | C |

EXAMPLE 10

This example illustrated pyrrolidine derivatives of Table 9.

Scheme V

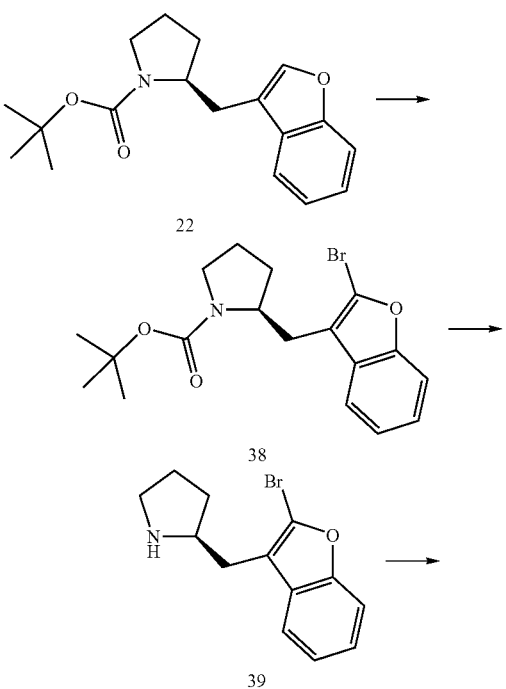

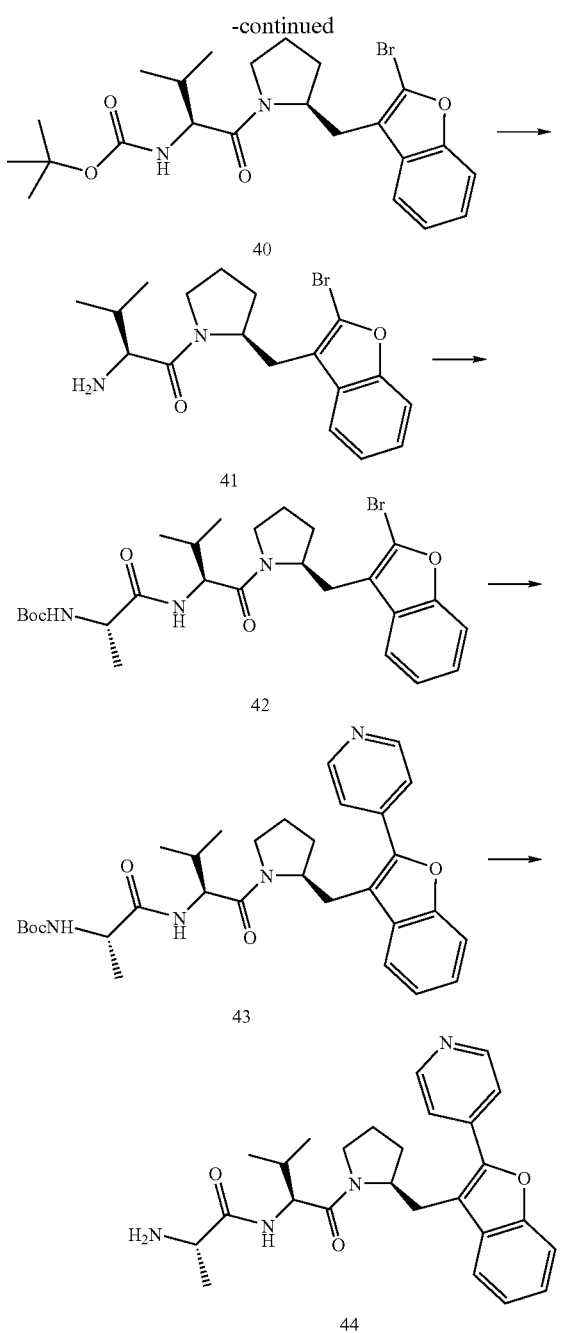

The Preparation of 2S-Amino-N-{2-methyl-1S-[2S-(2-pyridin-4-yl-benzofuran-3-ylmethyl)-pyrrolidine-1-carbonyl]-propyl}-propionamide (44)

A. 2S-(2-Bromo-benzofuran-3-ylmethyl)-pyrrolidine-1-carboxylic acid tert-butyl ester (38): A solution of 22 (1.4 g, 4.7 mmol) in CHCl$_3$ (20 mL) was cooled to 0° C. and treated with KOAc (2.5 g, 26 mmol). A solution of bromine (0.3 mL, 5.8 mmol) in CHCl$_3$ (10 mL) was added dropwise over 30 min. Following addition, the solution maintained a yellow orange color. After TLC indicated consumption of starting material, the reaction mixture was diluted with H$_2$O, washed with saturated Na$_2$S$_2$O$_8$, dried over Na$_2$SO$_4$, filtered, and concentrated. Purification of the residue by flash silica gel chromatography (3:1 hexane/EtOAc) afforded 1.1 g (61%) of 38 as a yellow oil. $^1$H NMR (CDCl$_3$, 300 MHz) δ 7.57-7.52 (m, 1H), 7.43-7.41 (m, 1H), 7.26-7.20 (m, 2H), 4.20 (m, 1H), 3.43-3.30 (m, 2H), 3.17-3.01 (m, 1H), 2.73-2.58 (m, 1H), 1.89-1.69 (m, 4H), 1.48 (s, 9H) ppm.

B. 2S-(2-Bromo-benzofuran-3-ylmethyl)-pyrrolidine (39): A solution of 38 (1.1 g, 2.9 mmol) in DCM (20 mL) was treated with TFA (2 mL) at room temperature. After 1.5 h, the reaction mixture was concentrated, diluted with EtOAc, washed with saturated NaHCO$_3$, brine, dried over Na$_2$SO$_4$, filtered and concentrated to afford 0.8 g of 39 as an orange oil which was used without further purification. $^1$H NMR (CDCl$_3$, 300 MHz) δ 8.84 (br s, 1H), 7.42-7.39 (m, 2H), 7.28-7.21 (m, 2H), 3.70-3.66 (m, 1H), 3.48-3.39 (m, 1H), 3.31-3.21 (m, 2H) 2.95 (dd, J=9.9 Hz, 13.5 Hz, 1H), 2.06-1.99 (m, 1H), 1.91-1.79 (m, 2H), 1.74-1.66 (m, 1H) ppm.

C. {1S-[2S-(2-Bromo-benzofuran-3-ylmethyl)-pyrrolidine-1-carbonyl]-2-methyl-propyl}-carbamic acid tert-butyl ester (40): A solution of N-Boc L-valine (656 mg, 3.0 mmol) in NMP (6 mL) was treated with HATU (1.2 g, 3.1 mmol) followed by N-methylmorpholine (0.4 mL, 3.6 mmol) at room temperature. After 10 min, crude 39 (0.8 g, 2.9 mmol) in NMP (6 mL) was added dropwise. After 16 h, the reaction mixture was diluted with EtOAc, washed with saturated NaHCO$_3$, brine, dried over Na$_2$SO$_4$, filtered and concentrated. The residue was purified by flash silica gel chromatography (3:1 hexane/EtOAc) to afford 853 mg (61%) of 40 as a yellow foam. $^1$H NMR (CDCl$_3$, 300 MHz) δ 7.89-7.86 (m, 1H), 7.42-7.38 (m, 1H), 7.29-7.25 (m, 3H), 5.35 (d, J=9.3 Hz, 1H), 4.55-4.51 (m, 1H), 4.29 (dd, J=6.0, 9.6 Hz, 1H), 3.71-3.66 (m, 1H), 3.27 (dd, J=3.3, 13.5 Hz, 1H), 2.45 (dd, J=10.8, 13.5 Hz, 1H), 2.15-1.92 (m, 3H), 1.79-1.74 (m, 2H), 1.42 (s, 9H), 1.03 (d, J=6.9 Hz, 3H), 0.96 (d, J=7.2 Hz, 3H) ppm.

D. 2S-Amino-1-[2S-(2-bromo-benzofuran-3-ylmethyl)-pyrrolidin-1-yl]-3-methyl-butan-1-one (41): A solution of carbamate 40 (853 mg, 1.8 mmol) in DCM (20 mL) was treated with TFA (2 mL) at room temperature. After 1.5 h, the reaction mixture was concentrated, diluted with EtOAc, washed with saturated NaHCO$_3$, brine, dried over Na$_2$SO$_4$, filtered and concentrated to afford 0.66 g of 41 as a yellow foam which was used without further purification. $^1$H NMR (CDCl$_3$, 300 MHz) δ 7.92-7.89 (m, 1H), 7.44-7.39 (m, 1H), 7.30-7.25 (m, 3H), 4.55 (m, 1H), 3.66-3.51 (m, 2H), 3.29 (dd, J=2.4, 13.5 Hz, 1H), 2.45 (dd, J=11.1, 12.9 Hz, 1H), 2.15-1.97 (m, 2H), 1.78-1.71 (m, 2H), 1.06 (d, J=6.3 Hz, 3H), 1.01 (d, J=6.6 Hz, 3H) ppm.

E. (1S-{1S-[2S-(2-Bromo-benzofuran-3-ylmethyl)-pyrrolidine-1-carbonyl]-2-methyl-propylcarbamoyl}-ethyl)-carbamic acid tert-butyl ester (42): A solution of N-BOC-L-alanine (394 mg, 2.1 mmol) in NMP (6 mL) was treated with HATU (763 mg, 2.0 mmol) followed by N-methylmorpholine (0.3 mL, 2.7 mmol) at room temperature. After 10 min, crude 41 (0.66 mg, 1.7 mmol) in NMP (6 mL) was added dropwise. After 16 h, the reaction mixture was diluted with EtOAc, washed with saturated NaHCO$_3$, 1M HCl, brine, dried over Na$_2$SO$_4$, filtered and concentrated. The residual oil was purified by flash silica gel chromatography (2:1 hexane/EtOAc-to-1:1 hexane/EtOAc) to afford 0.9 g (96%) of 42 as an off-white foam. $^1$H NMR (CDCl$_3$, 300 MHz) δ 7.86-7.84 (m, 1H), 7.43-7.40 (m, 1H), 7.29-7.25 (m, 2H), 7.01 (d, J=8.7 Hz, 1H), 5.10 (d, J=6.6 Hz, 1H), 4.62 (dd, J=6.3, 8.7 Hz, 1H), 4.53-4.48 (m, 1H), 4.23-4.19 (m, 1H), 3.75-3.66 (m, 2H), 3.27 (dd, J=3.3, 13.5 Hz, 1H), 2.45 (dd, J=10.5, 13.5 Hz, 1H), 2.16-2.08 (m, 2H), 2.02-1.97 (m, 2H), 1.79-1.73 (m, 2H), 1.45 (s, 9H), 1.36 (d, J=6.9 Hz, 3H), 1.02 (d, J=6.3 Hz, 3H), 0.97 (d, J=7.2 Hz, 3H) ppm.

F. (1S-{2-Methyl-1S-[2S-(2-pyridin-4-yl-benzofuran-3-ylmethyl)-pyrrolidine-1-carbonyl]-propylcarbamoyl}-ethyl)-carbamic acid tert-butyl ester (43): A solution of 42 (36 mg, 0.07 mmol) in toluene (4 mL) was treated with $K_2CO_3$ (38 mg, 0.28 mmol) and $Pd(PPh_3)_4$ (2 mg) followed by 4-pyridine boronic acid (12 mg, 0.1 mmol) in EtOH (2 mL). The reaction was heated to reflux overnight. The solution was cooled to room temperature, diluted with $H_2O$, extracted with EtOAc, brine, dried over $Na_2SO_4$, filtered and concentrated to afford 44 mg of 43 as a light yellow oil which was used without further purification. $^1H$ NMR ($CDCl_3$, 300 MHz) δ 8.74 (d, J=5.1 Hz, 1H), 7.99 (d, J=5.7 Hz, 1H), 7.86-7.81 (m, 1H), 7.71-7.64 (m, 1H), 7.56-7.46 (m, 3H), 7.41-7.27 (m, 2H), 6.87 (d, J=8.7 Hz, 1H), 5.01 (m, 1H), 4.62 (app t, J=8.7 Hz, 1H), 4.56-4.46 (m, 1H), 4.20 (m, 1H), 3.72-3.67 (m, 2H), 2.84 (dd, J=11.7, 13.5 Hz, 1H), 2.16-1.93 (m, 2H), 1.78-1.62 (m, 2H), 1.46 (s, 9H), 1.37 (d, J=7.2 Hz, 3H), 1.04 (d, J=6.6 Hz, 3H), 0.98 (d, J=6.3 Hz, 3H) ppm.

G. 2S-Amino-N-{2-methyl-1S-[2-(2S-pyridin-4-yl-benzofuran-3-ylmethyl)-pyrrolidine-1-carbonyl]-propyl}-propionamide (44): A solution of 43 (44 mg, 0.08 mmol) in DCM (10 mL) was treated with TFA (1 mL) at room temperature. After 1.5 h, the reaction mixture was concentrated, diluted with EtOAc, washed with saturated $NaHCO_3$, brine, dried over $Na_2SO_4$, filtered and concentrated. The residue was purified by reverse-phase HPLC (C18; 10-100% $ACN/H_2O$ with 0.1% AcOH buffer). The fractions containing pure product were lyophilized to afford 21 mg of 44 as a white solid. $^1H$ NMR ($CDCl_3$, 300 MHz) δ 8.75 (bs, 1H), 8.00 (m, 1H), 7.90-7.82 (m, 1H), 7.71-7.64 (m, 1H), 7.55-7.47 (m, 3H), 7.38-7.27 (m, 2H), 4.61-4.52 (m, 1H), 3.83-3.62 (m, 2H), 3.07-3.00 (m, 1H), 2.84 (dd, J=11.1, 13.5 Hz, 1H), 2.16-1.94 (m, 2H), 1.74-1.61 (m, 2H), 1.41 (d, J=6.9 Hz, 3H), 1.05 (d, J=6.6 Hz, 3H), 0.99 (d, J=6.9 Hz, 3H) ppm.

TABLE 9

(E10)

| Entry | $A_1$ | $R_{1b}$ | Y | Z | $X_2$ | $R_{11}$ | MS $(M+H)^+$ | $K_D$ Range |
|---|---|---|---|---|---|---|---|---|
| 9-80 | H | Me | iPr | H | O | Br | 450.4 | B |
| 9-81 | H | Me | iPr | H | O | 4-Pyr | 449.2 | A |
| 9-82 | H | Me | iPr | H | O | 3-Pyr | 449.2 | B |
| 9-83 | H | Me | iPr | H | O | 5-[(2-MeO)Pyr] | 479.2 | B |
| 9-84 | H | Me | iPr | H | O | 2-Pyr | 449.3 | A |
| 9-85 | H | Me | iPr | H | O | 2-thiazoyl | 455.2 | B |
| 9-86 | H | Me | iPr | H | O | 2-pyrazine | 450.1 | A |
| 9-87 | H | Me | iPr | H | O | Ph | 448.3 | B |
| 9-88 | H | Me | iPr | H | N | Ph, ($R_{12}$ is H) | 447.2 | C |

EXAMPLE 11

This example illustrated pyrrolidine derivatives of Table 10.

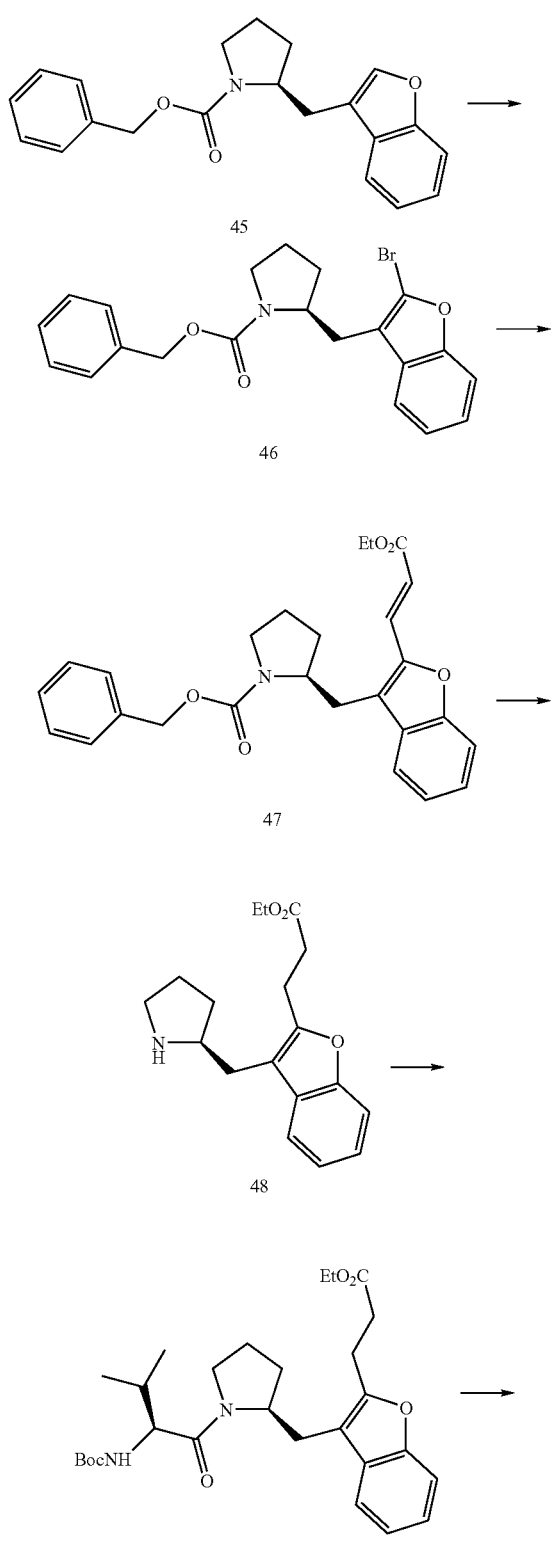

Scheme V(a)

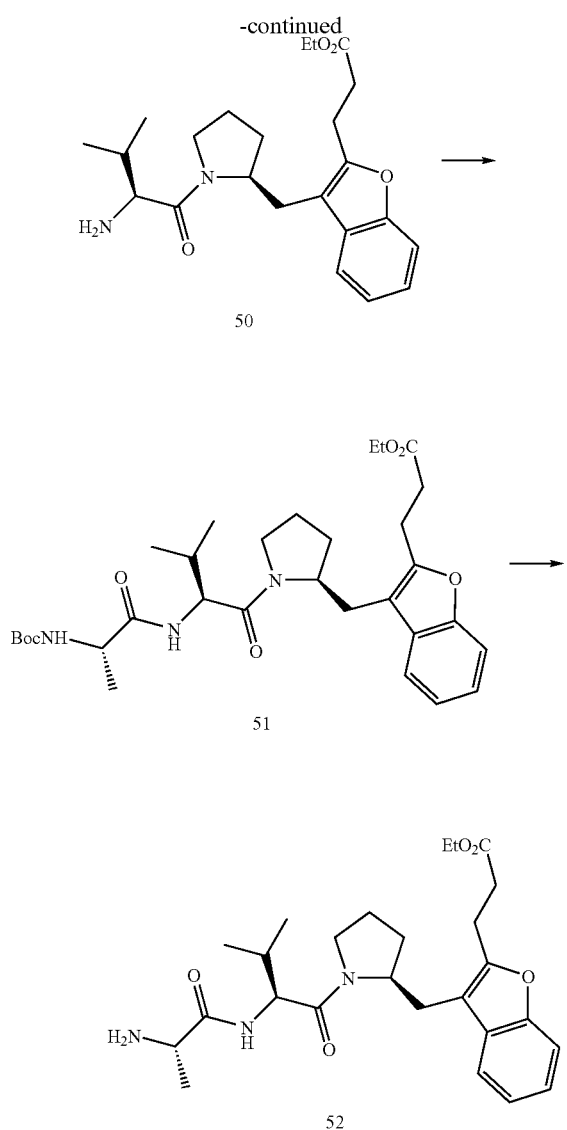

The Preparation of 3-(3-{1-[2-(2-Amino-propionylamino)-3-methyl-butyryl]-pyrrolidin-2-ylmethyl}-benzofuran-2-yl)-propionic acid ethyl ester (52)

A. 2-(2-Bromo-benzofuran-3-ylmethyl)-pyrrolidine-1-carboxylic acid benzyl ester (46): To a cooled (0° C.) solution of 45 (4.1 g, 12.2 mmol) in CHCl$_3$ (70 mL) was added KOAc (3.6 g, 36.7 mmol) followed by the dropwise addition of Br$_2$ (2.3 g, 14.6 mmol) in CHCl$_3$ (30 mL) over ~20 min. After 30 min, the reaction mixture was diluted with brine and saturated with Na$_2$S$_2$O$_8$. The product was extracted with DCM and the combined DCM extracts were washed with brine, dried over anhydrous Na$_2$SO$_4$, filtered and concentrated to afford 5 g (quant.) of 46 as an orange oil which was used without further purification. $^1$H NMR (CDCl$_3$, 300 MHz) δ 7.75-7.72 & 6.98 (rotamers, m and app t, J=7.5 Hz, 1H), 7.44-7.10 (m, 8H), 5.24-5.17 (m, 2H), 4.28 & 4.17 (rotamer, 2 m, 1H), 3.54-3.38 (m, 2H), 3.21 & 3.00 (rotamer, 2 dd, J=2.4, 13.5 Hz, 1H), 2.72-2.55 (m, 1H), 1.97-1.75 (m, 4H) ppm.

B. 2-[2-(2-Ethoxycarbonyl-vinyl)-benzofuran-3-ylmethyl]-pyrrolidine-1-carboxylic acid benzyl ester (47): A solution containing crude 46 (5.0 g, 12.1 mmol), ethyl acrylate (2.7 g, 27.7 mmol), tetrabutylammonium chloride (3.5 g, 12.6 mmol), NaHCO$_3$ (2.0 g, 23.8 mmol), and Pd(OAc)$_2$ (0.107 g, 0.46 mmol) in DMF (40 mL) was heated at 100° C. for 16 h. After cooling to ambient temperature, the reaction mixture was diluted with diethyl ether and washed with water, brine, dried over anhydrous Na$_2$SO$_4$, filtered and concentrated. The crude product was purified by flash silica gel chromatography (EtOAc/hexane, 1:3) to afford 3.7 g (70%) of 47 as an orange-colored oil. $^1$H NMR (CDCl$_3$, 300 MHz) δ 7.81 & 6.99 (rotamer, app d, J=7.5 Hz, app t, J=7.5 Hz, 1H), 7.61 (dd, J=15.9, 18.3 Hz, 1H), 7.47-7.20 (m, 8H), 6.58 (dd, J=5.7, 15.6 Hz, 1H), 5.27-5.16 (m, 2H), 4.24 (q, J=7.2 Hz, 2H), 4.17-4.08 (m, 1H), 3.51-3.35 (m, 2H), 3.38 & 3.17 (rotamer, 2 dd, J=3.6, 14.1 Hz, 1H), 2.89-2.69 (m, 1H), 1.94-1.64 (m, 4H), 1.36 (t, J=7.2 Hz, 2H) ppm.

C. 3-(3-Pyrrolidin-2-ylmethyl-benzofuran-2-yl)-propionic acid ethyl ester (48): A mixture containing 47 (1.0 g, 2.3 mmol) and 10% Pd-on-carbon (~1 g) in anhydrous MeOH (20 mL) was placed under a hydrogen atmosphere (45 PSI) and shaken using a Parr apparatus for 1 h. The catalyst was removed by filtration and the solids were washed with EtOAc and MeOH. The clarified filtrate was concentrated to afford 634 mg (91%) of 48 as an orange oil which was used without further purification. $^1$H NMR (CDCl$_3$, 300 MHz) δ 7.51-7.49 (m, 1H), 7.38-7.35 (m, 1H), 7.21-7.17 (m, 2H), 4.16-4.09 (m, 2H), 3.68-3.59 (m, 2H), 3.12-3.07 (m, 2H), 2.88-2.73 (m, 4H), 1.84-1.69 (m, 4H), 1.43-1.39 (m, 1H), 1.26-1.20 (m, 3H) ppm.

D. 3-{3-[1-(2-tert-Butoxycarbonylamino-3-methyl-butyryl)-pyrrolidin-2-ylmethyl]-benzofuran-2-yl}-propionic acid ethyl ester (49): A solution containing Boc-L-valine (352 mg, 1.6 mmol) in NMP (3 mL) was treated with HATU (543 mg, 1.4 mmol) followed by NMM (0.2 mL, 1.8 mmol) at ambient temperature. After 10 min, amine 48 (0.4 g, 1.3 mmol) in NMP (5 mL) was added in a dropwise fashion. After 16 h, the reaction mixture was diluted with diethyl ether and washed successively with NaHCO$_3$, 1 M HCl, water, and brine. The organic extract was dried over anhydrous Na$_2$SO$_4$, filtered and concentrated to afford 630 mg (96%) of 49 which was used without further purification. $^1$H NMR (CDCl$_3$, 300 MHz) δ 7.82-7.79 (m, 1H), 7.38-7.35 (m, 1H), 7.28-7.21 (m, 2H), 5.37 (d, J=9.3 Hz, 1H), 4.50-4.44 (m, 1H), 4.31 (dd, J=6.0, 9.0 Hz, 1H), 4.14 (q, J=6.9 Hz, 2H), 3.72-3.60 (m, 3H), 3.38 (t, J=7.2 Hz, 1H), 3.29 (dd, J=3.0, 13.5 Hz, 1H), 3.12 (app t, J=7.5 Hz, 2H), 2.80-2.74 (m, 4H), 2.46-2.35 (m, 2H), 2.11-1.92 (m, 2H), 1.81-1.73 (m, 1H), 1.69-1.65 (m, 1H), 1.44 (s, 9H), 1.25 (t, J=6.0 Hz, 3H), 1.03 (d, J=6.3 Hz, 3H), 0.96 (d, J=6.6 Hz, 3H) ppm. Mass spectrum: m/z 501 [M+H]$^+$; and, 523 [M+Na]$^+$.

E. 3-{3-[1-(2-Amino-3-methyl-butyryl)-pyrrolidin-2-ylmethyl]-benzofuran-2-yl}-propionic acid ethyl ester (50): To a solution of 49 (302 mg, 0.6 mmol) in DCM (10 mL) was added TFA (2 mL) at ambient temperature. After 2 h, the solvent was removed under reduced pressure. The residue was dissolved in EtOAc and washed with aqueous NaHCO$_3$, brine, dried over anhydrous Na$_2$SO$_4$, filtered and concentrated to afford 235 mg (97%) of 50 as an orange oil which was used without further purification. $^1$H NMR (CDCl$_3$, 300 MHz) δ 7.86-7.83 (m, 1H), 7.43-7.34 (m, 1H), 7.27-7.19 (m, 3H), 4.49 (m, 1H), 4.14 (q, J=6.9 Hz, 2H), 3.60-3.53 (m, 2H), 3.32 (d, J=12.9 Hz, 1H), 3.12 (app t, J=7.2 Hz, 2H), 2.81-2.74 (m, 2H), 2.42 (app t, J=12.3 Hz, 1H), 2.10-1.91 (m, 2H), 1.74-1.66 (m, 2H), 1.24 (t, J=7.2 Hz, 3H), 1.06-0.99 (m, 6H) ppm. Mass spectrum: m/z 401 [M+H]$^+$.

F. 3-(3-{1-[2-(2-tert-Butoxycarbonylamino-propionylamino)-3-methyl-butyryl]-pyrrolidin-2-ylmethyl}-benzofuran-2-yl)-propionic acid ethyl ester (51): A solution containing Boc-L-alanine (69 mg, 0.37 mmol) in NMP (3 mL) was treated with HATU (131 mg, 0.34 mmol) followed by NMM (0.1 mL, 0.9 mmol) at ambient temperature. After 10 min, amine 50 (111 mg, 0.28 mmol) in NMP (5 mL) was added in a dropwise fashion. After 5 h, the reaction mixture was diluted with diethyl ether and washed successively with $NaHCO_3$, 1 M HCl, water, and brine. The organic extract was dried over anhydrous $Na_2SO_4$, filtered and concentrated to afford 160 mg (quant.) of 51 which was used without further purification. $^1$H NMR ($CDCl_3$, 300 MHz) δ7.81-7.78 (m, 1H), 7.38-7.36 (m, 1H), 7.28-7.21 (m, 3H), 6.86 (d, J=8.7 Hz, 1H), 5.04 (d, J=6.9 Hz, 1H), 4.61 (dd, J=6.3, 8.7 Hz, 1H), 4.48-4.42 (m, 1H), 4.22 (m, 1H), 4.13 (q, J=6.9 Hz, 2H), 3.73-3.62 (m, 2H), 3.41-3.36 (m, 2H), 3.28 (dd, J=3.0, 13.5 Hz, 1H), 3.11 (app t, J=6.9 Hz, 2H), 2.85-2.73 (m, 4H), 2.38 (app t, J=8.1 Hz, 2H), 2.13-1.98 (m, 2H), 1.80-1.64 (m, 1H), 1.45 (s, 9H), 1.37 (d, J=6.9 Hz, 3H), 1.26 (t, J=7.5 Hz, 3H), 1.03-0.95 (m, 6H) ppm. Mass spectrum: m/z 572 $[M+H]^+$; and, 594 $[M+Na]^+$.

G. 3-(3-{1-[2-(2-Amino-propionylamino)-3-methyl-butyryl]-pyrrolidin-2-ylmethyl}-benzofuran-2-yl)-propionic acid ethyl ester (52): To a solution of 51 (160 mg, 0.28 mmol) in DCM (10 mL) was added TFA (2 mL) at ambient temperature. After 2.5 h, the solvent was removed under reduced pressure. The residue was dissolved in EtOAc and washed with aqueous $NaHCO_3$, brine, dried over anhydrous $Na_2SO_4$, filtered and concentrated. A portion (~50%) of the crude material was purified by reverse-phase HPLC (C18, 10-100% ACN/water containing 0.1% HOAc) to afford 56 mg of 52 as a white solid. $^1$H NMR (DMSO, 300 MHz) δ8.03 (d, J=8.7 Hz, 1H), 7.77 (m, 1H), 7.43-7.41 (m, 1H), 7.21 (m, 2H), 4.37 (app t, J=8.1 Hz, 1H), 4.19 (m, 1H), 4.01 (q, J=7.2 Hz, 2H), 3.65 (m, 1H), 3.56 (app d, J=6.6 Hz, 1H), 3.28 (m, 1H), 3.06-3.01 (m, 3H), 2.68 (app t, J=7.2 Hz, 2H), 2.07-1.96 (m, 1H), 1.63 (m, 1H), 1.54 (m, 1H), 1.13-1.09 (m, 6H), 0.90 (d, J=6.3 Hz, 3H), 0.85 (d, J=6.3 Hz, 3H) ppm. Mass spectrum: m/z 472 $[M+H]^+$; and, 494 $[M+Na]^+$.

TABLE 10

(E11)

| Entry | $A_1$ | $R_{1b}$ | Y | Z | $X_2$ | $R_{11}$ | MS $(M+H)^+$ | $K_D$ Range |
|---|---|---|---|---|---|---|---|---|
| 10-89 | H | Me | iPr | H | O | $-CH_2CH_2CO_2Et$ | 472.3 | C |
| 10-90 | H | Me | iPr | H | O | $-CH_2CH_2CO_2H$ | 444.2 | B |

EXAMPLE 12

This example illustrated pyrrolidine derivatives of Table 11 and Table 12.

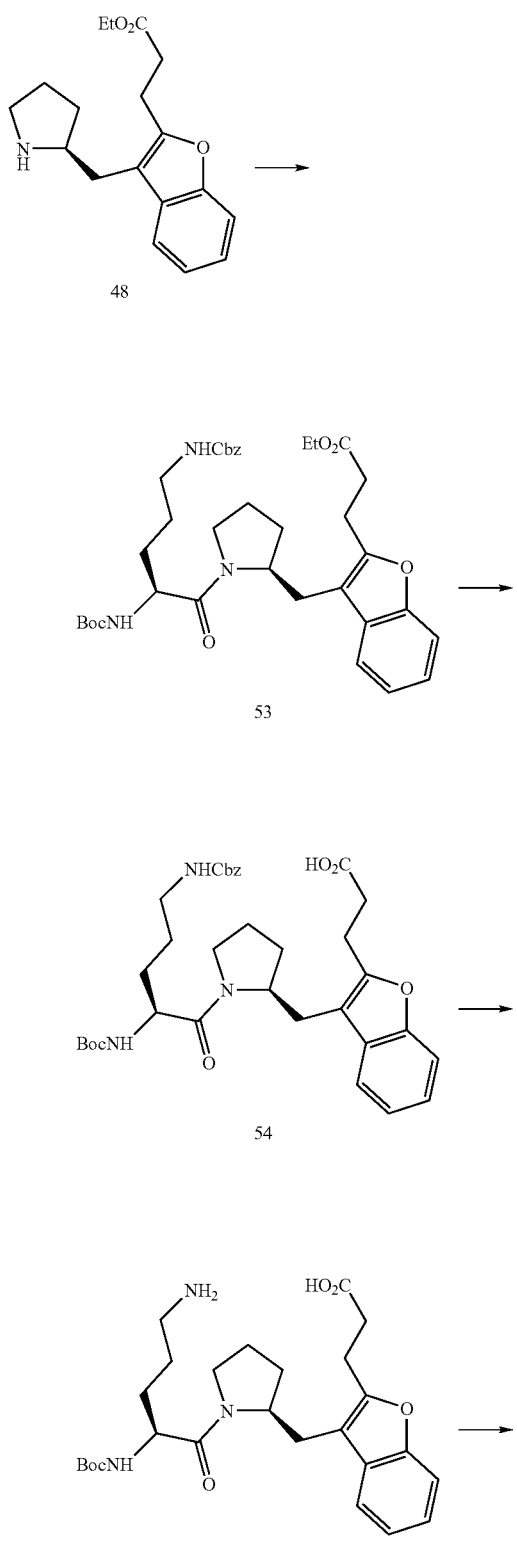

Scheme V(a)

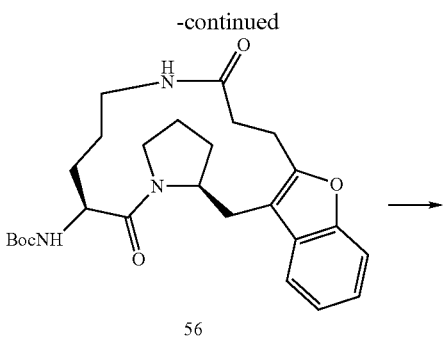

56

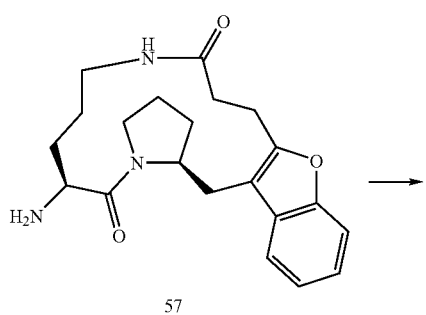

57

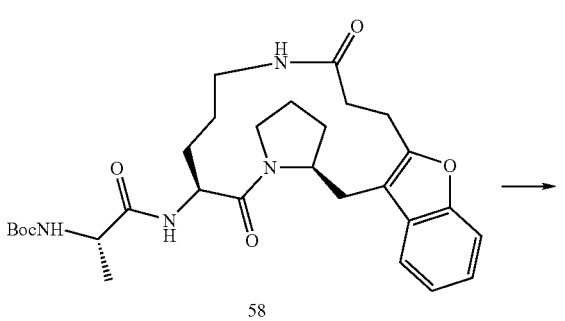

58

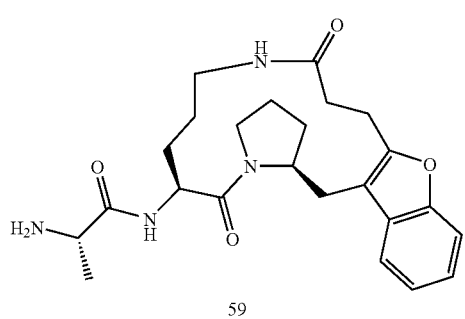

59

The Preparation of Ornithine-Derived Lactam (59)

A. 3-{3-[1-(5-Benzyloxycarbonylamino-2-tert-butoxycarbonylamino-pentanoyl)-pyrrolidin-2-ylmethyl]-benzofuran-2-yl}-propionic acid ethyl ester (53): A solution containing Boc-L-ornithine (2.3 g, 6.3 mmol) in NMP (5 mL) was treated with HATU (2.4 g, 6.3 mmol) followed by NMM (1.5 mL, 13.7 mmol) at ambient temperature. After 10 min, amine 48 (1.6 g, 5.3 mmol) in NMP (10 mL) was added in a dropwise fashion. After 16 h, the reaction mixture was diluted with diethyl ether and washed successively with NaHCO$_3$, 1 M HCl, water, and brine. The organic extract was dried over anhydrous Na$_2$SO$_4$, filtered and concentrated to afford 3.0 g (87%) of 53 as an orange-colored oil which was used without further purification. $^1$H NMR (CDCl$_3$, 300 MHz) δ7.78-7.75 (m, 1H), 7.40-7.20 (m, 8H), 5.48 (d, J=8.4 Hz, 1H), 5.10 (s, 2H), 4.48-4.42 (m, 1H), 4.17-4.09 (m, 2H), 3.64-3.56 (m, 1H), 3.27-3.19 (m, 1H), 3.12 (app t, J=7.8 Hz, 1H), 2.81-2.74 (m, 2H), 2.52-2.35 (m, 1H), 2.09-1.95 (m, 2H), 1.83-1.63 (m, 4H), 1.45 (s,-9H) 1.29-1.19 (m, 6H) ppm.

B. 3-{3-[1-(5-Benzyloxycarbonylamino-2-tert-butoxycarbonylamino-pentanoyl)-pyrrolidin-2-ylmethyl]-benzofuran-2-yl}-propionic acid (54): A solution containing the crude 53 (3.0 g, 4.6 mmol) in THF (20 mL) was treated with 3 M NaOH (8 mL) at ambient temperature. The reaction mixture was then warmed to gentle reflux and maintained for 2.5 h. The reaction mixture was concentrated in vacuo and the residue was dissolved in EtOAc. The organic solution was washed with 1 N HCl then dried over anhydrous Na$_2$SO$_4$, filtered and concentrated to afford ~3 g (quant.) of 54 as an off-white-colored foam which was used directly without further purification. $^1$H NMR (CDCl$_3$, 300 MHz) δ7.69-7.67 (m, 1H), 7.39-7.20 (m, 8H), 5.70 (d, J=8.4 Hz, 1H), 5.13-5.09 (m, 2H), 4.50-4.45 (m, 1H), 3.67-3.54 (m, 1H), 3.22-3.18 (m, 2H), 3.13 (t, J=6.9 Hz, 1H), 2.85-2.78 (m, 2H), 2.09-1.97 (m, 3H), 1.76-1.62 (m, 4H), 1.43 (s, 9H) ppm.

C. 3-{3-[1-(5-Amino-2-tert-butoxycarbonylamino-pentanoyl)-pyrrolidin-2-ylmethyl]-benzofuran-2-yl}-propionic acid (55): A solution of the crude 54 (~3 g, 4.8 mmol) in MeOH (30 mL) was charged with 10% Pd-on-carbon (~1 g) and placed under an atmosphere of hydrogen gas (45 PSI). The reaction mixture was shaken using a Parr apparatus for 2 h. After removal of the catalyst by filtration over celite, the clarified filtrate was concentrated in vacuo. The crude residue was taken up in DCM and dried using anhydrous Na$_2$SO$_4$, filtered and concentrated to afford 2.3 g (quant.) of 55 as a foamy residue which was used without further purification. $^1$H NMR (CDCl$_3$, 300 MHz) δ7.51 (m, 1H), 7.34-7.32 (m, 1H), 7.18-7.15 (m, 2H), 6.19 (m, 1H), 4.36 (m, 2H), 3.62-3.48 (m, 2H), 3.10-2.99 (m, 2H), 2.85-1.81 (m, 2H), 2.66-2.60 (m, 2H), 1.99-1.71 (m, 6H), 1.41 (s, 9H) ppm. Mass spectrum, m/z 488 [M+H]$^+$.

D. Boc-Protected Des-Alanine Ornithine-Derived Lactam (56): A solution containing 55 (2.3 g, 4.7 mmol) in 1:1 NMP/DCM (30 mL) was treated with HATU (2.1 g, 5.5 mmol) and NMM (0.6 mL, 5.5 mmol) at ambient temperature. After 18 h, the reaction mixture was diluted with diethyl ether and washed successively with aqueous Na$_2$SO$_4$, dilute aqueous HCl, water, brine, then dried over anhydrous Na$_2$SO$_4$, filtered and concentrated to afford 1.5 g (68%) of 56 as an off-white-colored foam which was used without further purification. $^1$H NMR (CDCl$_3$, 300 MHz) δ7.70-7.66 (m, 1H), 7.33 (m, 1H), 7.19-7.18 (m, 2H), 5.70 (m, 1H), 4.42 (m, 1H), 4.10 (m, 1H), 3.55 (m, 3H), 3.24-3.09 (m, 4H), 2.61-2.46 (m, 2H), 1.63 (m, 7H), 1.44 (s, 9H) ppm. Mass spectrum, m/z 470 [M+H]$^+$, 492 [M+Na]$^+$.

E. Des-Alanine Ornithine-Derived Lactam (57): To a solution of crude 56 (1.5 g, 3.1 mmol) in DCM (20 mL) was added TFA (4 mL) at ambient temperature. After 2 h, the solvent was removed under reduced pressure. The residue was dissolved in EtOAc and washed with aqueous NaHCO$_3$, and brine. The combined aqueous washes were back extracted with 5% MeOH/DCM. The combined organic extracts were dried over anhydrous Na$_2$SO$_4$, filtered and concentrated to afford 0.8 g (68%) of 57 as an off-white-colored foam which was used directly in the next reaction. $^1$H NMR (CDCl$_3$, 300 MHz) δ7.41-7.38 (m, 1H), 7.27-7.20 (m, 3H), 5.99 (d, J=9.3 Hz, 1H), 4.39-4.33 (m, 1H), 3.96-3.84 (m, 1H), 3.70-3.65 (m, 2H), 3.55-3.38 (m, 2H), 3.20-3.05 (m, 2H), 2.90-2.83 (m, 3H), 2.77-2.71 (m, 2H), 2.66-2.62 (m, 2H), 2.19-1.98 (m, 2H), 1.78-1.66 (m, 2H), 1.38-1.08 (m, 2H) ppm.

F. Boc-Protected Ornithine-Derived Lactam (58): A solution containing Boc-L-alanine (526 mg, 2.8 mmol) in NMP (5 mL) was treated with HATU (1.1 g, 2.9 mmol) followed by NMM (0.3 mL, 2.9 mmol) at ambient temperature. After 10 min, crude amine 57 (0.8 mg, 2.2 mmol) in NMP (10 mL) was added in a dropwise fashion. After 2 d, the reaction mixture was diluted with diethyl ether and washed successively with NaHCO$_3$, 1 M HCl, water, and brine. The organic extract was dried over anhydrous Na$_2$SO$_4$, filtered and concentrated to afford ~1 g (84%) of 58 as a yellow-colored oil which was used without further purification. Mass spectrum: m/z 541 [M+H]$^+$, and 563 [M+Na]$^+$.

G. Ornithine-derived Lactam (59): To a solution of crude 58 (~1 g, 1.9 mmol) in DCM (10 mL) was added TFA (4 mL) at ambient temperature. After 1 h, the solvent was removed under reduced pressure. The residue was dissolved in EtOAc and washed with aqueous NaHCO$_3$, and brine. The combined aqueous washes were back extracted with 5% MeOH/DCM and the combined organic extracts were dried over anhydrous Na$_2$SO$_4$, filtered and concentrated. A portion of the crude product was purified by reverse-phase HPLC (C 18, 10-100% ACN/water containing 0.1% HOAc) to afford 28 mg of 59 as a white solid. $^1$H NMR (DMSO, 300 MHz) δ8.14 (m, 1H), 7.88 (m, 1H), 7.68-7.66 (m, 1H), 7.35 (m, 1H), 7.12 (m, 2H), 4.43 (m, 1H), 4.12 (m, 1H), 3.48 (m, 2H), 2.91 (m, 4H), 1.48-1.36 (m, 4H), 1.10 (d, J=6.3 Hz, 3H) ppm. Mass spectrum: m/z 441 [M+H]$^+$.

TABLE 11

(E12-1)

| Entry | A$_1$ | R$_{1b}$ | Y | Z | X$_2$ | R$_{11, 12}$, R$_{14-17}$ | MS (M + H)$^+$ | K$_D$ Range |
|---|---|---|---|---|---|---|---|---|
| 11-91 | H | Me | Y linked with R$_{11}$ | H | O | R$_{11}$ linked with Y | 441.3 | B |

TABLE 12

(E12-2)

| Entry | A$_1$ | R1 | Y | Z | X$_2$ | R$_{11, 12}$, R$_{14-17}$ | MS (M + H)$^+$ | K$_D$ Range |
|---|---|---|---|---|---|---|---|---|
| 12-92 | H | Me | Y linked with R$_{11}$ | H | O | R$_{11}$ linked with Y | 455.2 | C |

EXAMPLE 13

This example illustrated pyrrolidine derivatives of Table 13.

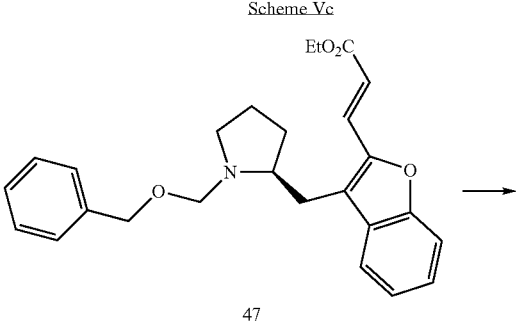

Scheme Vc

47

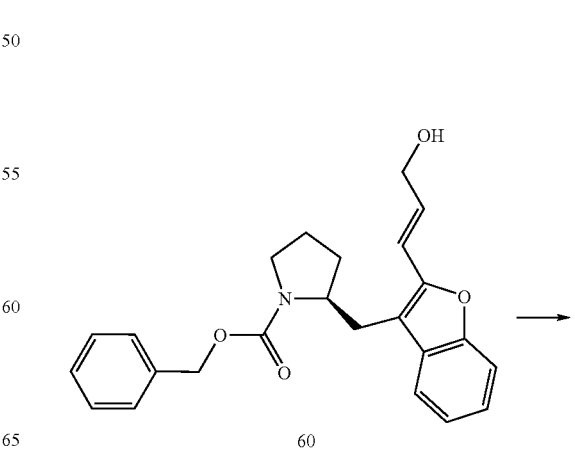

60

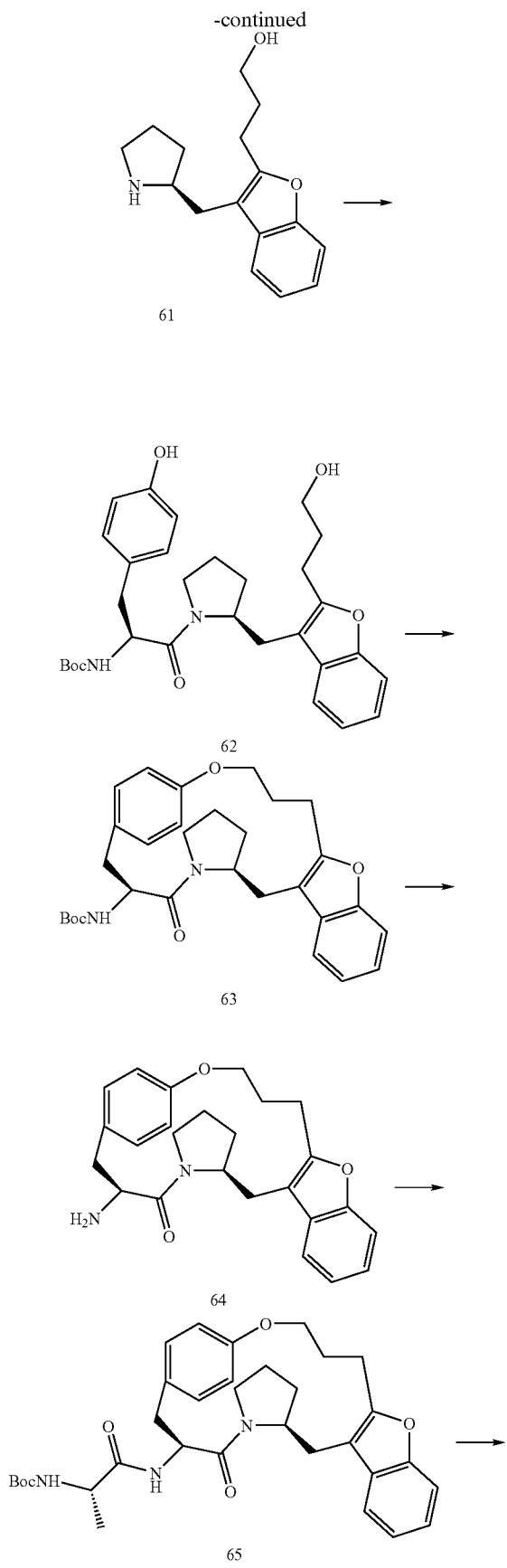

The Preparation of Tyrosine-Derived Cyclic Ether (66)

A. 2-[2-(3-Hydroxy-propenyl)-benzofuran-3-ylmethyl]-pyrrolidine-1-carboxylic acid benzyl ester (60): At −78° C., BF₃ etherate (0.6 mL, 4.8 mmol) was added to a solution containing 47 (1.7 g, 3.9 mmol) in anhydrous DCM (40 mL). After 10 min, DIBAL (1 M/DCM, 10 mL, 10 mmol) was added dropwise from an addition funnel. After 5 min following the complete addition of the DIBAL solution, EtOAc (10 mL) was added to quench the excess reagent. Dilute aqueous HCl was slowly added and the reaction mixture was allowed to slowly warm to ambient temperature. The product was extracted with DCM and EtOAc and the combined organic extracts were washed with dilute aqueous HCl, water, brine, dried over anhydrous Na₂SO₄, filtered and concentrated. The crude product was purified by flash silica gel chromatography (EtOAc/hexane, 1:2) to afford 1.1 g (72%) of 60 as a yellow-colored oil. $^1$H NMR (CDCl₃, 300 MHz) δ7.65 & 7.03 (rotamer, d and app t, J=6.9, 7.8 Hz, 1H), 7.38 (M, 5H), 7.26-7.19 (m, 2H), 6.70-6.52 (m, 2H), 5.26-5.14 (m, 2H), 4.38 (m, 1H), 4.28 (m, 1H), 4.14 (m, 1H), 3.43 (m, 2H), 3.27 & 3.02 (rotamer, 2 m, 1H), 2.76-2.68 (m, 1H), 2.45 (m, 1H), 1.77-1.68 (m, 5H) ppm.

B. 3-(3-Pyrrolidin-2-ylmethyl-benzofuran-2-yl)-propan-1-ol (61): A mixture of 60 (1.1 g, 2.8 mmol) and 10% Pd-on-carbon (1 g) in MeOH (40 mL) was placed under an atmosphere of hydrogen gas (45 PSI) and shaken for 2 h using a Parr apparatus. The catalyst was removed by filtration through a bed of celite and the clarified filtrate was concentrated in vacuo to afford 725 mg (quant.) of 61 as a yellow oil which was used without further purification. $^1$H NMR (CDCl₃, 300 MHz) δ7.47-7.36 (m, 2H), 7.21-7.17 (m, 2H), 4.59 (br s, 2H), 3.57-3.50 (m, 2H), 3.40-3.31 (m, 1H), 3.08-2.94 (m, 1H), 2.89-2.69 (m, 2H), 2.05-1.95 (m, 2H), 1.93-1.49 (m, 2H) ppm.

C. (1-(4-Hydroxy-benzyl)-2-{2-[2-(₃-hydroxy-propyl)-benzofuran-3-ylmethyl]-pyrrolidin-1-yl}-2-oxo-ethyl)-carbamic acid tert-butyl ester (62): A solution containing Boc-L-tyrosine (577 mg, 2.1 mmol) and HATU (716 mg, 1.8 mmol) in anhydrous NMP (6 mL) was treated with NMM (0.3 mL, 2.7 mmol) at ambient temperature. After 10 min, a solution containing 61 (429 mg, 1.7 mmol) in NMP (5 mL) was added. After 2 d, the reaction mixture was diluted with water and the product was extracted with diethyl ether. The combined ether extracts were washed with water and dilute aque ous NaHCO₃, brine, dried over anhydrous Na₂SO₄, filtered and concentrated. The crude product was purified by flash silica gel chromatography (10% MeOH/DCM) to afford 821 mg (92%) of 62 as a pale yellow foam. $^1$H NMR (CDCl₃, 300 MHz) δ8.54 (br 2, 1H), 7.66-7.63 (m, 1H), 7.36-7.32 (m, 1H), 7.21-7.06 (m, 5H), 6.83 (d, J=8.4 Hz, 2H), 5.58 (d, J=9.0 Hz, 1H), 4.64-4.56 (m, 1H), 4.34-4.31 (m, 1H), 3.92-3.88 (m, 1H), 3.70 (app t, J=5.7 Hz, 2H), 3.51-3.26 (m, 1H), 3.18-2.79 (m, 4H), 2.01-1.97 (m, 2H), 1.69-1.47 (m, 1H), 1.42 (s, 9H) ppm.

D. Boc-Protected Des-Alanine Tyrosine-Derived Cyclic Ether (63): To a solution containing 62 (821 mg, 1.6 mmol) in DCM (40 mL) was added Ph₃P (431 mg, 1.6 mmol) and ADDP (491 mg, 1.9 mmol) at ambient temperature. After 16 h, the reaction mixture was concentrated in vacuo then redissolved in diethyl ether. The insoluble white solid was removed by filtration and the clarified filtrate was concentrated. The crude product was purified by flash silica gel chromatography (EtOAc/hexane, 1:2 to 1:1) to afford 160 mg (19%) of 63 as a light yellow-colored foam. $^1$H NMR (CDCl₃, 300 MHz) δ7.47 (d, J=7.5 Hz, 1H), 7.34 (d, J=7.8 Hz, 1H), 7.28-7.24 (m, 2H), 7.22-7.11 (m, 2H), 7.00 (dd, J=2.7, 8.1 Hz, 1H), 6.69 (dd, J=3.0, 8.7 Hz, 1H), 5.28 (d, J=9.6 Hz, 1H), 4.88-4.79 (m, 1H), 4.51-4.41 (m, 1H), 4.23-4.17 (m, 1H), 3.97-3.89 (m, 1H), 3.84-3.76 (m, 1H), 3.46-3.29 (m, 2H), 2.75-2.62 (m, 4H), 2.17-2.09 (m, 1H), 1.99-1.90 (m, 1H), 1.72-1.54 (m, 2H), 1.45 (s, 9H) ppm.

E. Des-Alanine Tyrosine-Derived Cyclic Ether (64): To a solution of 63 (160 mg, 0.32 mmol) in DCM (10 mL) was added TFA (2 mL) at ambient temperature. After 1.5 h, the solvent was removed under reduced pressure. The residue was dissolved in EtOAc and washed with aqueous NaHCO₃, brine, dried over anhydrous Na₂SO₄, filtered and concentrated to afford 130 mg (quant.) of 64 as an off-white-colored solid which was used directly in the next reaction. $^1$H NMR (CDCl₃, 300 MHz) δ7.46 (d, J=7.8 Hz, 1H), 7.34 (d, J=8.4 Hz, 1H), 7.21-7.19 (m, 2H), 7.16-7.10 (m, 2H), 6.97 (dd, J=2.4, 8.1 Hz, 1H), 6.70-6.68 (m, 1H), 4.47 (m, 1H), 4.21-4.13 (m, 2H), 3.93 (t, J=9.3 Hz, 1H), 3.51-3.36 (m, 4H), 2.73-2.68 (m, 4H), 2.15-2.07 (m, 1H), 1.98-1.90 (m, 1H), 1.70-1.46 (m, 3H), 1.19-1.13 (m, 1H), 0.64-0.55 (m, 1H) ppm.

F. Boc-Protected Tyrosine-Derived Cyclic Ether (65): A solution containing Boc-L-alanine (63 mg, 0.33 mmol) in NMP (3 mL) was treated with HATU (125 mg, 0.33 mmol) followed by NMM (0.1 mL, 0.9 mmol) at ambient temperature. After 10 min, crude amine 64 (125 mg, 0.31 mmol) in NMP (5 mL) was added in a dropwise fashion. After 16 h, the reaction mixture was diluted with diethyl ether and washed successively with NaHCO₃, 1 M HCl, water, and brine. The organic extract was dried over anhydrous Na₂SO₄, filtered and concentrated. The crude product was purified by flash silica gel chromatography (EtOAc/hexane, 1:1 to 2:1) to afford 137 mg (76%) of 65 as a light yellow-colored solid. $^1$H NMR (CDCl₃, 300 MHz) δ7.46 (d, J=7.8 Hz, 1H), 7.34 (d, J=7.8 Hz, 1H), 7.19-7.12 (m, 3H), 7.05-6.99 (m, 2H), 6.70 (dd, J=2.4, 8.4 Hz, 1H), 5.14-5.08 (m, 2H), 4.48-4.42 (m, 1H), 4.26-4.18 (m, 2H), 3.93 (app t, J=9.3 Hz, 1H), 3.84-3.76 (m, 1H), 3.47-3.31 (m, 2H), 2.84-2.64 (m, 4H), 2.15-2.08 (m, 1H), 1.97-1.93 (m, 1H), 1.71-1.52 (m, 3H), 1.48 (s, 9H), 1.38 (d, J=7.2 Hz, 3H), 1.18-1.12 (m, 1H), 0.64-0.56 (m, 1H) ppm.

G. Tyrosine-Derived Cyclic Ether (66): To a solution of 65 (137 mg, 0.23 mmol) in DCM (10 mL) was added TFA (2 mL) at ambient temperature. After 1.5 h, the solvent was removed under reduced pressure. The residue was dissolved in EtOAc and washed with aqueous NaHCO₃, brine, dried over anhydrous Na₂SO₄, filtered and concentrated. The crude product was purified by reverse-phase HPLC (C18, 10-100% ACN/water containing 0.1% HOAc) to afford 90 mg (82%) of 66 as a white solid. $^1$H NMR (DMSO, 300 MHz) δ8.23 (d, J=6.9 Hz, 1H), 7.46-7.39 (m, 3H), 7.23-7.12 (m, 2H), 7.01-6.99 (m, 2H), 6.85-6.82 (m, 1H), 4.86(m, 1H), 4.27 (m, 1H), 4.16 (m, 1H), 3.98-3.84 (m, 1H), 3.44-3.33 (m, 1H), 3.16-3.10 (m, 1H), 2.76-2.67 (m, 3H), 1.99 (m, 1H), 1.57 (app t, J=5.7 Hz, 2H), 1.45-1.39 (m, 1H), 1.16 (d, J=6.3 Hz, 3H), 1.02-0.97 (m, 1H), 0.58-0.49 (m, 1H) ppm. Mass spectrum: m/z 476.2 [M+H]⁺.

TABLE 13

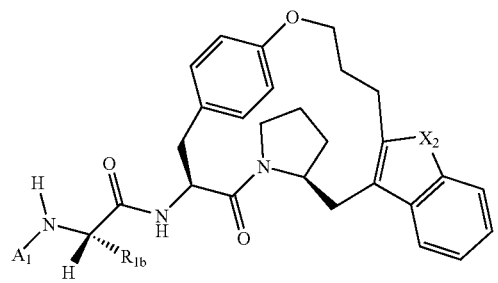

(E13)

| Entry | A₁ | R₁ᵦ | Y | Z | X₂ | R₁₁,₁₂, R₁₄₋₁₇ | MS (M + H)⁺ | K_D Range |
|---|---|---|---|---|---|---|---|---|
| 13-93 | H | Me | Y linked with R₁₁ | H | O | R₁₁ linked with Y | 476.2 | B |

EXAMPLE 14

This example illustrated pyrrolidine derivatives of Table 14

Scheme VI

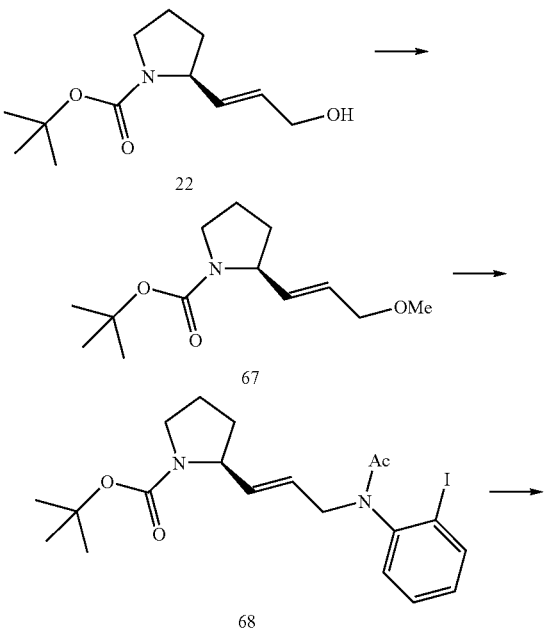

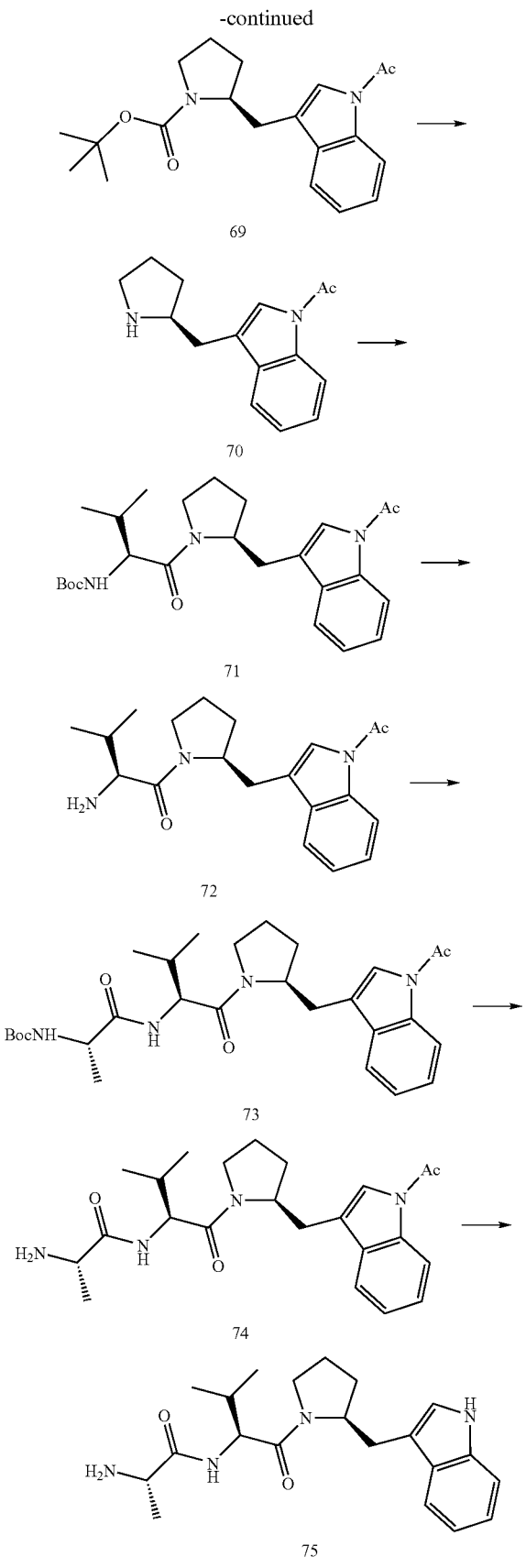

The Preparation of 2S-Amino-N-{1S-[2S-(1H-indol-3-ylmethyl)-pyrrolidine-1-carbonyl]-2-methyl-propyl}-propionamide (76)

A. trans-2S-(3-Methanesulfonyloxy-propenyl)-pyrrolidine-1-carboxylic acid tert-butyl ester (67): To a solution of 22 (2 g, 8.8 mmol) in DCM (10 mL) was added triethylamine (2.5 mL, 17.6 mmol). The solution was cooled in ice bath and methanesulfonyl chloride (0.74 mL, 9.68 mmol) was added dropwise and stirred at room temperature for 30 min. Water (10 mL) was added and the product was extracted with DCM (3×50 mL). The organic layers were combined and washed with 5 mL 1N HCl, water (10 mL), and brine, and dried over anhydrous $Na_2SO_4$. Solvent evaporated under reduced pressure to obtained 9.5 g of 67 which was used without purification. $^1$H NMR (CDCl$_3$, 300 MHz): δ 4.4-4.0 (m, 2 H), 3.42-3.21 (m, 3H), 3.0 (s, 3H), 2-1.6 (m, 4H), 1.42 (s, 9H) ppm.

B. trans-2S-{3-[Acetyl-(2-iodo-phenyl)-amino]-propenyl}-pyrrolidine-1-carboxylic acid tert-butyl ester (68): A solution of o-iodoacetanilide (1.1 g, 4.21 mmol) in DMF (10 mL) was cooled in ice bath and NaH (60% dispersion in mineral oil, 0.24 g, 6.31 mmol) was added in portions and stirred at room temperature for 10 min. Crude mesylate 67 (1.28 g, 4.21 mmol) in DMF (5 mL) was added dropwise at room temperature and stirred for 30 min. Water (10 mL) was added and the product was extracted with diethyl ether (3×50 mL). The combined ether extracts were washed with water (3×50 mL) and brine, dried over $Na_2SO_4$. Solvent evaporated under reduced pressure and purified by flash silica gel chromatography (3:1 hexanes/ethyl acetate) to afford 1.17 g of 68 as a white solid. $^1$H NMR (CDCl$_3$, 300 MHz): δ 7.85 (d, J=9.9 Hz, 1H), 7.4-7.0 (m, 3H), 5.6 (m, 1H), 5.28 (m, 1H), 4.86 (m, 1H), 3.3 (m, 3H), 2.0-1.6 (m, 4H), 1.4 (s, 9H) ppm.

C. 2S-(1-Acetyl-1H-indol-3-ylmethyl)-pyrrolidine-1-carboxylic acid tert-butyl ester (69): To a solution of 68 (1.1 g, 2.33 mmol) in DMF (15 mL) was added $K_2CO_3$ (0.41 g, 3.02 mmol), $NaHCO_2$ (0.16 g, 2.44 mmol) followed by tetrabutylammonium chloride (0.64 g, 2.33 mmol) and Pd(OAc)$_2$ (0.02 g, 0.07 mmol) and the reaction flask was immersed in a pre-heated oil bath (100° C.). After 40 min., water (10 mL) was added and the product was extracted with diethyl ether (3×50 mL). The diethyl ether extracts were washed with water (3×50 mL), brine and dried over $Na_2SO_4$. Solvent was evaporated under reduced pressure and purified by flash silica gel chromatography (3:1 hexanes/ethyl acetate) to afford 0.37 g of 69 as white solid. $^1$H NMR (CDCl$_3$, 300 MHz): δ 8.4 (s, 1H), 7.78-7.6 (dd, J=10.7, 10.7 Hz, 1H), 4.2-4.0 (m, 1H), 3.45-3.0 (m, 3H), 2.7-2.6 (m, 1H), 2.6 (s, 3H), 1.9-1.65 (m, 4H), 1.5 (s, 9H) ppm.

D. 1-(3-Pyrrolidin-2S-ylmethyl-indol-1-yl)-ethanone (70): To a solution of 69 (0.37 g, 1.08 mmol) in DCM (20 mL) was added TFA (4 mL) and stirred at room temperature for 30 min. Aqueous NaHCO$_3$ (5 mL) was added and the reaction mixture was concentrated under reduced pressure. The product was extracted with DCM (3×50 mL) and the organic extract was washed with aqueous NaHCO$_3$, water and brine, and dried over anhydrous $Na_2SO_4$. Solvent was removed under reduced pressure and purified by silica gel column chromatography (10:1 DCM/MeOH) to afford 0.26 g of 70 as white solid. $^1$H NMR (CDCl$_3$, 300 MHz): δ 8.6 (d, J=11 Hz, 1H), 7.5 (d, J=11 Hz, 1H),7.4-7.2 (m, 3H), 3.8-3.6 (m, 1H), 3.2-2.9 (m, 4H),2.8 (s, 3H), 2.2-1.6 (m, 4H) ppm.

E. {1S-[2S-(1-Acetyl-1H-indol-3-ylmethyl)-pyrrolidine-1-carbonyl]-2-methyl-propyl}-carbamic acid tert-butyl ester (71): To a solution of Boc-L-valine (0.25 g, 1.18 mmol) in NMP (5 mL), was added HATU (0.44 mg, 1.18 mmol) followed by N (0.3 mL, 2.67 mmol). After 5 min., added 70 (0.25 g, 0.11 mmol) and stirred at room temperature for 30 min. Ethyl acetate (20 mL) was added and the organic solution was washed with aqueous NaHCO$_3$ (10 mL), 1 N HCl (10 mL), water, and brine, dried over Na$_2$SO$_4$. Solvent was removed under reduced pressure and the product was purified by flash silica gel chromatography to afford 0.36 mg of 71 as a white solid. $^1$H NMR (CDCl$_3$, 300 MHz): δ 8.4 (m, 1H), 7.88 (d, J=11 Hz, 1H), 7.4-7.2 (m, 3H), 4.4-4.2 (m, 1H), 3.8-3.4 (m, 3H), 3.38 (d, J=11 Hz, 1H), 2.65 (d, J=11 Hz, 1H), 2.6 (s, 3H), 2.5-2.4 (m, 1H), 2.1-1.7 (m, 4H), 1.4 (s, 9H), 1.05 (d, J=5.5 Hz, 3H), 0.95 (d, J=5.5 Hz, 3H) ppm.

F. 1-[2S-(1-Acetyl-1H-indol-3-ylmethyl)-pyrrolidin-1-yl]-2S-amino-3-methyl-butan-1-one (72): To a solution of 71 (0.36 g, 0.81 mmol) in DCM (20 mL) was added TFA (4 mL) and the reaction mixture was stirred at room temperature for 30 min. Aqueous NaHCO$_3$ was added to the reaction mixture and TFA and DCM were removed under reduced pressure. The product was extracted with DCM (3×50 mL) and the combined DCM extracts were washed with water and brine and dried over anhydrous Na$_2$SO$_4$. Solvent was removed under reduced pressure and the product was purified by flash silica gel chromatography (10:1 DCM/MeOH) to afford 0.27 g of 72 as white solid. $^1$H NMR (CDCl$_3$, 300 MHz): δ 8.4 (m, 1H), 7.88 (d, J=11 Hz, 1H), 7.4-7.2 (m, 3H), 4.4-4.2 (m, 1H), 3.8-3.4 (m, 3H), 3.38 (d, J=11 Hz, 1H), 2.65 (d, J=11 Hz, 1H), 2.6 (s, 3H), 2.5-2.4 (m, 1H), 2.1-1.7 (m, 4H), 1.05 (d, J=5.5 Hz, 3H), 0.95 (d, J=5.5 Hz, 3H) ppm.

G. (1S-{1S-[2S-(1-Acetyl-1H-indol-3-ylmethyl)-pyrrolidine-1-carbonyl]-2-methyl-propylcarbamoyl}-ethyl)-carbamic acid tert-butyl ester (73): To a solution of BOC-L-alanine (0.13 g, 0.38 mmol) in NMP (3 mL) was added HATU (0.16 mg, 0.41 mmol) followed by NMM (0.1 mL, 0.95 mmol). After 5 min., 72 (0.12 g, 0.34 mmol) was added and the reaction mixture was stirred at room temperature for 30 min. Ethyl acetate (20 mL) was added to the reaction mixture and the organic solution was washed with aqueous NaHCO$_3$ (10 mL), 1 N HCl (10 mL), water, and brine, dried over Na$_2$SO$_4$. Solvent was removed under reduced pressure and the product was purified by flash silica gel chromatography to afford 0.15 mg of 73 as white solid. $^1$H NMR (CDCl$_3$, 300 MHz): δ 8.4 (m, 1H), 7.88 (d, J=10.9 Hz, 1H), 7.4-7.2 (m, 3H), 7.0-6.8 (m 1H), 4.6 (m, 1H), 4.5-4.4 (m, 1H), 4.2 (m, 1H), 3.8-3.6 (m, 2H), 3.38 (d, J=10.9 Hz, 1H), 2.65 (d, J=10.9 Hz, 1H), 2.6 (s, 3H), 2.5-2.4 (m, 1H), 2.1-1.7 (m, 4H), 1.45 (s, 9H), 1.4 (d, J=10.9 Hz, 3H), 1.05 (d, J=5.5 Hz, 3H), 0.95 (d, J=5.5 Hz, 3H) ppm.

H. N-{1S-[2S-(1-Acetyl-1H-indol-3-ylmethyl)-pyrrolidine-1-carbonyl]-2-methyl-propyl}-2S-amino-propionamide (74): To a solution of 73 (0.15 g, 0.29 mmol) in DCM (20 mL) was added TFA (4 mL) and the reaction mixture was stirred at room temperature for 30 min. Aqueous NaHCO$_3$ was added to the reaction mixture and TFA and DCM were removed under reduced pressure. The product was extracted with DCM (3×50 mL) and the DCM extracts were washed with water, brine, and dried over anhydrous Na$_2$SO$_4$. Solvent was removed under reduced pressure and the product was purified by flash silica gel chromatography (10:1 DCM/MeOH) to afford 0.12 g of 74 as a white solid. $^1$H NMR (CDCl$_3$, 300 MHz): δ 8.4 (m, 1H), 7.88 (d, J=10.9 Hz, 1H), 7.85 (d, J=10.9 Hz, 1H), 7.4-7.2 (m, 3H), 4.6 (m, 1H), 4.5-4.4 (m, 1H), 3.8 (m, 1H), 3.75-3.4 (m, 2H), 3.38 (d, J=10.9 Hz, 1H), 2.65 (d, J=10.9 Hz, 1H), 2.6 (s, 3H), 2.5-2.4 (m, 1H), 2.1-1.7 (m, 4H), 1.4 (d, J=10.9 Hz, 3H), 1.05 (d, J=5.5 Hz, 3H), 0.95 (d, J=5.5 Hz, 3H) ppm.

2S-Amino-N-{1S-[2S-(1H-indol-3-ylmethyl)-pyrrolidine-1-carbonyl]-2-methyl-propyl}-propionamide (75): To a solution of 74 (0.12 g, 0.291 mmol) in dry MeOH (3 mL) was added 3 mL of 10% NaOH/MeOH. After 15 min., water (2 mL) was added to the reaction mixture and the solvent was removed under reduced pressure. The product was extracted with ethyl acetate (3×50 mL) and the organic extracts were washed with water, brine, and dried over Na$_2$SO$_4$. Solvent was removed under reduced pressure and the product was purified by flash silica gel chromatography (10:1 DCM/MeOH) to afford 0.06 g of 75 as white solid. $^1$H NMR (CDCl$_3$, 300 MHz): δ 8.4 (m, 1H), 7.88 (d, J=10.9 Hz, 1H), 7.85 (d, J=10.9 Hz, 1H), 7.4-7.2 (m, 3H), 4.6 (m, 1H), 4.5-4.4 (m, 1H), 3.8 (m, 1H), 3.75-3.4 (m, 2H), 3.38 (d, J=10.9 Hz, 1H), 2.65 (d, J=10.9 Hz, 1H), 2.5-2.4 (m, 1H), 2.1-1.7 (m, 4H), 1.4 (d, J=10.9 Hz, 3H), 1.05 (d, J=5.5 Hz, 3H), 0.95 (d, J=5.5 Hz, 3H) ppm.

TABLE 14

(E14)

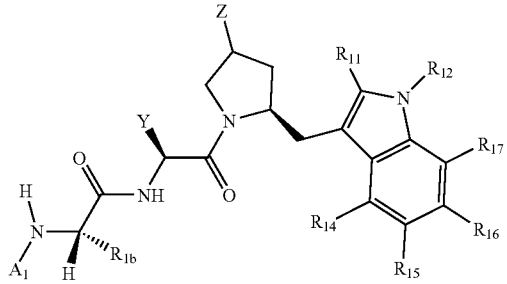

| Entry | $A_1$ | $R_{1b}$ | Y | Z | $R_{12}$ | $R_{14-17}$ | $R_{11}$ | MS $(M+H)^+$ | $K_D$ Range |
|---|---|---|---|---|---|---|---|---|---|
| 14-94 | H | Me | iPr | H | Ac | H | H | 413.2 | A |
| 14-95 | H | H | iPr | H | Ac | H | H | 399.3 | D |
| 14-96 | Me | Me | tBu | H | Ac | 6-F ($R_{16}$) | H | 459.2 | B |
| 14-97 | Me | Me | cHex | H | Ac | 6-F ($R_{16}$) | H | 485.3 | B |
| 14-98 | H | Me | iPr | H | Ac | 7-Me ($R_{17}$) | H | 426.8 | A |

TABLE 14-continued (E14)

| Entry | $A_1$ | $R_{1b}$ | Y | Z | $R_{12}$ | $R_{14-17}$ | $R_{11}$ | MS $(M+H)^+$ | $K_D$ Range |
|---|---|---|---|---|---|---|---|---|---|
| 14-99 | H | Me | iPr | H | H | H | H | 371.3 | B |
| 14-100 | H | Me | iPr | H | H | 7-Me ($R_{17}$) | H | 385.5 | A |
| 14-101 | Boc | Me | iPr | H | Boc | H | H | 571.3 | D |
| 14-102 | H | Me | iPr | H | MeC≡CCH$_2$ | H | H | 423.3 | B |
| 14-103 | H | Me | iPr | H | HC≡CCH$_2$ | H | H | 409.3 | A |
| 14-104 | Me | Me | cHex | H | H | 6-F ($R_{16}$) | H |  | B |
| 14-105 | H | H | tBu | H | Ac | 6-F | H |  | D |

EXAMPLE 15

This example illustrated pyrrolidine derivatives of Table 15.

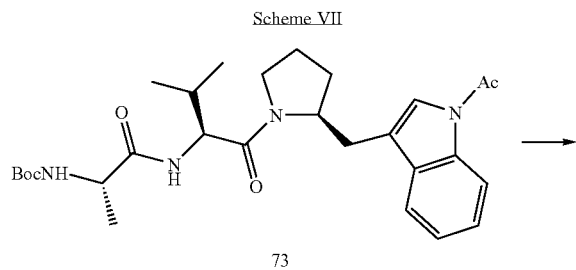
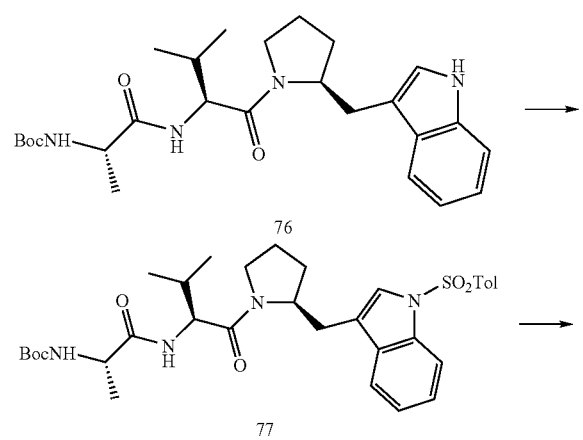
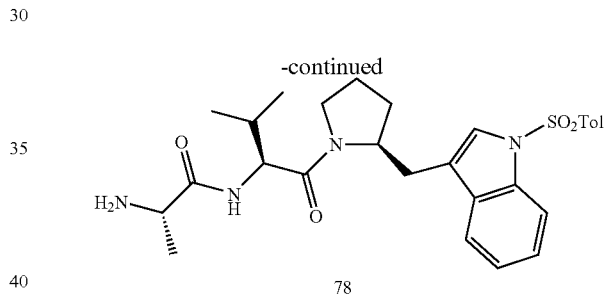

The Preparation of 2S-Amino-N-(2-methyl-1S-{2S-[1-(toluene-4-sulfonyl)-1H-indol-3-ylmethyl]-pyrrolidine-1-carbonyl}-propyl)-propionamide (78)

A. (1S-{1S-[2S-(1H-Indol-3-ylmethyl)-pyrrolidine-1-carbonyl]-2-methyl-propylcarbamoyl}-ethyl)-carbamic acid tert-butyl ester (76): To a solution of 73 (0.70 g, 1.36 mmol) in dry MeOH (10 mL) was added 5 mL of 10% NaOH/MeOH and stirred for 15 min. Water (5 mL) was added to the reaction mixture and the solvent removed under reduced pressure. The product was extracted with ethyl acetate (3×50 mL) and the organic extracts were washed with water, brine, and dried over Na$_2$SO$_4$. Solvent was removed under reduced pressure and the product was purified by flash silica gel chromatography (10:1 DCM/MeOH) to afford 0.53 g of 76 as a white solid. $^1$H NMR (CDCl$_3$, 300 MHz): δ 8.0 (s, 1H), 7.9 (d, J=9.9 Hz, 1H), 7.38 (d, J=9.9 Hz, 1H), 7.3-7.1 (m, 3H), 6.8 (m, 1H), 4.62 (m 1H), 4.5-4.4 (m, 1H), 4.4-4.0 (m, 2H), 3.7-3.5 (m, 2H), 3.4 (m, 1H), 2.5 (m, 1H), 2.2-1.8 (m, 4H), 1.48 (s, 9H), 1.35 (d, J=9.9 Hz, 3H), 1.05 (d, J=5.5 Hz, 3H), 0.95 (d, J=5.5 Hz, 3H) ppm.

B. [1S-(2-Methyl-1S-{2S-[1-(toluene-4-sulfonyl)-1H-indol-3-ylmethyl]-pyrrolidine-1-carbonyl}-propylcarbamoyl)-ethyl]-carbamic acid tert-butyl ester (77): To a solution of 76 (0.05 g, 0.11 mmol) in DCM (1 mL) was added NaOH (0.01 g, 0.13 mmol) and stirred at room temperature for 30 min. Tosyl chloride (0.03 g, 0.16 mmol) was added and the reaction mixture was heated to 35° C. for 1 h. Water (5 mL) was added to the reaction mixture and the product was extracted with DCM (3×30 mL). The DCM extracts were washed with water, brine, and dried over $Na_2SO_4$. Solvent was removed under reduced pressure and the product was purified by flash silica gel chromatography (3:1 hexane/ethyl acetate) to afford 61 mg of 77 as a white solid. $^1$H NMR ($CDCl_3$, 300 MHz): δ 7.95 (d, J=9.9 Hz, 1H), 7.82 (d, J=9.9 Hz, 1H), 7.7 (d, J=9.9 Hz, 2H), 7.4-7.2 (m, 5H), 6.8 (m, 1H), 4.6 (m, 1H), 4.4 (m, 1H), 4.3-4.18 (m, 2H), 3.8-3.5 (m, 2H), 3.3 (m, 1H), 2.45 (m, 1H), 2.35 (s, 3H), 2.2-1.8 (m, 4H), 1.43 (s, 9H), 1.38 (d, J=9.9 Hz, 3H), 1.05 (d, J=5.5 Hz, 3H), 0.95 (d, J=5.5 Hz, 3H) ppm.

C. 2S-Amino-N-(2-methyl-1S-{2S-[1-(toluene-4-sulfonyl)-1H-indol-3-ylmethyl]-pyrrolidine-1-carbonyl}-propyl)-propionamide (78): To a solution of 77 (0.06 g, 0.096 mmol) in DCM (10 mL) was added TFA (2 mL) and the reaction mixture was stirred at room temperature for 30 min. Aqueous $NaHCO_3$ was added to reaction mixture and TFA and DCM were removed under reduced pressure. The product was extracted with DCM (3×25 mL) and the DCM extracts were washed with water, brine, and dried over anhydrous $Na_2SO_4$. Solvent was removed under reduced pressure and the product was purified by flash silica gel chromatography (10:1 DCM/MeOH) to afford 0.04 g of 78 as a white solid. $^1$H NMR ($CDCl_3$, 300 MHz): δ 7.95 (d, J=9.9 Hz, 1H), 7.82 (d, J=9.9 Hz, 1H), 7.7 (d, J=9.9 Hz, 2H), 7.4-7.2 (m, 5H), 6.8 (m, 1H), 4.6 (m, 1H), 4.4 (m, 1H), 4.3-4.18 (m, 2H), 3.8-3.5 (m, 2H), 3.3 (m, 1H), 2.45 (m, 1H), 2.35 (s, 3H), 2.2-1.8 (m, 4H), 1.38 (d, J=9.9 Hz, 3H), 1.05 (d, J=5.5 Hz, 3H), 0.95 (d, J=5.5 Hz, 3H) ppm.

TABLE 15

(E15)

| Entry | $A_1$ | $R_{1b}$ | Y | Z | $R_{12}$ | $R_{14-17}$ | $R_{11}$ | MS $(M+H)^+$ | $K_D$ Range |
|---|---|---|---|---|---|---|---|---|---|
| 15-104 | H | Me | iPr | H | MeC≡$CCH_2$ | H | H | 423.3 | B |
| 15-105 | H | Me | iPr | H | HC≡$CCH_2$ | H | H | 409.3 | A |
| 15-106 | Me | Me | iPr | H | H | 7-BnO ($R_{17}$) | H | 491.3 | C |
| 15-107 | H | Me | iPr | H | Tosyl | H | H | 525.3 | A |
| 15-108 | Me | Me | tBu | H | H | 6-F ($R_{16}$) | 2-thiophenyl | 499.5 | A |

EXAMPLE 16

This example illustrated pyrrolidine derivatives of Table 16.

Scheme VIII

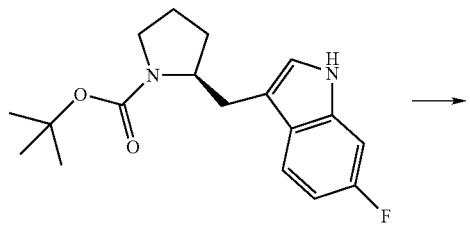

79

-continued
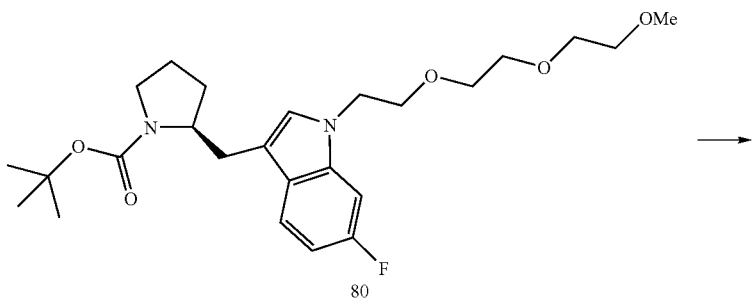
80
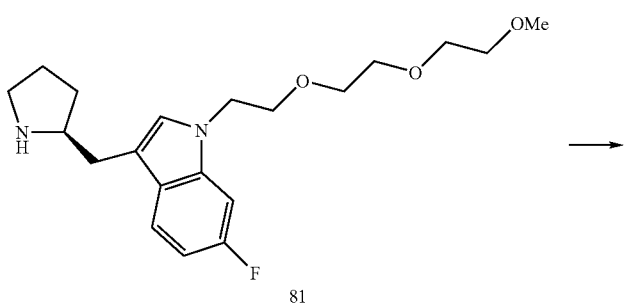
81
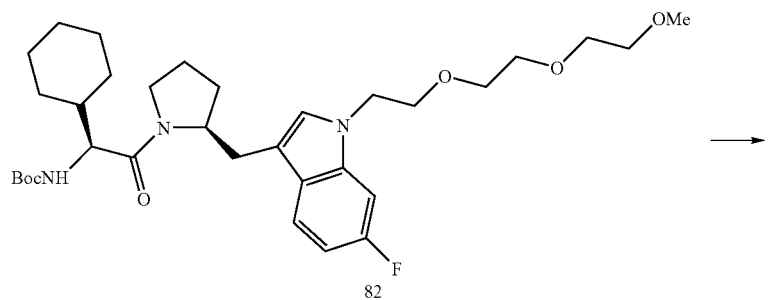
82
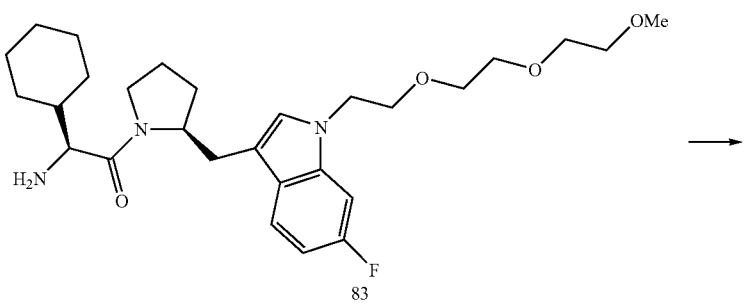
83
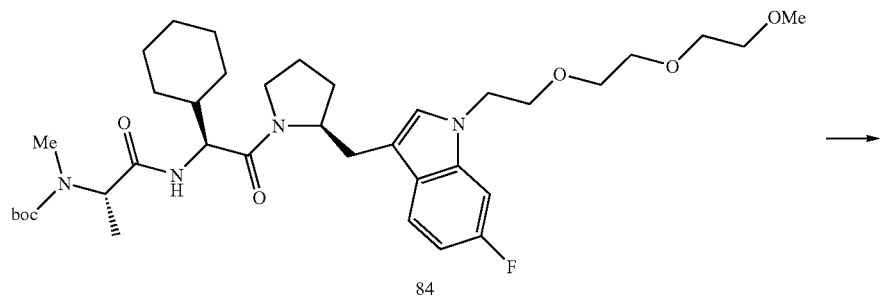
84

-continued

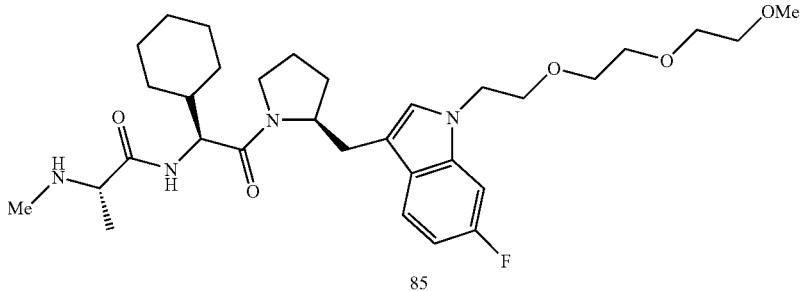

85

The Preparation of N-{1-Cyclohexyl-2-[2-(6-fluoro-1-{2-[2-(2-methoxy-ethoxy)-ethoxy]-ethyl}-1H-indol-3-ylmethyl)-pyrrolidin-1-yl]-2-oxo-ethyl}-2-methylamino-propionamide (85)

A. 2-(6-Fluoro-1-{2-[2-(2-methoxy-ethoxy)-ethoxy]-ethyl}-1H-indole-3-ylmethyl)-2S-pyrrolidine-1-carboxylic acid tert-butyl ester (80): To a suspension of NaH (72 mg, 1.8 mmol, 60% mineral oil suspension) in DMF (1 mL) was added 79 (180 mg, 0.60 mmol) in DMF (1 mL) at room temperature. The mixture was stirred for 1 h at room temperature, followed by addition of tri(ethylene glycol) monomethyl ether (182 mg, 0.57 mmol) in DMF (1 mL). The resulting mixture was stirred at room temperature overnight, and quenched by addition of NH$_4$Cl aqueous solution at 0° C. The crude product was extracted with EtOAc. The organic phase was washed with brine and dried over Na$_2$SO$_4$. After removal of the solvent, the residue was purified by flash silica gel chromatography (50% EtOAc in hexanes) to afford 250 mg of 80 (93%). [TLC (60% EtOAc/hexane): R$_f$(80)=0.22)]. $^1$H NMR (CDCl$_3$, 300 MHz) δ 7.65-7.76 (1H), 7.33 (m, 1H), 7.20 (m, 1H), 7.09 (m, 1H), 6.95 (s, 1H), 4.27 (t, J=8.4 Hz, 2H), 3.79 (t, J=5.7 Hz, 2H), 3.40-3.70 (9H), 3.37 (s, 3H), 3.10-3.40 (2H), 2.65 (m, 1H), 1.75 (brs, 4H), 1.55 (s, 9H) ppm.

B. 6-Fluoro-1-{2-[2-(2-methoxy-ethoxy)-ethoxy]-ethyl}-3-pyrrolidin-2-ylmethyl-1H-indole (81): A solution of 80 (250 mg, 0.56 mmol) in DCM (5 mL) was treated with TFA (1 mL) at room temperature. After 2 h, the reaction mixture was concentrated, diluted with EtOAc, washed with 1N aqueous NaOH and brine, dried over Na$_2$SO$_4$, filtered and concentrated to afford 190 mg (98%) of 81 as a light yellow oil. The product was used without further purification.

C. {1-Cyclohexyl-2-[2-(6-fluoro-1-{2-[2-(2-methoxy-ethoxy)-ethoxy]-ethyl}-1H-indol-3-ylmethyl)-pyrrolidin-1-yl]-2-oxo-ethyl}-carbamic acid tert-butyl ester (82): To a solution of Boc-L-cyclohexylglycine (172 mg, 0.67 mmol) in NMP (2 mL) was added HATU (255 mg, 0.67 mmol) followed by NMM (0.1 mL, 0.95 mmol). After 5 min, 81 (190 mg, 0.55 mmol) in DCM (1 mL) was added and the reaction mixture was stirred at room temperature overnight. Ethyl acetate (20 mL) was added to the reaction mixture and the organic solution was washed with water, 1 N HCl (5 mL), aqueous NaHCO$_3$ (10 mL), and brine, dried over Na$_2$SO$_4$. Solvent was removed under reduced pressure and the product was purified by flash silica gel chromatography to afford 280 mg (85%) of 82 as a wax. [TLC (60% EtOAc/hexane): R$_f$(82)=0.18)]. $^1$H NMR (CDCl$_3$, 300 MHz) δ 7.83 (m, 1H), 7.32 (m, 1H), 7.20 (m, 1H), 7.09 (m, 1H), 6.98 (s, 1H), 5.32 (m, 1H), 4.0-4.6 (5H), 3.79 (t, J=5.7 Hz, 2H), 3.40-3.70 (9H), 3.37 (s, 3H), 2.65 (m, 1H), 1.6-2.0 (10H), 1.46 (s, 9H), 1.0-1.4 (6H) ppm.

D. 2-Amino-2-cyclohexyl-1-[2-(6-fluoro-1-{2-[2-(2-methoxy-ethoxy)-ethoxy]-ethyl}-1H-indol-3-ylmethyl)-pyrrolidin-1-yl]-ethanone (83): A solution of 82 (250 mg, 0.43 mmol) in DCM (5 mL) was treated with TFA (1 mL) at room temperature. After 2 h, the reaction mixture was concentrated, diluted with EtOAc, washed with 1N aqueous NaOH and brine, dried over Na$_2$SO$_4$, filtered and concentrated to afford 210 mg (100%) of 83 as a light yellow wax. The product was used without further purification.

E. (1-{1-Cyclohexyl-2-[2-(6-fluoro-1-{2-[2-(2-methoxy-ethoxy)-ethoxy]-ethyl}-1H-indol-3-ylmethyl)-pyrrolidin-1-yl]-2-oxo-ethylcarbamoyl}-ethyl)-methyl-carbamic acid tert-butyl ester (84): To a solution of Boc-L-N-methylanaline (91 mg, 0.48 mmol) in NMP (2 mL) was added HATU (183 mg, 0.48 mmol) followed by NMM (0.1 mL, 0.95 mmol). After 5 min., 83 (210 mg, 0.43 mmol) in DCM (1 mL) was added and the reaction mixture was stirred at room temperature overnight. Ethyl acetate (20 mL) was added to the reaction mixture and the organic solution was washed with water, 1 N HCl (5 mL), aqueous NaHCO$_3$ (10 mL), and brine, dried over Na$_2$SO$_4$. Solvent was removed under reduced pressure and the product was purified by flash silica gel chromatography to afford 188 mg (65%) of 84 as a wax. [TLC (80% EtOAc/hexane): R$_f$(84)=0.20)]. $^1$H NMR (CDCl$_3$, 300 MHz) δ 7.80 (m, 1H), 7.35 (m, 1H), 7.19 (m, 1H), 7.10 (m, 1H), 6.95 (s, 1H), 4.62 (m, 1H), 4.46 (m, 1H), 4.20 (t, J=6.7 Hz, 2H), 3.77 (, t, J=5.4 Hz, 2H), 3.2-3.7 (5H), 3.36 (s, 3H), 2.48 (d, J=7.5 Hz, 3H) (t, J=5.7 Hz, 2H), 3.40-3.70 (9H), 3.37 (s, 3H), 2.65 (m, 1H), 2.57 (m, 1H), 1.6-2.0 (8H), 1.51 (S, 9H), 1.38 (d, J=6.6 Hz, 3H), 1.0-1.4 (4H) ppm.

F. 2-(6-Fluoro-1-{2-[2-(2-methoxy-ethoxy)-ethoxy]-ethyl}-1H-indole-3-ylmethyl)-2S-pyrrolidine-1-carboxylic acid tert-butyl ester (85): A solution of 84 (188 mg, 0.28 mmol) in DCM (5 mL) was treated with TFA (1 mL) at room temperature. After 2 h, the reaction mixture was concentrated, diluted with EtOAc, washed with 1N aqueous NaOH and brine, dried over Na$_2$SO$_4$, filtered and concentrated. The residue was purified by HPLC to afford 110 mg (65%) acetate salt of 85 as a white solid. [TLC (20% MeOH in EtOAc): R$_f$(85)= 0.20)]. $^1$H NMR (CDCl$_3$, 300 MHz) δ 7.79 (br d, 2H), 7.34 (d, J=7.2 Hz, 1H), 7.21 (m, 1H), 7.10 (m, 1H), 6.96 (d, J=9.0

Hz, 1H), 6.23 (br s, 2H), 4.61 (m, 1H), 4.44 (m, 1H), 4.24 (t, J=5.4 Hz, 2H), 3.78 (t, J=5.4 Hz, 2H), 3.4-3.8 (12H), 3.36 (s, 3H), 2.60 (m, 1H), 2.48 (d, J=7.5 Hz, 3H), 1.6-2.0 (8H), 1.39 (d, J=6.6 Hz, 3H), 1.0-1.4 (4H) ppm. Mass spectrum, m/z 571.3 $[M+H]^+$.

TABLE 16

(E16)

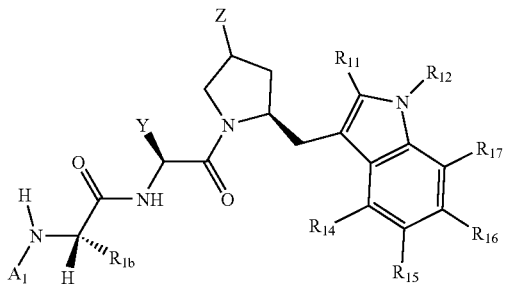

| Entry | $A_1$ | $R_{1b}$ | Y | Z | $R_{12}$ | $R_{14-17}$ | $R_{11}$ | MS $(M + H)^+$ | $K_D$ Range |
|---|---|---|---|---|---|---|---|---|---|
| 16-108 | Me | Me | tBu | H | $MeO(CH_2CH_2O)_2CH_2CH_2$ | 6-F ($R_{16}$) | H | 563.4 | B |
| 16-109 | Me | Me | cHex | H | $MeO(CH_2CH_2O)_2CH_2CH_2$ | 6-F ($R_{16}$) | H | 589.4 | B |
| 16-110 | Me | Et | cHex | H | $MeO(CH_2CH_2O)_2CH_2CH_2$ | H | H | 585.5 | B |
| 16-111 | Me | Me | cHex | H | $MeO(CH_2CH_2O)_2CH_2CH_2$ | H | H | 571.5 | B |
| 16-112 | Me | Me | tBu | H | $HO(CH_2CH_2O)_2CH_2CH_2$ | 6-F ($R_{16}$) | Br | 627.3 | A |
| 16-113 | Me | Me | tBu | H | $MeO(CH_2CH_2O)_2CH_2CH_2$ | 6-F ($R_{16}$) | Br | 641.3 | A |
| 16-114 | Me | Me | tBu | H | $MeO(CH_2CH_2O)_2CH_2CH_2$ | 6-F ($R_{16}$) | 2-thiophenyl | 645.4 | A |

Although the present invention has been described in considerable detail with reference to certain preferred embodiments thereof, other versions are possible. Therefore the spirit and scope of the appended claims should not be limited to the description and the preferred versions contain within this specification.

What is claimed is:

1. A compound represented by formula (5)

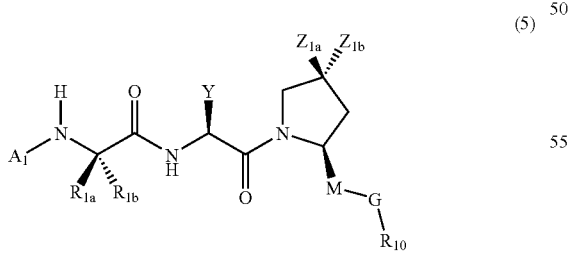

(5)

or a pharmaceutically acceptable salt thereof
where $A_1$ is H, or lower alkyl, or $A_1$ and $R_{1b}$ together form a ring of 3-5 atoms;

$R_{1a}$ is H; and $R_{1b}$ is lower alkyl group, or together with $A_1$ forms a ring of 3 to 5 atoms;

Y is an alkyl group, an alkynyl group, a cycloalkyl group of 3 to 7 carbon atoms, optionally substituted versions of these groups, hydroxy substituted versions of these groups, or Y together with $Z_{1a}$, $Z_{1b}$, or $R_{10}$ forms a carbocyclic ring, or a heterocyclic ring containing 1 to 5 heteroatoms, where Y is linked to $Z_{1a}$, $Z_{1b}$, or $R_{10}$;

$Z_{1a}$ and $Z_{1b}$ are independently an H, hydroxy, amino, alkylamino, diakylamino, alkoxy, aryloxy, or heteroaryloxy group; or $Z_{1a}$, $Z_{1b}$, together with Y or $R_{10}$ form a carbocyclic ring, or a heterocyclic ring containing 1 to 5 heteroatoms, where $Z_{1a}$ or $Z_{1b}$, is linked to Y or $R_{10}$;

M is an alkylene group of 1 to 5 carbon atoms;

G is a bond, a heteroatom, —(C=O)—; —$NR_{18}$—; —$NCOR_{18}$—; or —$NS(O)_xR_{18}$— where x =0, 1, or 2, and $R_{18}$ is lower alkyl, optionally-substituted lower alkyl group; and $R_{10}$ is anyone of structures (4a), (4b), (4c) or (4d):

(4a)

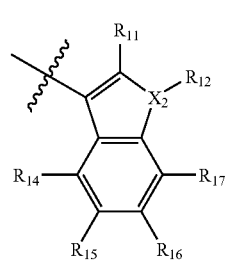

-continued

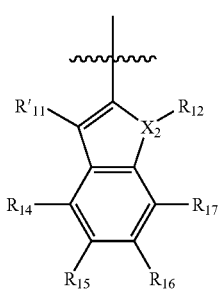
(4b)

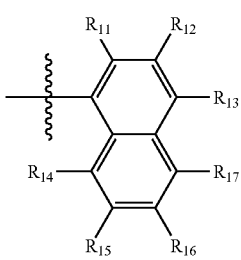
(4c)

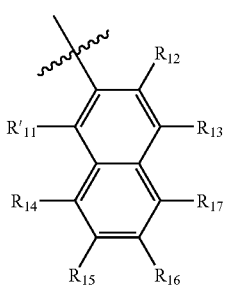
(4d)

where $X_2$ is a nitrogen atom and independently groups $R_{11}$, $R'_{11}$, $R_{12}$, any of $R_{13-17}$, or any of $R_{14-17}$ are H, halogen, alkyl, alkenyl, alkynyl, aryl, heteroaryl, hydroxyl, alkoxy, polyalkylether, amino, alkylamino, dialkylamino, alkyloxyalkyl, sulfonate, aryloxy or heteroaryloxy; independently $R_{11}$, $R'_{11}$, $R_{12}$, any of $R_{13-17}$, or any of $R_{14-17}$ are H, optionally-substituted alkyl, aryl, alkenyl, alkynyl, heteroaryl, hydroxyl, alkoxy, polyalkylether, amino, alkylamino, dialkylamino, alkyloxyalkyl, aryloxy, or heteroaryloxy; independently $R_{11}$, $R'_{11}$, $R_{12}$, any of $R_{13-17}$, or any of $R_{14-17}$ are acyl or acetyl groups, carboxylate, sulfonate, sulfone, imine, or oxime groups; or groups $R_{11}$, $R'_{11}$, $R_{12}$, any of $R_{13-17}$, or any of $R_{14-17}$ are contained within a carbocyclic ring, or a heterocyclic ring containing 1 to 5 heteroatoms, and linked to groups at position Y, $Z_{1a}$, $Z_{1b}$, M, G, $R_{11}$, $R'_{11}$, $R_{12}$, any of $R_{13-17}$, or any of $R_{14-17}$.

2. The compound of claim 1 represented by the general formula (5)

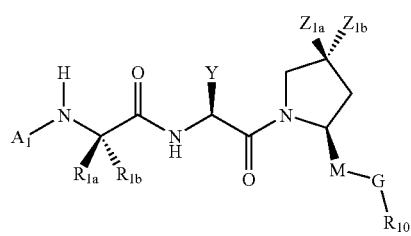
(5)

or a pharmaceutically acceptable salt thereof
where $A_1$ is H, or lower alkyl;

$R_{1a}$ is H; and $R_{1b}$ is lower alkyl group;

Y is an alkyl group, a cycloalkyl group of 3 to 7 carbon atoms, optionally substituted versions of these groups, hydroxy substituted versions of these groups;

$Z_{1a}$ and $Z_{1b}$ are independently an H, hydroxy, alkoxy, aryloxy, or heteroaryloxy group;

M is an alkylene group of 1 to 5 carbon atoms;

G is a bond, a heteroatom, or —$NCOR_{18}$— and $R_{18}$ is lower alkyl, optionally-substituted lower alkyl group; and $R_{10}$ is anyone of structures (4a), (4b), (4c) or (4d):

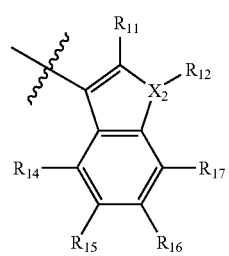
(4a)

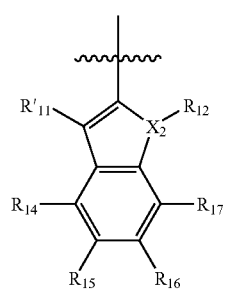
(4b)

-continued

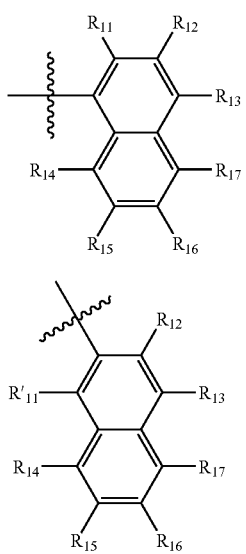

(4c)

(4d)

where $X_2$ is a nitrogen atom and independently groups $R_{11}$, $R'_{11}$, $R_{12}$, any of $R_{13-17}$, or any of $R_{14-17}$ are H, halogen, alkyl, alkenyl, alkynyl, aryl, heteroaryl, hydroxyl, alkoxy, polyalkylether, amino, alkylamino, dialkylamino, alkyloxyalkyl, sulfonate, aryloxy or heteroaryloxy; independently $R_{11}$, $R'_{11}$, $R_{12}$, any of $R_{13-17}$, or any of $R_{14-17}$ are H, optionally-substituted alkyl, aryl, alkenyl, alkynyl, heteroaryl, hydroxyl, alkoxy, polyalkylether, amino, alkylamino, dialkylamino, alkyloxyalkyl, aryloxy, or heteroaryloxy; independently $R_{11}$, $R'_{11}$, $R_{12}$, any of $R_{13-17}$, or any of $R_{14-17}$ are acyl or acetyl groups, carboxylate, sulfonate, sulfone, imine, or oxime groups; or groups $R_{11}$, $R'_{11}$, $R_{12}$, any of $R_{13-17}$, or any of $R_{14-17}$ are contained within a carbocyclic ring, or a heterocyclic ring containing 1 to 5 heteroatoms, and linked to groups at position Y, $Z_{1a}$, $Z_{1b}$, M, G, $R_{11}$, $R'_{11}$, $R_{12}$, any of $R_{13-17}$, or any of $R_{14-17}$.

3. The compound of claim 1 represented by formula (5)

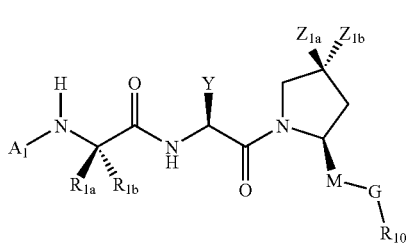

(5)

or a pharmaceutically acceptable salt thereof
where $A_1$ is H, or methyl;
$R_{1a}$ is H; and $R_{1b}$ is methyl or ethyl;
Y is an alkyl group, a cycloalkyl group of 3 to 7 carbon atoms, optionally substituted versions of these groups, or hydroxy substituted versions of these groups;
$Z_{1a}$ and $Z_{1b}$ are independently an H, hydroxy, or alkoxy group;
M is a methylene group;
G is a bond; and $R_{10}$ is any one of structures (4a) or (4b):

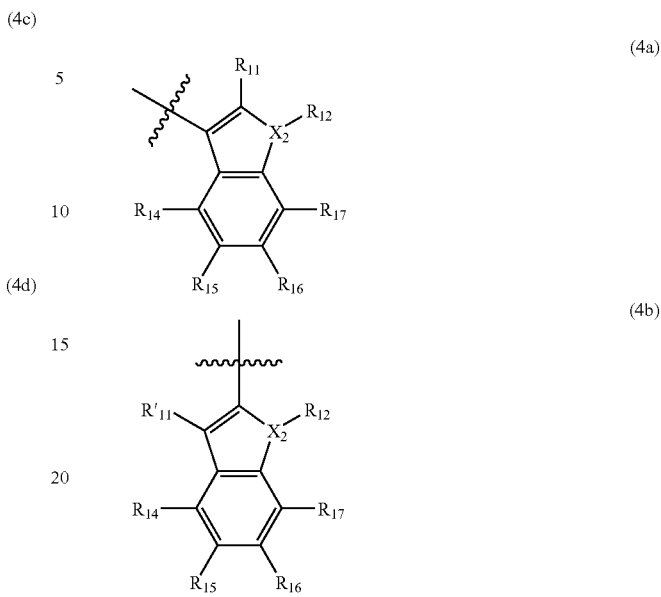

(4a)

(4b)

where $X_2$ is a nitrogen atom and independently groups $R_{11}$, $R'_{11}$, $R_{12}$, or any of $R_{14-17}$ are H, halogen, alkyl, alkenyl, alkynyl, aryl, heteroaryl, hydroxyl, alkoxy, polyalkylether, amino, alkylamino, dialkylamino, alkyloxyalkyl, sulfonate, aryloxy or heteroaryloxy; independently $R_{11}$, $R'_{11}$, $R_{12}$, or any of $R_{14-17}$ are H, optionally-substituted alkyl, aryl, alkenyl, alkynyl, heteroaryl, hydroxyl, alkoxy, polyalkylether, amino, alkylamino, dialkylamino, alkyloxyalkyl, aryloxy, or heteroaryloxy; independently $R_{11}$, $R'_{11}$, $R_{12}$, or any of $R_{14-17}$ are acyl or acetyl groups, carboxylate, sulfonate, sulfone, imine, or oxime groups; or groups $R_{11}$, $R'_{11}$, $R_{12}$, or any of $R_{14-17}$ are contained within a carbocyclic ring, or a heterocyclic ring containing 1 to 5 heteroatoms, and linked to groups at position Y, $Z_{1a}$, $Z_{1b}$, M, G, $R_{11}$, $R'_{11}$, $R_{12}$, any of $R_{13-17}$, or any of $R_{14-17}$.

4. The compound of claim 3 or a pharmaceutically acceptable salt thereof, in which $R_{10}$ is:

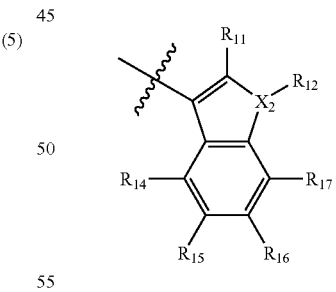

and in which $X_2$ is a nitrogen atom.

5. The compound of claim 1 or a pharmaceutically acceptable salt thereof that has a $K_d$ for an IAP of less than about 1 micromolar.

6. The compound of claim 1 or a pharmaceutically acceptable salt thereof where $A_1$ is H, methyl, or ethyl.

7. The compound of claim 1 or a pharmaceutically acceptable salt thereof where $R_{1a}$ is H; and $R_{1b}$ is methyl or ethyl.

8. The compound of claim 1 or a pharmaceutically acceptable salt thereof where Y is an alkyl group of 1 to 10 carbon atoms, an alkynyl group, a cycloalkyl group of 3 to 7 carbon atoms, optionally substituted versions of these groups, or hydroxy substituted versions of these groups.

9. The compound of claim 1 or a pharmaceutically acceptable salt thereof where $Z_{1a}$ and $Z_{1b}$ are independently an H, hydroxy, amino, alkylamino, dialkylamino, alkoxy, aryloxy, or heteroaryloxy group.

10. The compound of claim 1 or a pharmaceutically acceptable salt thereof where $R_{10}$ has the structure of formula (4a):

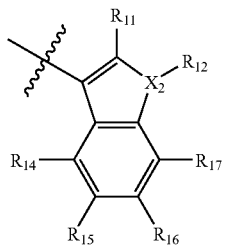

(4a)

where $X_2$ is a nitrogen atom and independently groups $R_{11}$, $R_{12}$, or any of $R_{14-17}$ is H, or optional substituents including halogen, alkyl, alkenyl, alkynyl, aryl, heteroaryl, hydroxyl, alkoxy, amino, alkylamino, dialkylamino, alkyloxyalkyl, sulfonate, aryloxy or heteroaryloxy independently $R_{11}$, $R_{12}$, or any of $R_{14-17}$ are H, optionally-substituted alkyl, aryl, alkenyl, alkynyl, heteroaryl, hydroxyl, alkoxy, polyalkylether, amino, alkylamino, dialkylamino, alkyloxyalkyl, aryloxy, or heteroaryloxy; independently $R_{11}$, $R'_{11}$, $R_{12}$, or any of $R_{14-17}$ are acyl or acetyl groups, carboxylate, sulfonate, sulfone, imine, or oxime groups.

11. The compound of claim 1 or a pharmaceutically acceptable salt thereof that has a $K_d$ for an IAP of less than about 0.1 micromolar.

12. A compound represented by formula (2):

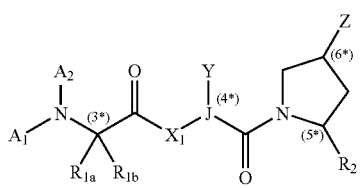

(2)

or a pharmaceutically acceptable salt thereof
wherein: (3*), (4*), (5*) and (6*) indicate potential chiral carbon positions;
$A_1$ and $A_2$ are independently hydrogen, alkyl, aryl, or alkylaryl group, $R_{1a}$ is H or methyl; $R_{1b}$ is an alkyl or aryl group; $X_1$ is —O—, —S—, —CH$_2$—, or —NH—, and J is —CH—, or —N—, provided that when J is —N—, $X_1$ is —CH$_2$—, or —NH—; Y is H, or an alkyl group; Z is —OH, aryloxy, alkoxy, benzyloxy, benzyloxy, amino, arylamino, alkylamino, or benzylamino group; $R_2$ is a detectable label or is

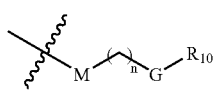

M is alkylene, alkenylene, alkynylene, heteroalkylene, heteroalkenylene, or heteroalkynylene group, G is selected from a bond, —O—; —N(R$_{2d}$)— where R$_{2d}$ is H, alkyl, cycloalkyl, or aryl; or —S(O)$_m$— where m is 0, 1, or 2;

$R_{10}$ is anyone of structures (4a), (4b), (4c) or (4d);

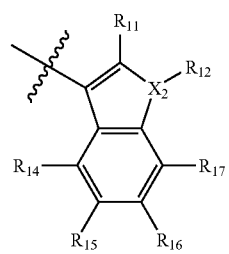

(4a)

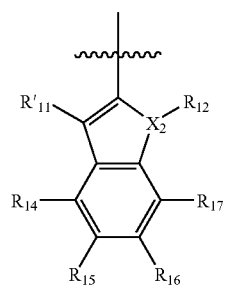

(4b)

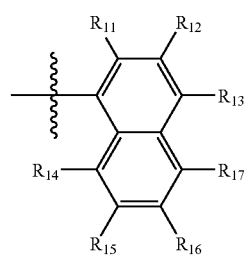

(4c)

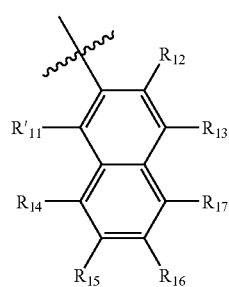

(4d)

where $X_2$ is a nitrogen atom and independently groups $R_{11}$, $R'_{11}$, $R_{12}$, any of $R_{13-17}$, or any of $R_{14-17}$ is H, halogen, alkyl, alkynyl, aryl, heteroaryl, hydroxyl, alkoxy, polyalkylether, amino, alkylamino, dialkylamino, alkyloxyalkyl, aryloxy or heteroaryloxy; independently $R_{11}$, $R'_{11}$, $R_{12}$, any of $R_{13-17}$, or any of $R_{14-17}$ are H, optionally-substituted alkyl, aryl, alkenyl, alkynyl, heteroaryl, hydroxyl, alkoxy, polyalkylether, amino, alkylamino, dialkylamino, alkyloxyalkyl, aryloxy, or heteroaryloxy; independently $R_{11}$, $R'_{11}$, $R_{12}$, any of $R_{13-17}$, or any of $R_{14-17}$ are acyl or acetyl groups, carboxylate, sulfonate, sulfone, imine, or oxime groups and n is independently the integer 0, 1, 2, 3, 4, or 5.

13. A compound represented by formula (3):

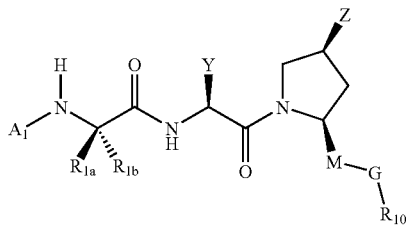

(3)

or a pharmaceutically acceptable salt thereof
where $A_1$ is H, lower alkyl, or optionally-substituted lower alkyl group; $R_{1a}$ and $R_{1b}$ are separately H, lower alkyl, optionally-substituted lower alkyl, or $A_1$ together with either $R_{1a}$ or $R_{1b}$ form an optionally substituted heterocycloalkyl group of 3 to 6 atoms;

Y is H, an alkyl group, an alkynyl group, a cycloalkyl group of 3 to 7 carbon atoms, aryl, heteroaryl, arylalkyl, optionally-substituted versions of these groups, hydroxy substituted versions of these groups, or Y together with Z, M, G, or $R_{10}$ forms a carbocyclic ring, or a heterocyclic ring containing 1 to 5 heteroatoms, where Y is linked to Z, M, G, or $R_{10}$;

Z is H, alkyl, hydroxy, amino, alkylamino, diakylamino, alkoxy, cycloalkyl, cycloalkyloxy, aryl, heteroaryl, aryloxy, or heteroaryloxy group; or Z together with Y, M, G, or $R_{10}$ form a carbocyclic ring, or a heterocyclic ring containing 1 to 5 heteroatoms, where Z is linked to Y, M, G, or $R_{10}$;

M is alkylene, alkenylene, or alkynylene group of 1 to 5 carbon atoms;

G is a bond, a heteroatom, —(C═O)—; —S(O)$_t$— where t = 0, 1, or 2; —NR$_{18}$—; —NCOR$_{18}$—; or —NS(O)$_x$R$_{18}$— where x = 0, 1, or 2, and $R_{18}$ is lower alkyl, optionally-substituted lower alkyl, or cycloalkyl or $R_{18}$ is contained within a carbocyclic, or heterocyclic ring containing 1 to 5 heteroatoms, where $R_{18}$ is linked to Z, M, or $R_{10}$; and $R_{10}$ is any one of structures (4a), (4b), (4c) or (4d):

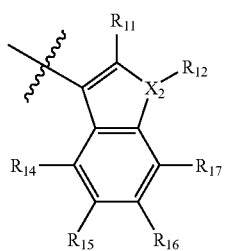

(4a)

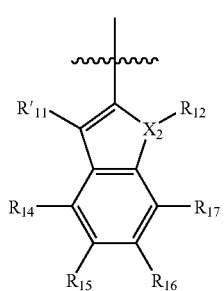

(4b)

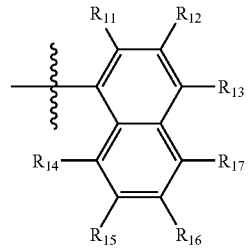

(4c)

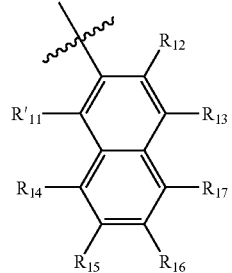

(4d)

where $X_2$ is a nitrogen atom and independently groups $R_{11}$, $R'_{11}$, $R_{12}$, any of $R_{13-17}$, or any of $R_{14-17}$ is H, halogen, alkyl, alkenyl, alkynyl, aryl, heteroaryl, hydroxyl, alkoxy, polyalkylether, amino, alkylamino, dialkylamino, alkyloxyalkyl, sulfonate, aryloxy or heteroaryloxy; independently $R_{11}$, $R'_{11}$, $R_{12}$, any of $R_{13-17}$, or any of $R_{14-17}$ is H, optionally-substituted alkyl, alkenyl, alkynyl, aryl, heteroaryl, hydroxyl, alkoxy, polyalkylether, amino, alkylamino, dialkylamino, alkyloxyalkyl, aryloxy, or heteroaryloxy; or independently $R_{11}$, $R'_{11}$, $R_{12}$, any of $R_{13-17}$, or any of $R_{14-17}$ is acyl or acetyl groups, carboxylate, sulfonate, sulfone, imine, or oxime groups; or groups $R_{11}$, $R'_{11}$, $R_{12}$, any of $R_{13-17}$, or any of $R_{14-17}$ is contained within a carbocyclic ring, or a heterocyclic ring containing 1 to 5 heteroatoms, and linked to groups at position Y, Z, M, G, $R_{11}$, $R'_{11}$, $R_{12}$, any of $R_{13-17}$, or any of $R_{14-17}$.

14. The compound of claim 13 represented by formula (3):

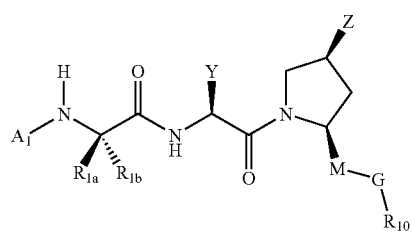

(3)

or a pharmaceutically acceptable salt thereof
where $A_1$ is H, lower alkyl, or optionally-substituted lower alkyl group; $R_{1a}$ and $R_{1b}$ are separately H, lower alkyl, optionally-substituted lower alkyl; or $A_1$ together with either $R_{1a}$ or $R_{1b}$ form an optionally substituted heterocycloalkyl group of 3 to 6 atoms;

Y is H, an alkyl group, an alkynyl group, a cycloalkyl group of 3 to 7 carbon atoms, aryl, heteroaryl, arylalkyl, optionally-substituted versions of these groups, hydroxy substituted versions of these groups, or Y together with Z, M, G, or $R_{10}$ forms a carbocyclic ring, or a heterocyclic ring containing 1 to 5 heteroatoms, where Y is linked to Z, M, G, or $R_{10}$;

Z is H, alkyl, hydroxy, amino, alkylamino, diakylamino, alkoxy, cycloalkyl, cycloalkyloxy, aryl, heteroaryl, aryloxy, or heteroaryloxy group; or Z together with Y, M, G, or $R_{10}$ form a carbocyclic ring, or a heterocyclic ring containing 1 to 5 heteroatoms, where Z is linked to Y, M, G, or $R_{10}$;

M is an alkylene, alkenylene, or alkynylene group of 1 to 5 carbon atoms;

G is a bond, a heteroatom, —(C=O)—; —S(O)$_t$— where t =0, 1, or 2; —NR$_{18}$—; —NCOR$_{18}$—; or —NS(O)$_x$R$_{18}$— where x =0, 1, or 2, and $R_{18}$ is lower alkyl, optionally-substituted lower alkyl, or cycloalkyl or $R_{18}$ is contained within a carbocyclic, or heterocyclic ring containing 1 to 5 heteroatoms, where $R_{18}$ is linked to Z, M, or $R_{10}$; and $R_{10}$ is any one of structures (4a), (4b), (4c) or (4d):

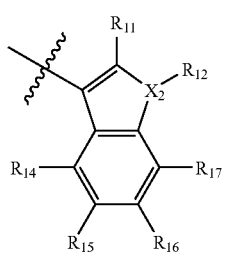

(4a)

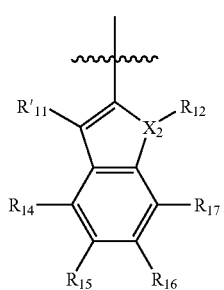

(4b)

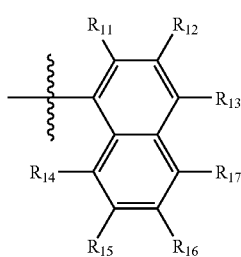

(4c)

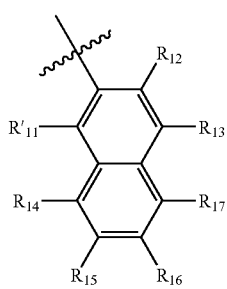

(4d)

where $X_2$ is a nitrogen atom and independently groups $R_{11}$, $R'_{11}$, $R_{12}$, any of $R_{13-17}$, or any of $R_{14-17}$ is H, halogen, alkyl, alkenyl, alkynyl, aryl, heteroaryl, hydroxyl, alkoxy, polyalkylether, amino, alkylamino, dialkylamino, alkyloxyalkyl, sulfonate, aryloxy or heteroaryloxy; independently $R_{11}$, $R'_{11}$, $R_{12}$, any of $R_{13-17}$, or any of $R_{14-17}$ is H, optionally-substituted alkyl, alkenyl, alkynyl, aryl, heteroaryl, hydroxyl, alkoxy, polyalkylether, amino, alkylamino, dialkylamino, alkyloxyalkyl, aryloxy, or heteroaryloxy; or independently $R_{11}$, $R'_{11}$, $R_{12}$, any of $R_{13-17}$, or any of $R_{14-17}$ is acyl or acetyl groups, carboxylate, sulfonate, sulfone, imine, or oxime groups; or groups $R_{11}$, $R'_{11}$, $R_{12}$, any of $R_{13-17}$, or any of $R_{14-17}$ is contained within a carbocyclic ring, or a heterocyclic ring containing 1 to 5 heteroatoms, and linked to groups at position Y, Z, M, G, $R_{11}$, $R'_{11}$, $R_{12}$, any of $R_{13-17}$, or any of $R_{14-17}$.

15. A composition comprising a compound of claim 13, 14, 1, 2, 3, or 4 or a pharmaceutically acceptable salt thereof and a pharmaceutically acceptable carrier.

16. The compound of claim 13, or a pharmaceutically acceptable salt thereof selected from

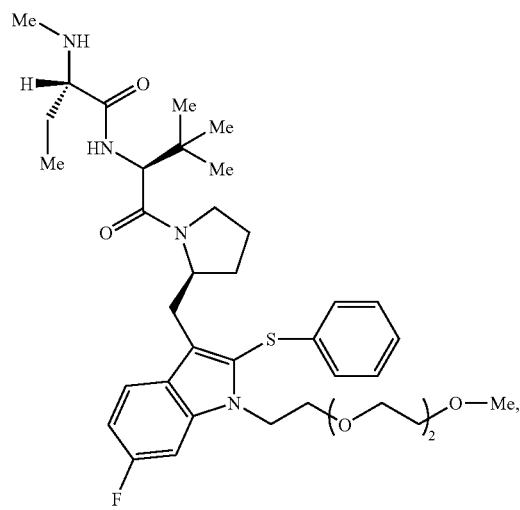

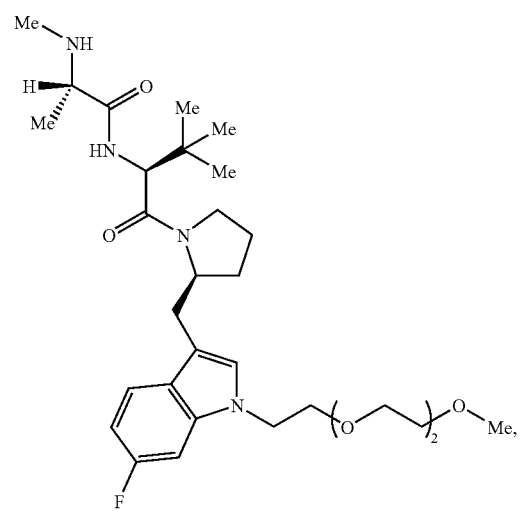

111
-continued
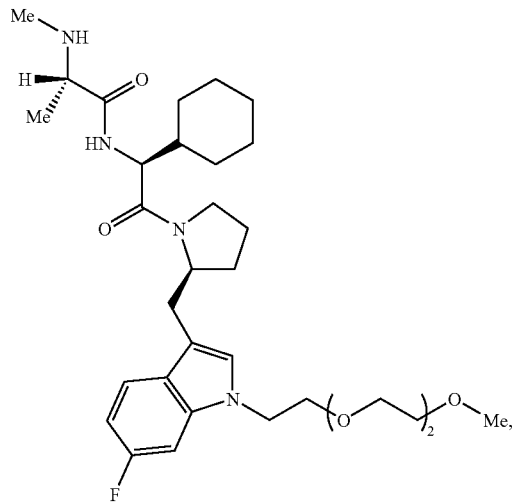
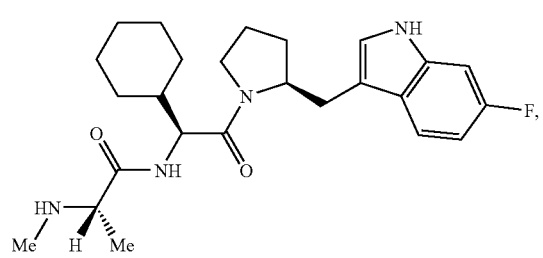
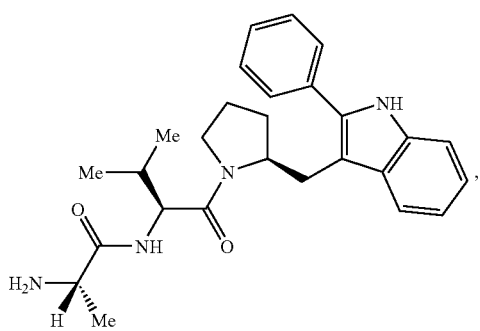
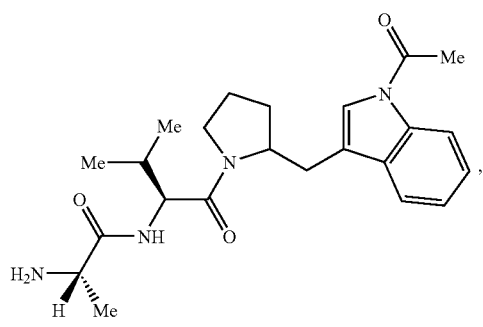
112
-continued
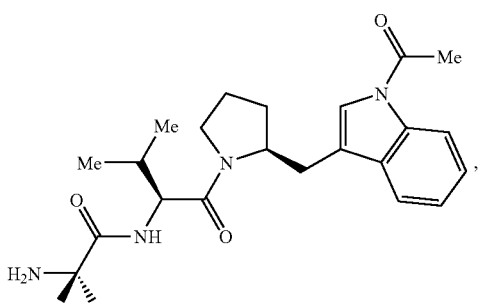
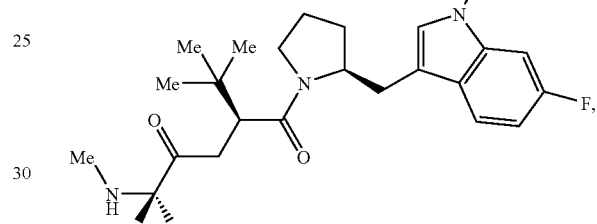
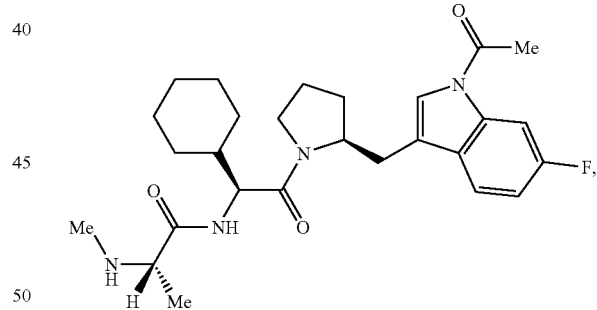
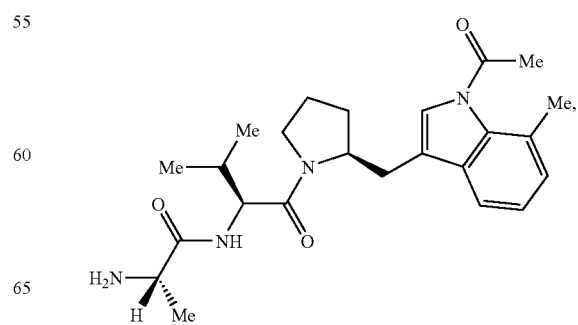

-continued
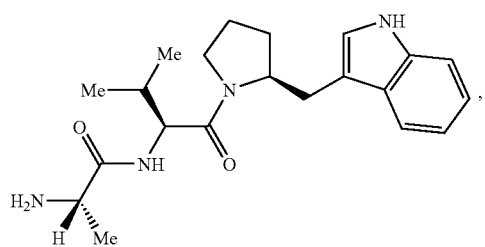
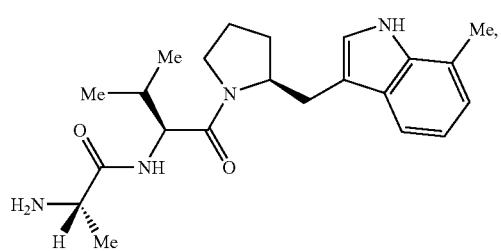
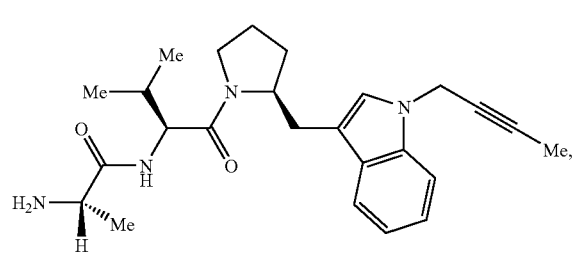
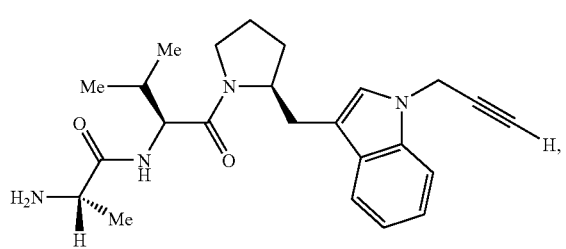
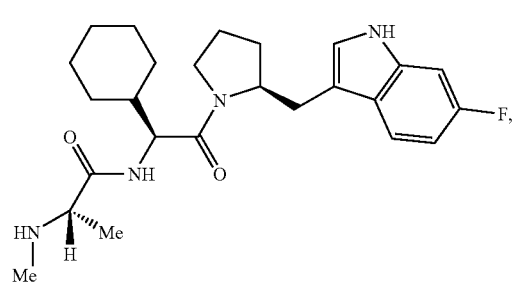
-continued
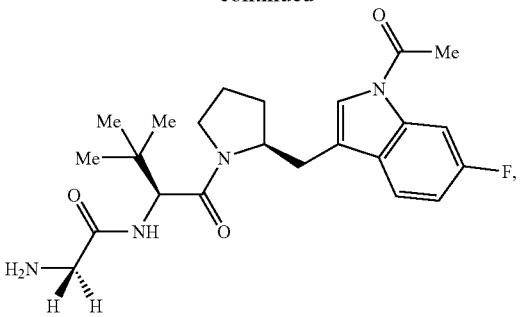
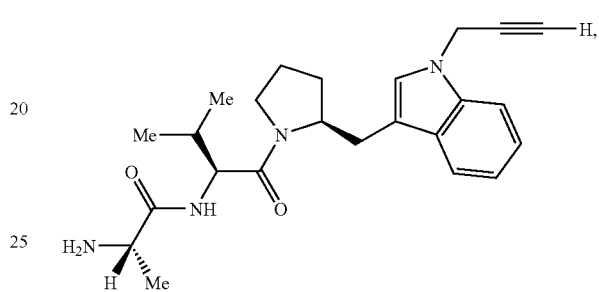
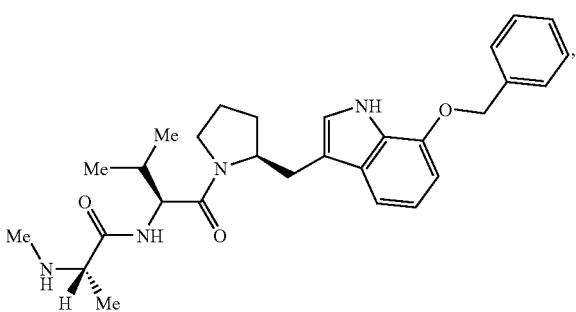
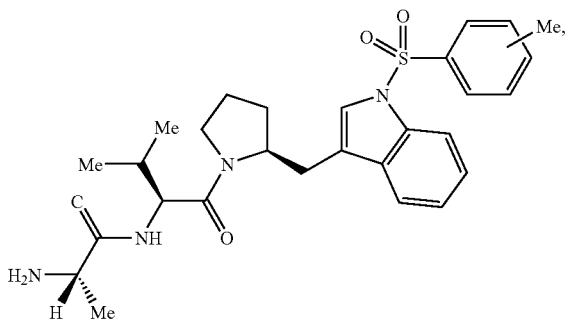
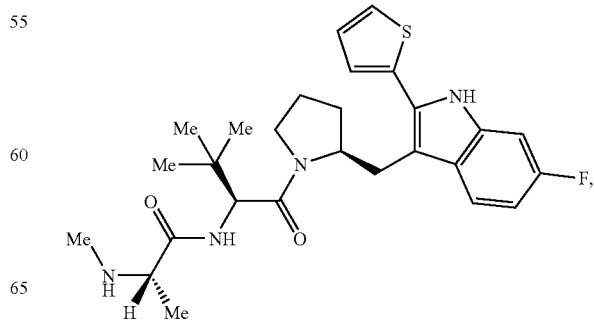

115
-continued
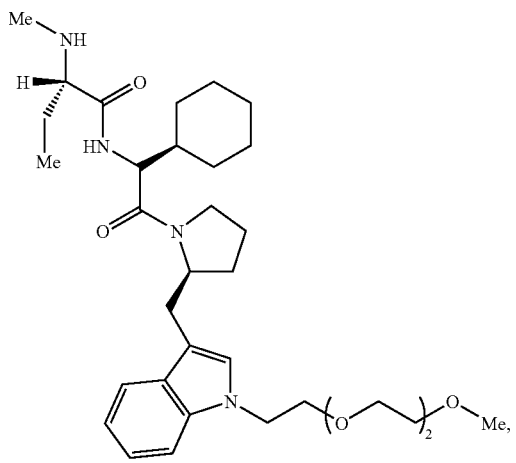
116
-continued
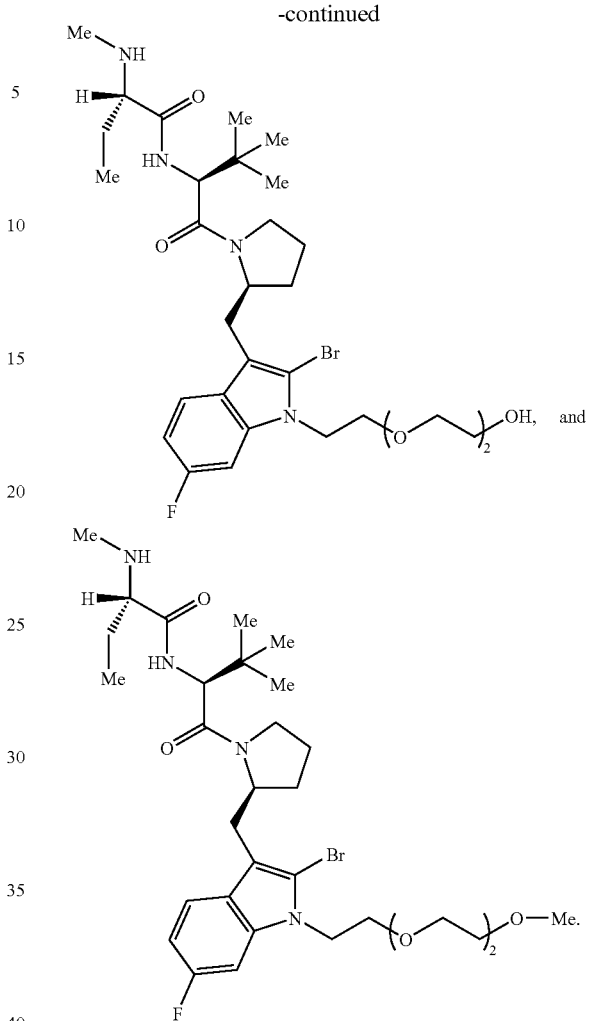
* * * * *